United States Patent
Bednar et al.

(10) Patent No.: US 12,180,278 B2
(45) Date of Patent: Dec. 31, 2024

(54) ANTIBODY TARGETING CD22 AND CD79B

(71) Applicant: Janssen Biotech, Inc., Horsham, PA (US)

(72) Inventors: Kyle J. Bednar, Conshohocken, PA (US); Naresh Kumar, Warrington, PA (US); Sanjaya Singh, Blue Bell, PA (US); Danlin Yang, Philadelphia, PA (US); Rajkumar Ganesan, Blue Bell, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 17/702,042

(22) Filed: Mar. 23, 2022

(65) Prior Publication Data

US 2022/0306738 A1    Sep. 29, 2022

Related U.S. Application Data

(60) Provisional application No. 63/165,416, filed on Mar. 24, 2021.

(51) Int. Cl.
| | | |
|---|---|---|
| C07K 16/28 | (2006.01) | |
| A61K 39/00 | (2006.01) | |
| C07K 16/46 | (2006.01) | |

(52) U.S. Cl.
CPC ........ *C07K 16/2803* (2013.01); *C07K 16/468* (2013.01); *A61K 2039/505* (2013.01); *C07K 2317/31* (2013.01); *C07K 2317/52* (2013.01); *C07K 2317/622* (2013.01); *C07K 2317/71* (2013.01); *C07K 2317/76* (2013.01); *C07K 2317/92* (2013.01)

(58) Field of Classification Search
CPC .............. C07K 16/2803; C07K 16/468; C07K 2317/31; C07K 2317/52; C07K 2317/622; C07K 2317/71; C07K 2317/76; C07K 2317/92; A61K 2039/505
See application file for complete search history.

(56) References Cited

U.S. PATENT DOCUMENTS

| | | |
|---|---|---|
| 3,832,253 A | 8/1974 | Di Palma |
| 3,854,480 A | 12/1974 | Zaffaroni |
| 4,452,775 A | 6/1984 | Kent |
| 4,667,014 A | 5/1987 | Nestor, Jr. |

(Continued)

FOREIGN PATENT DOCUMENTS

| | | |
|---|---|---|
| WO | 1990004036 | 4/1990 |
| WO | 1990007861 | 7/1990 |

(Continued)

OTHER PUBLICATIONS

Chen et al., Enhancement and destruction of antibody function by somatic mutation: unequal occurrence is controlled by V gene combinatorial associations. EMBO J. Jun. 15, 1995;14(12):2784-94. (Year: 1995).*

(Continued)

*Primary Examiner* — Aurora M Fontainhas
*Assistant Examiner* — Selam Berhane
(74) *Attorney, Agent, or Firm* — Riverside Law LLP

(57) ABSTRACT

Provided herein are multispecific antibodies, that bind to CD79b and CD22, polynucleotides encoding them, vectors, host cells, methods of making and using them.

29 Claims, 7 Drawing Sheets

Specification includes a Sequence Listing.

(56) References Cited

U.S. PATENT DOCUMENTS

| | | | |
|---|---|---|---|
| 4,748,034 | A | 5/1988 | De Rham |
| 5,075,109 | A | 12/1991 | Tice |
| 5,225,539 | A | 7/1993 | Winter |
| 5,239,660 | A | 8/1993 | Ooi |
| 5,635,483 | A | 6/1997 | Pettit |
| 5,780,588 | A | 7/1998 | Pettit |
| 5,932,448 | A | 8/1999 | Tso |
| 6,150,584 | A | 11/2000 | Kucherlapati |
| 6,818,749 | B1 | 11/2004 | Kashmiri |
| 6,833,441 | B2 | 12/2004 | Wang |
| 7,709,226 | B2 | 5/2010 | Foote |
| 8,748,356 | B2 | 6/2014 | Raghunathan |
| 9,150,663 | B2 | 10/2015 | Labrijn |
| 2007/0287170 | A1 | 12/2007 | Davis |
| 2009/0182127 | A1 | 7/2009 | Kristian |
| 2010/0015133 | A1 | 1/2010 | Igawa |
| 2010/0261620 | A1 | 10/2010 | Almagro |
| 2010/0286374 | A1 | 11/2010 | Kannan |
| 2011/0123532 | A1 | 5/2011 | Gurney |
| 2012/0149876 | A1 | 6/2012 | Spreter Von Kreudenstein |
| 2013/0195849 | A1 | 8/2013 | Spreter Von Kreudenstein |
| 2014/0273092 | A1 | 9/2014 | Flikweert |
| 2018/0118849 | A1 | 5/2018 | Klein |

FOREIGN PATENT DOCUMENTS

| | | | |
|---|---|---|---|
| WO | 1992022653 | 12/1992 | |
| WO | 1996027011 | 9/1996 | |
| WO | 1999045962 | 9/1999 | |
| WO | 2002043478 | 6/2002 | |
| WO | 2002066630 | 8/2002 | |
| WO | 2002088172 | 11/2002 | |
| WO | 2006028936 | 3/2006 | |
| WO | 2007147901 | 12/2007 | |
| WO | WO-2008068048 A2 * | 6/2008 | ............. A61P 31/10 |
| WO | 2008077546 | 7/2008 | |
| WO | 2009085462 | 7/2009 | |
| WO | 2009134776 | 11/2009 | |
| WO | 2010051274 | 5/2010 | |
| WO | 2010093627 | 8/2010 | |
| WO | 2011131746 | 10/2011 | |
| WO | 2011143545 | 11/2011 | |
| WO | 2012022811 | 2/2012 | |
| WO | 2013096291 | 6/2013 | |
| WO | 2013157954 | 10/2013 | |
| WO | WO-2016009030 A2 * | 1/2016 | ............. A61P 35/00 |
| WO | 2017009476 A1 | 1/2017 | |
| WO | 2019060695 | 3/2019 | |
| WO | 2021099944 A1 | 5/2021 | |

OTHER PUBLICATIONS

Edwards et al., The remarkable flexibility of the human antibody repertoire; isolation of over one thousand different antibodies to a single protein, BLyS. J Mol Biol. Nov. 14, 2003;334(1):103-18. (Year: 2003).*

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; (Year: 2017).*

Kussie, Paul H., "A Single Engineered Amino Acid Substitution Changes Antibody Fine Specificity", 1994, Journal of Immunology 152(1): pp. 146-152. (Year: 1994).*

Baert et al., "Influence of Immunogenicity on the Long-Term Efficacy of Infliximab in Crohn's Disease.", N. Engl. J. Med, 2003, pp. 602-608, vol. 348(7).

Bhatta, P. et al., "Bispecific antibody target pair discovery by high-throughput phenotypic screening using in vitro combinatorial Fab libraries", MABS, vol. 13, No. 1, 2021, US ISSN: 1942-0862, DOI: 10.1080/19420862.2020.1859049.

Cai et al., 2011, "C-terminal lysine processing of human immunoglobulin G2 heavy chain in vivo," Biotechnol. Bioeng., 108(2):404-412.

Chames, et al., "Bispecific antibodies for cancer therapy", Current Opinion in Drug Discovery & Development, (2009), vol. 12, No. 2, pp. 276-283.

Chothia et al., "Conformations of Immunoglobulin Hypervariable Regions," Nature. , 1989, vol. 342(6252), p. 877-883.

Chothia et al., 1987, "Canonical structures for the hypervariable regions of immunoglobulins," J. Mol. Biol., 196 (4):901-917.

Chu et al., 2001, "CD79: a review". Appl Immunohistochem Mol Morphol, Jun.;9(2):97-106.

Cline, et al., "Perspectives for Gene Therapy: inserting new genetic information into mammalian cells by physical techniques and viral vectors", Pharmac. Ther., (1985), vol. 29, pp. 69-92.

Ding, S. et al., "Targeting CD79b for Chimeric Antigen Receptor T-Cell Therapyt of B-Cell Lymphomas", Targeted Oncology, vol. 15, No. 3, 2020, 365-375, ISSN: 1776-2596, DOI: 10.1007/S11523-020-00729-7.

Duan & Paulson, "Siglecs as Immune Cell Checkpoints in Disease". 2020, Ann. Rev Immunol 38(1):365-369.

E. Meyers and W. Miller, "Optimal alignments in linear space". Comput. Appl. Biosci 4, 11-17 (1988).

Ferrara et al., 2006, "Modulation of therapeutic antibody effector functions by glycosylation engineering: influence of Golgi enzyme localization domain and co-expression of heterologous betal, 4-N-acetylglucosaminyltransferase III and Golgi alpha-mannosidase II," Biotechnol. Bioeng., 93(5):851- 861.

Ferrara et al., 2006, "The carbohydrate at FcgammaRIIIa Asn-162. An element required for high affinity binding to non-fucosylated IgG glycoforms," J. Biol. Chem., 281(8):5032-5036 (Epub 2005).

Fuh, F.K. et al., "Anti-CD22 and anti-CD79b antibody-drug conjugates preferentially target proliferating B cells", British Journal of Pharmacology, vol. 174, No. 8, 628-640, ISSN: 0007-1188, DOI: 10.1111/BPH.13697.

Gadi, et al., "In vivo sensitization of ovarian tumors to chemotherapy by expression of E. coli purine nucleoside phosphorylase in a small fraction of cells", Gene Therapy, (2000), vol. 7, pp. 1738-1743.

Honegger et al., 2001, "Yet another numbering scheme for immunoglobulin variable domains: an automatic modeling and analysis tool," J. Mol. Biol., 309(3):657-670.

International Search Report and Written Opinion issued in App. No. PCT/IB2022/052645, mailing date Jul. 25, 2022, 22 pages.

Jiang et al., "T cells redirected against Igβ for the immunotherapy of B cell lymphoma". 2020, Leukemia : official journal of the Leukemia Society of America/ Leukemia Research Fund, U.K., vol. 34(3), p. 821-830.

Knappik et al., 2000, "Fully synthetic human combinatorial antibody libraries (HuCAL) based on modular consensus frameworks and CDRs randomized with trinucleotides," J. Mol. Biol., 296(1):57-86.

Konno et al., 2012, "Fucose content of monoclonal antibodies can be controlled by culture medium osmolality for high antibody-dependent cellular cytotoxicity," Cytotechnology, 64(3):249-265 (Epub 2011).

Lefranc, M.P., et al., "IMGT unique numbering for immunoglobulin and T cell receptor variable domains and Ig superfamily V-like domains", Developmental and Comparative Immunology, (2003), vol. 27, pp. 55-77.

Martin, A.C.R., et al., "Structural Families in Loops of Homologous Proteins: Automatic Classification, Modelling and Application to Antibodies", J. Mol. Biol., (1996), vol. 263, pp. 800-815.

Mori et al., 2004, "Engineering Chinese hamster ovary cells to maximize effector function of produced antibodies using FUT8 siRNA," Biotechnol. Bioeng., 88(7):901-908.

Needleman, S. & Wunsch, C, "A General Method Applicable to the Search for Similarities in the Amino Acid Sequence of Two Proteins.", J. Mol. Biol., 1970, pp. 443-453, vol. 48.

Okayama, H., et al., "A cDNA Cloning Vector That Permits Expression of cDNA Inserts in Mammalian Cells", Molecular and Cellular Biology, (1983), vol. 3, No. 2, pp. 280-289.

Olivier et al., 2010, "EB66 cell line, a duck embryonic stem cell-derived substrate for the industrial production of therapeutic monoclonal antibodies with enhanced ADCC activity," Mabs, 2(4):405-415.

(56) References Cited

OTHER PUBLICATIONS

Ormhøj et al., "Chimeric Antigen Receptor T Cells Targeting CD79b Show Efficacy in Lymphoma with or without Cotargeting CD19". Clinical cancer research. , 2019, vol. 25(23), p. 7046-7057.

Packard and Cambier, "B lymphocyte antigen receptor signaling: initiation, amplification, and regulation". 2013, F1000Prime Rep, 5:40.

Padlan, E.A., "A Possible Procedure for Reducing the Immunogenicity of Antibody Variable Domains While Preserving Their Ligand-Binding Properties", Molecular Immunology, (1991), vol. 28, Nos. 4/5, pp. 489-498.

Puri et al., 2013, "B-Cell Receptor Signaling Inhibitors for Treatment of Autoimmune Inflammatory Diseases and B-Cell Malignancies". Int Rev Immunol, 32(4):397-427.

Shi et al., "De novo selection of high-affinity antibodies from synthetic fab libraries displayed on phage as pIX fusion proteins". (2010) J Mol Biol 397:385-96.

Shields et al., "Lack of Fucose on Human IgG1 N-Linked Oligosaccharide Improves Binding to Human FcyRIII and Antibody-dependent Cellular Toxicity*". J Biol Chem, 2002, pp. 26733-26740, vol. 277(30).

Shinkawa et al., 2003, "The absence of fucose but not the presence of galactose or bisecting N-acetylglucosamine of human IgG1 complex-type oligosaccharides shows the critical role of enhancing antibody-dependent cellular cytotoxicity," J. Biol. Chem., 278(5):3466-3473 (Epub 2002).

Stickler et al., "The human G1 m1 allotype associates with CD4+ T-cell responsiveness to a highly conserved IgG1 constant region peptide and confers an asparaginyl endopeptidase cleavage site.", Genes and Immunity, 2011, pp. 213-221, vol. 12.

Veri et al., "Therapeutic Control of B Cell Activation via Recruitment of Fcy Receptor IIb (CD32B) Inhibitory Function With a Novel Bispecific Antibody Scaffold". 2010, Arthritis & Rheumatism, 62: 1933-1943.

Walji & Assouline, "An evaluation of polatuzumab vedotin for the treatment of patients with diffuse large B-cell lymphoma". 2020, PMID: 32700586; DOI: 10.1080/17474086.2020.1795828.

Wang et al., "Human autoimmune diseases: a comprehensive update". 2015, J Intern Med 2015; 278: 369-395.

Woyke et al., 2001, "In vitro activities and postantifungal effects of the potent dolastatin 10 derivative auristatin PHE," Antimicrob. Agents Chemother., 45(12):3580-3584.

Wu et al. "An Analysis of the Sequences of the Variable Regions of Bence Jones Proteins and Myeloma Light Chains and Their Implications for Antibody Complementarity". (1970) J Exp Med 132: 211-50.

Zhou et al., "Development of a simple and rapid method for producing non-fucosylated oligomannose containing antibodies with increased effector function". Biotechnology and bioengineering. , 2008, vol. 99(3), p. 652-665.

\* cited by examiner

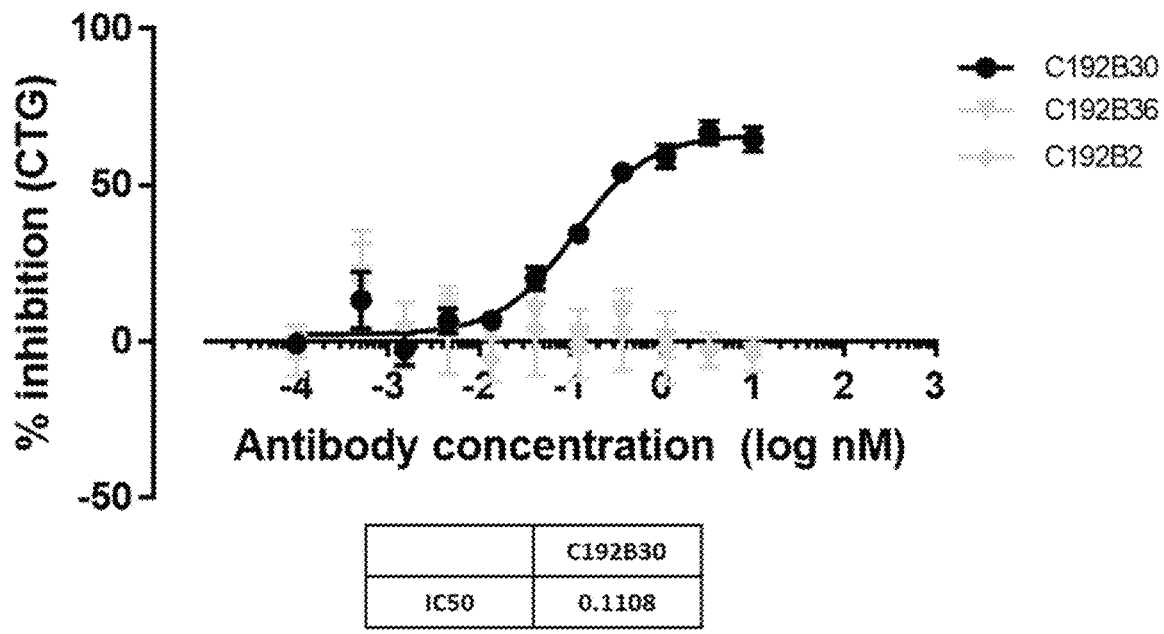
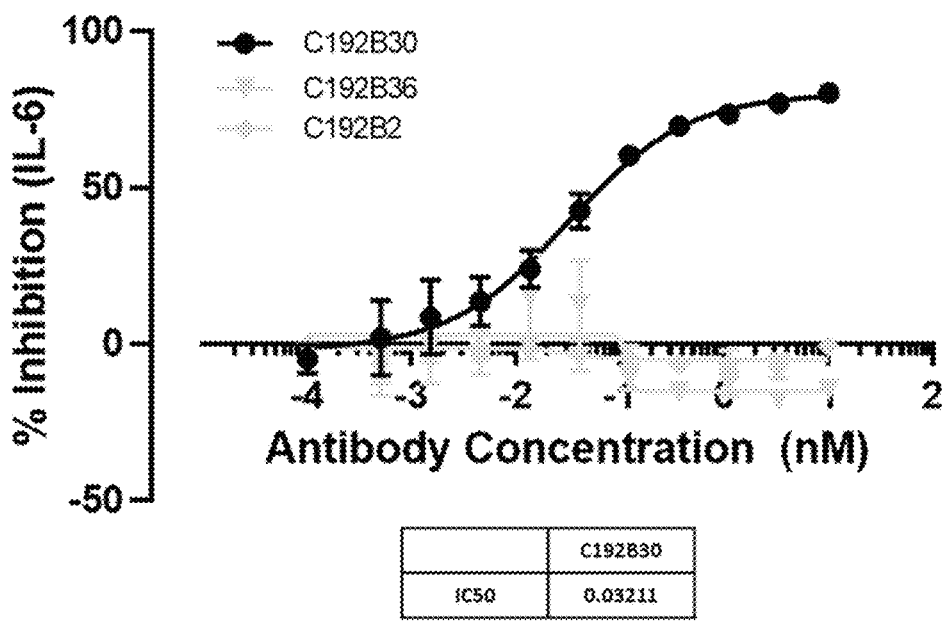
Figure 3

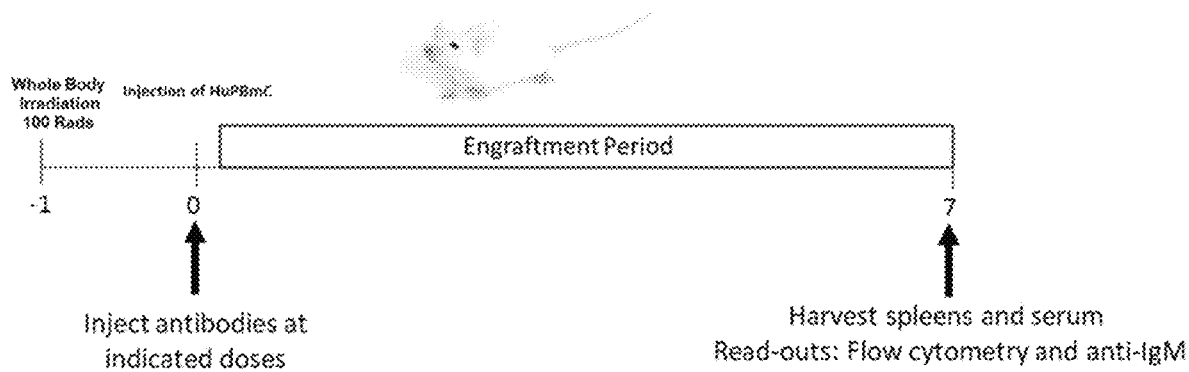
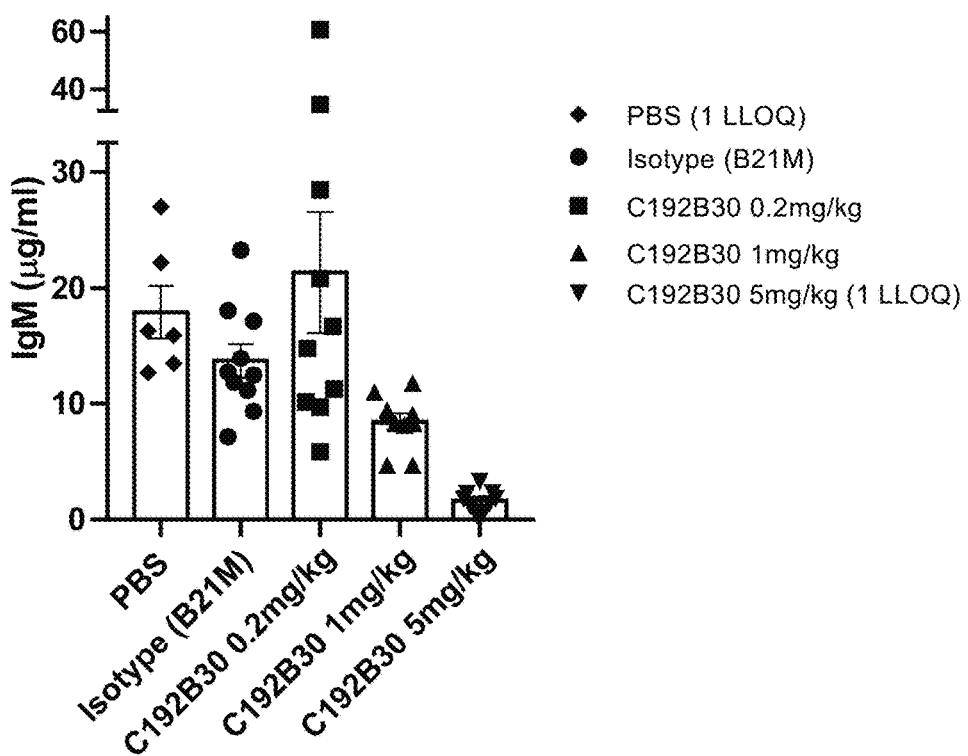
Figure 4

Colloidal Stability - SEC

| aSEC | | % Monomer @4°C 2wks | % Monomer @25°C 2wks | % Monomer @40°C 2wks | % HMW @4°C 2wks | % HMW @25°C 2wks | % HMW @40°C 2wks |
|---|---|---|---|---|---|---|---|
| (mg/ml) | Acetate | | | | | | |
| 50 | | 86.4 | 89.9 | 89.6 | 13.6 | 10.1 | 10.0 |
| 100 | | 79.8 | 84.2 | 87.1 | 20.4 | 15.8 | 12.5 |
| 150 | | 72.8 | 77.9 | 78.2 | 27.2 | 22.1 | 21.4 |

HCLF final conc = 153.8 mg/mL
Recovery = 95.3%
Viscosity at 100 mg/mL = 3.9 Cp

| aSEC | | % Monomer @4°C 2wks | % Monomer @25°C 2wks | % Monomer @40°C 2wks | % HMW @4°C 2wks | % HMW @25°C 2wks | % HMW @40°C 2wks |
|---|---|---|---|---|---|---|---|
| (mg/ml) | Acetate | | | | | | |
| 50 | | 97.9 | 99.5 | 98.5 | 2.1 | 0.5 | 1.0 |
| 100 | | 99.6 | 99.5 | 99.3 | 0.4 | 0.5 | 1.2 |
| 142 | | 99.6 | 99.4 | 98.1 | 0.4 | 0.6 | 1.4 |

HCLF final conc = 142 mg/mL
Recovery = 82.3%
Viscosity at 100 mg/mL = 3.4 Cp

LMW aggregates < 1% in all the samples

Unstapled molecule
CD79b scFV — CD22 Fab Fab

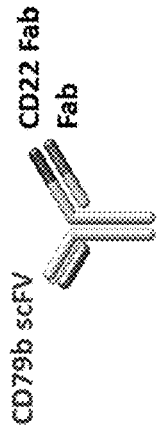

Stapled molecule
CD79b spFV — CD22 Fab

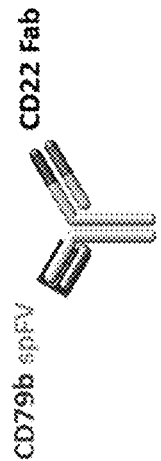

Figure 5

SEQUENCE LISTING

<160> NUMBER OF SEQ ID NOS: 126

<210> SEQ ID NO 1
<211> LENGTH: 9
<212> TYPE: PRT
<213> ORGANISM: Artificial Sequence
<220> FEATURE:
<223> OTHER INFORMATION: Chemically Synthesized, C22B21 CD22 arm HCDR1

<400> SEQUENCE: 1

Gly Leu Pro Leu Ser Thr Ser Gly Met
1               5

<210> SEQ ID NO 2
<211> LENGTH: 5
<212> TYPE: PRT
<213> ORGANISM: Artificial Sequence
<220> FEATURE:
<223> OTHER INFORMATION: Chemically Synthesized, C22B21 CD22 arm HCDR2

```
<400> SEQUENCE: 2

Asp Trp Asp Asp Asp
1               5

<210> SEQ ID NO 3
<211> LENGTH: 11
<212> TYPE: PRT
<213> ORGANISM: Artificial Sequence
<220> FEATURE:
<223> OTHER INFORMATION: Chemically Synthesized, C22B21 CD22 arm HCDR3

<400> SEQUENCE: 3

Met Gly Tyr Ser Tyr Gly Trp Asp Ala Phe Asp
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Chemically Synthesized, C22B21 CD22 arm LCDR1

<400> SEQUENCE: 4

Ser Gln Ser Gly Ser Arg Asn
1               5

<210> SEQ ID NO 5
<211> LENGTH: 3
<212> TYPE: PRT
<213> ORGANISM: Artificial Sequence
<220> FEATURE:
<223> OTHER INFORMATION: Chemically Synthesized, C22B21 CD22 arm LCDR2

<400> SEQUENCE: 5

Gly Ala Ser
1

<210> SEQ ID NO 6
<211> LENGTH: 6
<212> TYPE: PRT
<213> ORGANISM: Artificial Sequence
<220> FEATURE:
<223> OTHER INFORMATION: Chemically Synthesized, C22B21 CD22 arm LCDR3

<400> SEQUENCE: 6

Tyr Asn Asn Trp Pro Leu
1               5

<210> SEQ ID NO 7
<211> LENGTH: 122
<212> TYPE: PRT
<213> ORGANISM: Artificial Sequence
<220> FEATURE:
<223> OTHER INFORMATION: Chemically Synthesized, C22B21 CD22 arm VH

<400> SEQUENCE: 7

Gln Val Thr Leu Arg Glu Ser Gly Pro Ala Leu Val Lys Pro Thr Gln
1               5                   10                  15

Thr Leu Thr Leu Thr Cys Thr Leu Ser Gly Leu Pro Leu Ser Thr Ser
            20                  25                  30

Gly Met Ala Val Thr Trp Ile Arg Gln Pro Pro Gly Lys Ala Leu Glu
        35                  40                  45

Trp Leu Ala Leu Ile Asp Trp Asp Asp Asp Lys Tyr Tyr Ser Thr Ser
    50                  55                  60
```

```
Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Met Gly Tyr Ser Tyr Gly Trp Asp Ala Phe Asp Leu Trp
            100                 105                 110

Gly Gln Gly Thr Met Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: Chemically Synthesized, C22B21 CD22 arm VL

<400> SEQUENCE: 8

Glu Val Val Met Thr Gln Ser Pro Ala Thr Leu Ser Val Ser Pro Gly
1               5                   10                  15

Glu Gly Ala Thr Leu Ser Cys Arg Ala Ser Gln Ser Gly Ser Arg Asn
            20                  25                  30

Ile Ala Trp Tyr Gln Gln Lys Pro Gly Gln Ala Pro Arg Leu Leu Ile
        35                  40                  45

Phe Gly Ala Ser Ala Arg Ala Thr Gly Ile Pro Ala Arg Phe Thr Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Leu
                 85                  90                  95

Thr Phe Gly Gly Gly Thr Lys Val Glu Ile Lys
            100                 105

<210> SEQ ID NO 9
<211> LENGTH: 7
<212> TYPE: PRT
<213> ORGANISM: Artificial Sequence
<220> FEATURE:
<223> OTHER INFORMATION: Chemically Synthesized, CD9B337 CD79b arm HCDR1

<400> SEQUENCE: 9

Gly Phe Thr Leu Arg Asn Tyr
1               5

<210> SEQ ID NO 10
<211> LENGTH: 6
<212> TYPE: PRT
<213> ORGANISM: Artificial Sequence
<220> FEATURE:
<223> OTHER INFORMATION: Chemically Synthesized, CD9B337 CD79b arm HCDR2

<400> SEQUENCE: 10

Asn Gln Asp Gly Ser Glu
1               5

<210> SEQ ID NO 11
<211> LENGTH: 8
<212> TYPE: PRT
<213> ORGANISM: Artificial Sequence
<220> FEATURE:
<223> OTHER INFORMATION: Chemically Synthesized, CD9B337 CD79b arm HCDR3

<400> SEQUENCE: 11
```

```
Asp Pro Ile Glu Ser Arg Phe Asp
1               5
```

<210> SEQ ID NO 12
<211> LENGTH: 12
<212> TYPE: PRT
<213> ORGANISM: Artificial Sequence
<220> FEATURE:
<223> OTHER INFORMATION: Chemically Synthesized, CD9B337 CD79b arm LCDR1

<400> SEQUENCE: 12

```
Ser Gln Ser Leu Val Tyr Ser Asp Gly Asn Thr Tyr
1               5                   10
```

<210> SEQ ID NO 13
<211> LENGTH: 3
<212> TYPE: PRT
<213> ORGANISM: Artificial Sequence
<220> FEATURE:
<223> OTHER INFORMATION: Chemically Synthesized, CD9B337 CD79b arm LCDR2

<400> SEQUENCE: 13

```
Lys Val Ser
1
```

<210> SEQ ID NO 14
<211> LENGTH: 6
<212> TYPE: PRT
<213> ORGANISM: Artificial Sequence
<220> FEATURE:
<223> OTHER INFORMATION: Chemically Synthesized, CD9B337 CD79b arm LCDR3

<400> SEQUENCE: 14

```
Gly Thr His Trp Pro Pro
1               5
```

<210> SEQ ID NO 15
<211> LENGTH: 118
<212> TYPE: PRT
<213> ORGANISM: Artificial Sequence
<220> FEATURE:
<223> OTHER INFORMATION: Chemically Synthesized, CD9B337 CD79b arm VH

<400> SEQUENCE: 15

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Arg Asn Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Glu Gly Arg Phe Thr Ile Ser Arg Asp Asn Ala Lys Lys Ser Leu Trp
65                  70                  75                  80

Leu Gln Met Ser Ser Leu Arg Val Glu Asp Thr Ala Val Tyr Tyr Cys
                85                  90                  95

Ala Arg Asp Pro Ile Glu Ser Arg Phe Asp Tyr Trp Gly Gln Gly Thr
            100                 105                 110

Leu Val Thr Val Ser Ser
        115
```

<210> SEQ ID NO 16
<211> LENGTH: 112

```
<212> TYPE: PRT
<213> ORGANISM: Artificial Sequence
<220> FEATURE:
<223> OTHER INFORMATION: Chemically Synthesized, CD9B337 CD79b arm VL

<400> SEQUENCE: 16

Asp Val Val Met Thr Gln Ser Pro Leu Ser Leu Pro Val Thr Leu Gly
1               5                   10                  15

Gln Pro Ala Ser Ile Ser Cys Arg Ser Gln Ser Leu Val Tyr Ser
            20                  25                  30

Asp Gly Asn Thr Tyr Leu Ser Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gly Thr Lys Val Glu Ile Lys
            100                 105                 110

<210> SEQ ID NO 17
<211> LENGTH: 10
<212> TYPE: PRT
<213> ORGANISM: Artificial Sequence
<220> FEATURE:
<223> OTHER INFORMATION: Chemically Synthesized, CD9B374 CD79b arm HCDR1

<400> SEQUENCE: 17

Gly Ala Ser Ile Ser Ser Phe Tyr Trp Ser
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Chemically Synthesized, CD9B374 CD79b arm HCDR2

<400> SEQUENCE: 18

Arg Ile Ser Pro Ser Gly Lys Thr Asn
1               5

<210> SEQ ID NO 19
<211> LENGTH: 13
<212> TYPE: PRT
<213> ORGANISM: Artificial Sequence
<220> FEATURE:
<223> OTHER INFORMATION: Chemically Synthesized, CD9B374 CD79b arm HCDR3

<400> SEQUENCE: 19

Gly Glu Tyr Ser Gly Thr Tyr Ser Tyr Ser Phe Asp Val
1               5                   10

<210> SEQ ID NO 20
<211> LENGTH: 17
<212> TYPE: PRT
<213> ORGANISM: Artificial Sequence
<220> FEATURE:
<223> OTHER INFORMATION: Chemically Synthesized, CD9B374 CD79b arm LCDR1

<400> SEQUENCE: 20

Arg Ser Ser Glu Ser Leu Leu Asp Ser Glu Asp Gly Asn Thr Tyr Leu
1               5                   10                  15
```

Asp

<210> SEQ ID NO 21
<211> LENGTH: 7
<212> TYPE: PRT
<213> ORGANISM: Artificial Sequence
<220> FEATURE:
<223> OTHER INFORMATION: Chemically Synthesized, CD9B374 CD79b arm LCDR2

<400> SEQUENCE: 21

```
Thr Leu Ser Tyr Arg Ala Ser
1               5
```

<210> SEQ ID NO 22
<211> LENGTH: 9
<212> TYPE: PRT
<213> ORGANISM: Artificial Sequence
<220> FEATURE:
<223> OTHER INFORMATION: Chemically Synthesized, CD9B374 CD79b arm LCDR3

<400> SEQUENCE: 22

```
Met Gln Arg Met Glu Phe Pro Leu Thr
1               5
```

<210> SEQ ID NO 23
<211> LENGTH: 121
<212> TYPE: PRT
<213> ORGANISM: Artificial Sequence
<220> FEATURE:
<223> OTHER INFORMATION: Chemically Synthesized, CD9B374 CD79b arm VH

<400> SEQUENCE: 23

```
Gln Val Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Ser Phe
            20                  25                  30

Tyr Trp Ser Trp Ile Arg Gln Pro Ala Asp Gly Leu Glu Trp Ile
        35                  40                  45

Gly Arg Ile Ser Pro Ser Gly Lys Thr Asn Tyr Ile Pro Ser Leu Lys
    50                  55                  60

Ser Arg Ile Ile Met Ser Leu Asp Ala Ser Lys Asn Gln Phe Ser Leu
65                  70                  75                  80

Arg Leu Asn Ser Val Thr Ala Ala Asp Thr Ala Met Tyr Tyr Cys Ala
                85                  90                  95

Arg Gly Glu Tyr Ser Gly Thr Tyr Ser Tyr Ser Phe Asp Val Trp Gly
            100                 105                 110

Gln Gly Thr Met Val Thr Val Ser Ser
        115                 120
```

<210> SEQ ID NO 24
<211> LENGTH: 113
<212> TYPE: PRT
<213> ORGANISM: Artificial Sequence
<220> FEATURE:
<223> OTHER INFORMATION: Chemically Synthesized, CD9B374 CD79b arm VL

<400> SEQUENCE: 24

```
Asp Ile Val Met Thr Gln Ser Pro Leu Ser Leu Ser Val Thr Pro Gly
1               5                   10                  15

Glu Pro Ala Ser Ile Ser Cys Arg Ser Ser Glu Ser Leu Leu Asp Ser
            20                  25                  30
```

Glu Asp Gly Asn Thr Tyr Leu Asp Trp Phe Leu Gln Lys Pro Gly Gln
            35                  40                  45

Ser Pro Gln Leu Leu Ile Tyr Thr Leu Ser Tyr Arg Ala Ser Gly Val
 50                  55                  60

Pro Asp Arg Phe Ser Gly Ser Gly Ser Asp Thr Asp Phe Thr Leu His
 65                  70                  75                  80

Ile Ser Ser Leu Glu Ala Glu Asp Val Gly Leu Tyr Tyr Cys Met Gln
                 85                  90                  95

Arg Met Glu Phe Pro Leu Thr Phe Gly Gln Gly Thr Lys Val Glu Ile
            100                 105                 110

Lys

<210> SEQ ID NO 25
<211> LENGTH: 12
<212> TYPE: PRT
<213> ORGANISM: Artificial Sequence
<220> FEATURE:
<223> OTHER INFORMATION: Chemically Synthesized, CD9B330 CD79b arm HCDR1

<400> SEQUENCE: 25

Gly Asp Ser Val Ser Asn Asn Ser Ala Thr Trp Asn
 1               5                  10

<210> SEQ ID NO 26
<211> LENGTH: 11
<212> TYPE: PRT
<213> ORGANISM: Artificial Sequence
<220> FEATURE:
<223> OTHER INFORMATION: Chemically Synthesized, CD9B330 CD79b arm HCDR2

<400> SEQUENCE: 26

Arg Thr Tyr Tyr Arg Ser Lys Trp Tyr Asn Asp
 1               5                  10

<210> SEQ ID NO 27
<211> LENGTH: 7
<212> TYPE: PRT
<213> ORGANISM: Artificial Sequence
<220> FEATURE:
<223> OTHER INFORMATION: Chemically Synthesized, CD9B330 CD79b arm HCDR3

<400> SEQUENCE: 27

Val Asp Ile Ala Phe Asp Tyr
 1               5

<210> SEQ ID NO 28
<211> LENGTH: 13
<212> TYPE: PRT
<213> ORGANISM: Artificial Sequence
<220> FEATURE:
<223> OTHER INFORMATION: Chemically Synthesized, CD9B330 CD79b arm LCDR1

<400> SEQUENCE: 28

Ser Gly Ser Ser Ser Asn Ile Gly Asn His Gly Val Asn
 1               5                  10

<210> SEQ ID NO 29
<211> LENGTH: 7
<212> TYPE: PRT
<213> ORGANISM: Artificial Sequence
<220> FEATURE:
<223> OTHER INFORMATION: Chemically Synthesized, CD9B330 CD79b arm LCDR2

<400> SEQUENCE: 29

```
Asn Asp Asp Leu Leu Pro Ser
1               5
```

<210> SEQ ID NO 30
<211> LENGTH: 11
<212> TYPE: PRT
<213> ORGANISM: Artificial Sequence
<220> FEATURE:
<223> OTHER INFORMATION: Chemically Synthesized, CD9B330 CD79b arm LCDR3

<400> SEQUENCE: 30

```
Ala Ala Trp Asp Asp Ser Leu Asn Gly Val Val
1               5                   10
```

<210> SEQ ID NO 31
<211> LENGTH: 119
<212> TYPE: PRT
<213> ORGANISM: Artificial Sequence
<220> FEATURE:
<223> OTHER INFORMATION: Chemically Synthesized, CD9B330 CD79b arm VH

<400> SEQUENCE: 31

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Asn Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Thr
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Thr Arg Val Asp Ile Ala Phe Asp Tyr Trp Gly Gln Gly
            100                 105                 110

Thr Leu Val Thr Val Ser Ser
        115
```

<210> SEQ ID NO 32
<211> LENGTH: 110
<212> TYPE: PRT
<213> ORGANISM: Artificial Sequence
<220> FEATURE:
<223> OTHER INFORMATION: Chemically Synthesized, CD9B330 CD79b arm VL

<400> SEQUENCE: 32

```
Gln Thr Val Val Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn His
            20                  25                  30

Gly Val Asn Trp Tyr Gln Gln Leu Pro Gly Lys Ala Pro Lys Leu Leu
        35                  40                  45

Ile Tyr Asn Asp Asp Leu Leu Pro Ser Gly Val Ser Asp Arg Phe Ser
    50                  55                  60

Gly Ser Thr Ser Gly Thr Ser Gly Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
```

<210> SEQ ID NO 33
<211> LENGTH: 10
<212> TYPE: PRT
<213> ORGANISM: Artificial Sequence
<220> FEATURE:
<223> OTHER INFORMATION: Chemically Synthesized, CD9B643 CD79b arm HCDR1

<400> SEQUENCE: 33

Gly Val Ser Ile Ser Asn Tyr Tyr Trp Ser
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Chemically Synthesized, CD9B643 CD79b arm HCDR2

<400> SEQUENCE: 34

Arg Ile Ser Pro Ser Gly Arg Thr Asn
1               5

<210> SEQ ID NO 35
<211> LENGTH: 13
<212> TYPE: PRT
<213> ORGANISM: Artificial Sequence
<220> FEATURE:
<223> OTHER INFORMATION: Chemically Synthesized, CD9B643 CD79b arm HCDR3

<400> SEQUENCE: 35

Gly Glu Tyr Ser Gly Thr Tyr Ser Tyr Ser Phe Asp Ile
1               5                   10

<210> SEQ ID NO 36
<211> LENGTH: 17
<212> TYPE: PRT
<213> ORGANISM: Artificial Sequence
<220> FEATURE:
<223> OTHER INFORMATION: Chemically Synthesized, CD9B643 CD79b arm LCDR1

<400> SEQUENCE: 36

Arg Ser Ser Gln Ser Leu Phe Asp Ser Asp Asp Gly Asn Thr Tyr Leu
1               5                   10                  15

Asp

<210> SEQ ID NO 37
<211> LENGTH: 7
<212> TYPE: PRT
<213> ORGANISM: Artificial Sequence
<220> FEATURE:
<223> OTHER INFORMATION: Chemically Synthesized, CD9B643 CD79b arm LCDR2

<400> SEQUENCE: 37

Thr Leu Ser Tyr Arg Ala Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Chemically Synthesized, CD9B643 CD79b arm LCDR3

<400> SEQUENCE: 38

Met Gln Arg Met Glu Phe Pro Leu Thr
1               5

<210> SEQ ID NO 39
<211> LENGTH: 121
<212> TYPE: PRT
<213> ORGANISM: Artificial Sequence
<220> FEATURE:
<223> OTHER INFORMATION: Chemically Synthesized, CD9B643 CD79b arm VH

<400> SEQUENCE: 39

Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Ile Ser Asn Tyr
            20                  25                  30

Tyr Trp Ser Trp Ile Arg Gln Pro Pro Gly Lys Gly Leu Glu Trp Ile
        35                  40                  45

Gly Arg Ile Ser Pro Ser Gly Arg Thr Asn Tyr Asn Pro Ser Leu Lys
    50                  55                  60

Ser Arg Val Thr Met Ser Leu Asp Ala Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Glu Tyr Ser Gly Thr Tyr Ser Tyr Ser Phe Asp Ile Trp Gly
            100                 105                 110

Gln Gly Thr Met Val Thr Val Ser Ser
        115                 120

<210> SEQ ID NO 40
<211> LENGTH: 113
<212> TYPE: PRT
<213> ORGANISM: Artificial Sequence
<220> FEATURE:
<223> OTHER INFORMATION: Chemically Synthesized, CD9B643 CD79b arm VL

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Phe Asp Ser
            20                  25                  30

Asp Asp Gly Asn Thr Tyr Leu Asp Trp Phe Gln Gln Lys Pro Gly Gln
        35                  40                  45

Ser Pro Lys Leu Leu Ile Gln Thr Leu Ser Tyr Arg Ala Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Met Gln
                85                  90                  95

Arg Met Glu Phe Pro Leu Thr Phe Gly Gly Gly Thr Lys Val Glu Ile
            100                 105                 110

Lys

<210> SEQ ID NO 41
<211> LENGTH: 12
<212> TYPE: PRT
<213> ORGANISM: Artificial Sequence
<220> FEATURE:
<223> OTHER INFORMATION: Chemically Synthesized, CD9B324 CD79b arm HCDR1

<400> SEQUENCE: 41

```
Gly Asp Ser Val Ser Asn Asn Ser Ala Thr Trp Asn
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Chemically Synthesized, CD9B324 CD79b arm HCDR2

<400> SEQUENCE: 42

Arg Thr Tyr Tyr Arg Ser Lys Trp Tyr Asn Asp
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Chemically Synthesized, CD9B324 CD79b arm HCDR3

<400> SEQUENCE: 43

Val Asp Ile Ala Phe Asp Tyr
1               5

<210> SEQ ID NO 44
<211> LENGTH: 13
<212> TYPE: PRT
<213> ORGANISM: Artificial Sequence
<220> FEATURE:
<223> OTHER INFORMATION: Chemically Synthesized, CD9B324 CD79b arm LCDR1

<400> SEQUENCE: 44

Ser Gly Ser Ser Ser Asn Ile Gly Asn His Gly Val Asn
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Chemically Synthesized, CD9B324 CD79b arm LCDR2

<400> SEQUENCE: 45

Asn Asp Asp Leu Leu Pro Ser
1               5

<210> SEQ ID NO 46
<211> LENGTH: 11
<212> TYPE: PRT
<213> ORGANISM: Artificial Sequence
<220> FEATURE:
<223> OTHER INFORMATION: Chemically Synthesized, CD9B324 CD79b arm LCDR3

<400> SEQUENCE: 46

Ala Ala Trp Asp Asp Ser Leu Asn Gly Val Val
1               5                   10

<210> SEQ ID NO 47
<211> LENGTH: 119
<212> TYPE: PRT
<213> ORGANISM: Artificial Sequence
<220> FEATURE:
<223> OTHER INFORMATION: Chemically Synthesized, CD9B324 CD79b arm VH

<400> SEQUENCE: 47
```

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Asn Asn
            20                  25                  30

Ser Ala Thr Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Thr
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Thr Arg Val Asp Ile Ala Phe Asp Tyr Trp Gly Gln Gly
            100                 105                 110

Thr Leu Val Thr Val Ser Ser
            115

<210> SEQ ID NO 48
<211> LENGTH: 110
<212> TYPE: PRT
<213> ORGANISM: Artificial Sequence
<220> FEATURE:
<223> OTHER INFORMATION: Chemically Synthesized, CD9B324 CD79b arm VL

<400> SEQUENCE: 48

Gln Leu Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn His
            20                  25                  30

Gly Val Asn Trp Tyr Gln Gln Leu Pro Gly Lys Ala Pro Lys Leu Leu
            35                  40                  45

Ile Tyr Asn Asp Asp Leu Leu Pro Ser Gly Val Ser Asp Arg Phe Ser
    50                  55                  60

Gly Ser Thr Ser Gly Thr Ser Gly Ser Leu Ala Ile Ser Gly Leu Gln
65                  70                  75                  80

Ser Glu Asp Glu Ala Asp Tyr Tyr Cys Ala Ala Trp Asp Asp Ser Leu
            85                  90                  95

Asn Gly Val Val Phe Gly Gly Gly Thr Lys Leu Thr Val Leu
            100                 105                 110

<210> SEQ ID NO 49
<211> LENGTH: 10
<212> TYPE: PRT
<213> ORGANISM: Artificial Sequence
<220> FEATURE:
<223> OTHER INFORMATION: Chemically Synthesized, CD9B389 CD79b arm HCDR1

<400> SEQUENCE: 49

Gly Val Ser Ile Ser Asn Tyr Tyr Trp Ser
1               5                   10

<210> SEQ ID NO 50
<211> LENGTH: 9
<212> TYPE: PRT
<213> ORGANISM: Artificial Sequence
<220> FEATURE:
<223> OTHER INFORMATION: Chemically Synthesized, CD9B389 CD79b arm HCDR2

<400> SEQUENCE: 50

Arg Ile Ser Pro Ser Gly Arg Thr Asn

```
<210> SEQ ID NO 51
<211> LENGTH: 13
<212> TYPE: PRT
<213> ORGANISM: Artificial Sequence
<220> FEATURE:
<223> OTHER INFORMATION: Chemically Synthesized, CD9B389 CD79b arm HCDR3

<400> SEQUENCE: 51

Gly Glu Tyr Ser Gly Thr Tyr Ser Tyr Ser Phe Asp Ile
1               5                   10

<210> SEQ ID NO 52
<211> LENGTH: 17
<212> TYPE: PRT
<213> ORGANISM: Artificial Sequence
<220> FEATURE:
<223> OTHER INFORMATION: Chemically Synthesized, CD9B389 CD79b arm LCDR1

<400> SEQUENCE: 52

Arg Ser Ser Gln Ser Leu Phe Asp Ser Asp Asp Gly Asn Thr Tyr Leu
1               5                   10                  15

Asp

<210> SEQ ID NO 53
<211> LENGTH: 7
<212> TYPE: PRT
<213> ORGANISM: Artificial Sequence
<220> FEATURE:
<223> OTHER INFORMATION: Chemically Synthesized, CD9B389 CD79b arm LCDR2

<400> SEQUENCE: 53

Thr Leu Ser Tyr Arg Ala Ser
1               5

<210> SEQ ID NO 54
<211> LENGTH: 9
<212> TYPE: PRT
<213> ORGANISM: Artificial Sequence
<220> FEATURE:
<223> OTHER INFORMATION: Chemically Synthesized, CD9B389 CD79b arm LCDR3

<400> SEQUENCE: 54

Met Gln Arg Met Glu Phe Pro Leu Thr
1               5

<210> SEQ ID NO 55
<211> LENGTH: 121
<212> TYPE: PRT
<213> ORGANISM: Artificial Sequence
<220> FEATURE:
<223> OTHER INFORMATION: Chemically Synthesized, CD9B389 CD79b arm VH

<400> SEQUENCE: 55

Gln Val Gln Leu Gln Gln Ser Gly Pro Gly Leu Val Arg Pro Ser Glu
1               5                   10                  15

Thr Leu Ala Leu Thr Cys Ser Val Ser Gly Val Ser Ile Ser Asn Tyr
            20                  25                  30

Tyr Trp Ser Trp Ile Arg Gln Pro Ala Gly Arg Gly Leu Glu Trp Ile
        35                  40                  45

Gly Arg Ile Ser Pro Ser Gly Arg Thr Asn Tyr Asn Thr Ser Leu Lys
    50                  55                  60

Ser Arg Gly Thr Met Ser Leu Asp Ala Ser Lys Asn Gln Phe Ser Leu
```

65                  70                  75                  80
Lys Val Asn Ser Val Thr Ala Ala Asp Thr Ala Val Tyr Tyr Cys Ala
                        85                  90                  95

Arg Gly Glu Tyr Ser Gly Thr Tyr Ser Tyr Ser Phe Asp Ile Trp Gly
                100                 105                 110

Gln Gly Thr Met Val Thr Val Ser Ser
            115                 120

<210> SEQ ID NO 56
<211> LENGTH: 113
<212> TYPE: PRT
<213> ORGANISM: Artificial Sequence
<220> FEATURE:
<223> OTHER INFORMATION: Chemically Synthesized, CD9B389 CD79b arm VL

<400> SEQUENCE: 56

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Phe Asp Ser
                20                  25                  30

Asp Asp Gly Asn Thr Tyr Leu Asp Trp Phe Leu Gln Lys Pro Gly Gln
            35                  40                  45

Ser Pro Gln Leu Leu Ile Gln Thr Leu Ser Tyr Arg Ala Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Glu Ala Asp Asp Val Gly Val Tyr Tyr Cys Met Gln
                85                  90                  95

Arg Met Glu Phe Pro Leu Thr Phe Gly Gly Gly Thr Lys Leu Glu Ile
                100                 105                 110

Lys

<210> SEQ ID NO 57
<211> LENGTH: 10
<212> TYPE: PRT
<213> ORGANISM: Artificial Sequence
<220> FEATURE:
<223> OTHER INFORMATION: Chemically Synthesized, CD9B390 CD79b arm HCDR1

<400> SEQUENCE: 57

Gly Gly Ser Ile Ser Asn Tyr Tyr Trp Ser
1               5                   10

<210> SEQ ID NO 58
<211> LENGTH: 9
<212> TYPE: PRT
<213> ORGANISM: Artificial Sequence
<220> FEATURE:
<223> OTHER INFORMATION: Chemically Synthesized, CD9B390 CD79b arm HCDR2

<400> SEQUENCE: 58

Arg Ile Phe Tyr Ser Gly Lys Thr Asn
1               5

<210> SEQ ID NO 59
<211> LENGTH: 13
<212> TYPE: PRT
<213> ORGANISM: Artificial Sequence
<220> FEATURE:
<223> OTHER INFORMATION: Chemically Synthesized, CD9B390 CD79b arm HCDR3

<400> SEQUENCE: 59

```
Gly Glu Tyr Ser Gly Glu Tyr Ser Tyr Ser Phe Asp Ile
1               5                   10
```

<210> SEQ ID NO 60
<211> LENGTH: 17
<212> TYPE: PRT
<213> ORGANISM: Artificial Sequence
<220> FEATURE:
<223> OTHER INFORMATION: Chemically Synthesized, CD9B390 CD79b arm LCDR1

<400> SEQUENCE: 60

```
Arg Ser Ser Gln Ser Leu Leu Asp Ser Asp Gly Asn Thr Tyr Val
1               5                   10                  15
Asp
```

<210> SEQ ID NO 61
<211> LENGTH: 7
<212> TYPE: PRT
<213> ORGANISM: Artificial Sequence
<220> FEATURE:
<223> OTHER INFORMATION: Chemically Synthesized, CD9B390 CD79b arm LCDR2

<400> SEQUENCE: 61

```
Thr Leu Ser Tyr Arg Ala Ser
1               5
```

<210> SEQ ID NO 62
<211> LENGTH: 9
<212> TYPE: PRT
<213> ORGANISM: Artificial Sequence
<220> FEATURE:
<223> OTHER INFORMATION: Chemically Synthesized, CD9B390 CD79b arm LCDR3

<400> SEQUENCE: 62

```
Met Gln Arg Met Glu Phe Pro Leu Thr
1               5
```

<210> SEQ ID NO 63
<211> LENGTH: 121
<212> TYPE: PRT
<213> ORGANISM: Artificial Sequence
<220> FEATURE:
<223> OTHER INFORMATION: Chemically Synthesized, CD9B390 CD79b arm VH

<400> SEQUENCE: 63

```
Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Ser Asn Tyr
            20                  25                  30

Tyr Trp Ser Trp Ile Arg Gln Pro Ala Gly Lys Gly Leu Glu Trp Ile
        35                  40                  45

Gly Arg Ile Phe Tyr Ser Gly Lys Thr Asn Tyr Asn Ser Ser Leu Lys
    50                  55                  60

Ser Arg Val Thr Met Ser Ala Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Glu Tyr Ser Gly Glu Tyr Ser Tyr Ser Phe Asp Ile Trp Gly
            100                 105                 110

Gln Gly Thr Thr Val Thr Val Ser Ser
        115                 120
```

<210> SEQ ID NO 64
<211> LENGTH: 113
<212> TYPE: PRT
<213> ORGANISM: Artificial Sequence
<220> FEATURE:
<223> OTHER INFORMATION: Chemically Synthesized, CD9B390 CD79b arm VL

<400> SEQUENCE: 64

```
Glu Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Val Asp Trp Phe Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Asp Thr Asp Phe Thr Leu Lys
65                  70                  75                  80

Ile Ser Arg Val Glu Ala Glu Asp Val Gly Ile Tyr Tyr Cys Met Gln
                85                  90                  95

Arg Met Glu Phe Pro Leu Thr Phe Gly Gly Gly Thr Lys Val Glu Ile
            100                 105                 110

Lys
```

<210> SEQ ID NO 65
<211> LENGTH: 363
<212> TYPE: DNA
<213> ORGANISM: Artificial Sequence
<220> FEATURE:
<223> OTHER INFORMATION: Chemically Synthesized, CD9B374 VH

<400> SEQUENCE: 65

```
caggttcagc tgcaagagtc tggtcctggc ctggtcaagc cttccgagac actgtctctg     60
acctgctctg tgtccggcgc ctccatctct tccttctact ggtcctggat ccggcagcct    120
gctgacgaag gactggaatg gatcggccgg atcagccctt ctgcaagac  caactacatc    180 cccagcctga agtcccggat catcatgtcc ctggacgcct ccaagaacca gttctccctg    240
cggctgaact ctgtgaccgc tgccgatacc gccatgtact actgtgccag aggcgagtac    300
tccggcacct actcctacag ctttgacgtg tggggacaag gcaccatggt cacagtttct    360
tct                                                                 363
```

<210> SEQ ID NO 66
<211> LENGTH: 339
<212> TYPE: DNA
<213> ORGANISM: Artificial Sequence
<220> FEATURE:
<223> OTHER INFORMATION: Chemically Synthesized, CD9B374 VL

<400> SEQUENCE: 66

```
gacatcgtga tgacccagtc tccactgagc ctgtctgtga cacctggcga gcctgcctcc     60
atctcctgta gatcttctga gtccctgctg gacagcgagg acggcaatac ctacctggac    120
tggttcctgc agaagcccgg acagtctcct cagctgctga tctacaccct gtcctacaga    180
gcctctggcg tgcccgatag attctccggc tctggctctg acaccgactt taccctgcac    240
atctccagcc tggaagccga ggatgtgggc ctgtactact gtatgcagcg gatggaattt    300 ccccctgacct tcggccaggg caccaaggtg gaaatcaag                          339
```

<210> SEQ ID NO 67
<211> LENGTH: 339
<212> TYPE: DNA
<213> ORGANISM: Artificial Sequence
<220> FEATURE:
<223> OTHER INFORMATION: Chemically Synthesized, CD9B374 VL

<400> SEQUENCE: 67

| gatattgtga tgactcagtc tccactctcc ctgtccgtca cccctggaga gccggcctcc | 60 |
| atctcctgca ggtctagtga gagcctcttg gatagtgaag atggaaacac ctatttggac | 120 |
| tggttcctgc agaagccagg gcagtctcct cagctcctga tctatacgct ttcctatcgg | 180 |
| gcctctggag tcccagacag gttcagtggc agtgggtcgg acactgattt cacactgcac | 240 |
| atcagcagtc tggaggctga ggatgttgga ctttattact gcatgcaacg tatggagttt | 300 |
| ccgctcactt tcggccaagg gaccaaggtg gaaatcaaa | 339 |

<210> SEQ ID NO 68
<211> LENGTH: 357
<212> TYPE: DNA
<213> ORGANISM: Artificial Sequence
<220> FEATURE:
<223> OTHER INFORMATION: Chemically Synthesized, CD9B330 VH

<400> SEQUENCE: 68

| caagtgcaac tgcagcagtc tggccctgga ctggtcaagc cttctcagac cctgtctctg | 60 |
| acctgcgcca tctccggcga ctccgtgtcc aacaactccg ctacctggaa ctggatcaga | 120 |
| cagtccccktt ccagaggcct ggaatggctg ggcagaacct actaccggtc caagtggtac | 180 |
| aacgactaca ccgtgtccgt gaagtcccgg atcaccatca accctgatac ctctaagaac | 240 |
| cagttctccc tgcaactgaa ctctgtgacc cctgaggaca ccgccgtgta ctactgcacc | 300 |
| agagtggaca tcgccttcga ctactggggc cagggcaccc tggtgaccgt gtctagc | 357 |

<210> SEQ ID NO 69
<211> LENGTH: 330
<212> TYPE: DNA
<213> ORGANISM: Artificial Sequence
<220> FEATURE:
<223> OTHER INFORMATION: Chemically Synthesized, CD9B330 VL

<400> SEQUENCE: 69

| cagactgtgg tgactcagcc accctcggtg tctgaagccc ccaggcagag ggtcaccatc | 60 |
| tcctgttctg gaagtagctc caacatcgga aatcatggtg taaactggta ccagcagctc | 120 |
| ccaggaaagg ctcccaaact cctcatctat aatgatgatc tgctgccctc agggctctct | 180 |
| gaccgattct ctggctccac gtctggcacc tcaggttccc tggccatcag tgggctccag | 240 |
| tctgaggatg aggctgatta ttactgtgca gcatgggatg acagcctgaa tggtgtggta | 300 |
| ttcggcggag ggactaaact gaccgtccta | 330 |

<210> SEQ ID NO 70
<211> LENGTH: 363
<212> TYPE: DNA
<213> ORGANISM: Artificial Sequence
<220> FEATURE:
<223> OTHER INFORMATION: Chemically Synthesized, CD9B643 VH

<400> SEQUENCE: 70

| caggttcagc tgcaagagtc tggccctggc ctggtcaagc cctctcagac cctgtctctg | 60 |
| acctgtaccg tgtccggcgt gtccatctcc aactactact ggtcctggat ccggcagcct | 120 |

```
cctggcaaag gactggaatg gatcggccgc atctctcctt ctggtcgcac caactacaac    180
cccagcctga aaagcagagt gaccatgtct ctggacgcct ccaagaacca gttctccctg    240
aagctgtcct ccgtgaccgc tgctgatacc gccgtgtact actgtgccag aggcgagtac    300
tccggcacct actcctacag cttcgacatc tggggccagg gcaccatggt cacagtctct    360
tct                                                                  363

<210> SEQ ID NO 71
<211> LENGTH: 339
<212> TYPE: DNA
<213> ORGANISM: Artificial Sequence
<220> FEATURE:
<223> OTHER INFORMATION: Chemically Synthesized, CD9B643 VL

<400> SEQUENCE: 71
gacatccaga tgacccagtc tccatcctct ctgtccgcct ctgtgggcga cagagtgacc     60
atcacctgtc ggtcctctca gtccctgttc gactctgacg acggcaacac ctacctggac    120
tggttccagc agaagcccgg ccagtctcct aagctgctga tccagacact gtcctacaga    180
gcctctggcg tgccctccag attttccggc tctggctctg gcaccgactt taccctgaca    240
atctccagcc tgcagcctga ggacttcgcc acctactact gtatgcagcg gatggaattt    300
cccctgacct cggcggagg caccaaggtg gaaatcaag                            339

<210> SEQ ID NO 72
<211> LENGTH: 339
<212> TYPE: DNA
<213> ORGANISM: Artificial Sequence
<220> FEATURE:
<223> OTHER INFORMATION: Chemically Synthesized, CD9B643 VL

<400> SEQUENCE: 72
gacatccaga tgacccagag ccctagcagc ctgagcgcca gcgtgggcga cagagtgacc     60
attacctgca gaagcagcca gagcctgttc gacagcgacg acggcaatac ctacctggac    120
tggttccagc agaagcctgg ccagagccct aagctgctga tccagaccct gagctacaga    180
gccagcggcg tgcctagcag attctccggc agcggctccg gcaccgactt caccctgacc    240
atcagcagcc tgcagcctga ggacttcgcc acctactact gcatgcagag aatggagttc    300
cctctgacct cggcggcgg caccaaggtg gagatcaag                            339

<210> SEQ ID NO 73
<211> LENGTH: 357
<212> TYPE: DNA
<213> ORGANISM: Artificial Sequence
<220> FEATURE:
<223> OTHER INFORMATION: Chemically Synthesized, CD9B324 VH

<400> SEQUENCE: 73
caagtgcaac tgcagcagtc tggccctgga ctggtcaagc cttctcagac cctgtctctg     60
acctgcgcca tctccggcga ctccgtgtcc aacaactccg ctacctggaa ctggatcaga    120
cagtccccct tccagaggcc tggaatggct ggcagaacct actaccggtc caagtggtac    180
aacgactaca ccgtgtccgt gaagtcccgg atcaccatca accctgatac ctctaagaac    240
cagttctccc tgcaactgaa ctctgtgacc cctgaggaca ccgccgtgta ctactgcacc    300
agagtggaca cgccttcga ctactgggc cagggcaccc tggtgaccgt gtctagc         357

<210> SEQ ID NO 74
```

```
<211> LENGTH: 330
<212> TYPE: DNA
<213> ORGANISM: Artificial Sequence
<220> FEATURE:
<223> OTHER INFORMATION: Chemically Synthesized, CD9B324 VL

<400> SEQUENCE: 74
cagcttgtgc tgactcagcc accctcggtg tctgaagccc caggcagag  ggtcaccatc    60 tcctgttctg gaagtagctc aacatcgga  aatcatggtg taaactggta ccagcagctc   120
ccaggaaagg ctcccaaact cctcatctat aatgatgatc tgctgccctc aggggtctct   180
gaccgattct ctggctccac gtctggcacc tcaggttccc tggccatcag tgggctccag   240
tctgaggatg aggctgatta ttactgtgca gcatgggatg acagcctgaa tggtgtggta   300
ttcggcggag ggactaaact gaccgtccta                                    330

<210> SEQ ID NO 75
<211> LENGTH: 363
<212> TYPE: DNA
<213> ORGANISM: Artificial Sequence
<220> FEATURE:
<223> OTHER INFORMATION: Chemically Synthesized, CD9B389 VH

<400> SEQUENCE: 75
caagttcagc ttcaacaatc tggtccaggt ctcgtaagac catcagaaac attggctctt    60
acatgctctg ttagtggtgt gtcaatcagt aactattact ggtcctggat ccgccaacct   120
gctggccgtg ggctcgaatg gatcggacga atctcaccta gcggtaggac aaattacaac   180
acttccctta aatcacgagg acaatgagc  ctcgacgcat caaagaacca gttcagcctt   240 aaagtaaaact ccgttaccgc agcagatact gcagtctact attgtgccag gggtgaatat   300
tcaggaacat attcctattc ttttgacatt tggggccagg gaaccatggt aacagtgagt   360
tca                                                                 363

<210> SEQ ID NO 76
<211> LENGTH: 339
<212> TYPE: DNA
<213> ORGANISM: Artificial Sequence
<220> FEATURE:
<223> OTHER INFORMATION: Chemically Synthesized, CD9B389 VL

<400> SEQUENCE: 76
gatattgtga tgactcagac tccactctct ctgcccgtca cccctggaga accggcctcc    60
atctcctgca ggtctagtca gagcctcttt gatagtgatg atggaaacac ctatttggac   120
tggttcctgc agaagccagg gcagtctcca cagctcctaa tccaaacgct ttcctatcgg   180
gcctctggag tcccagacag gttcagtggc agtgggtcag gcaccgattt cacactgaaa   240
atcagcaggg tggaggctga tgatgttgga gtttattact gcatgcaacg tatggagttt   300
ccgctcactt tcggcggagg gaccaagctg gagatcaaa                          339

<210> SEQ ID NO 77
<211> LENGTH: 363
<212> TYPE: DNA
<213> ORGANISM: Artificial Sequence
<220> FEATURE:
<223> OTHER INFORMATION: Chemically Synthesized, CD9B390 VH

<400> SEQUENCE: 77
caggtacaac ttcaggagag cggcccaggt ttggttaaac aagtgaaac  cttgtcactt    60 acctgttccg tgtcaggtgg gtcaataagc aattactact ggtcctggat tagacaacct   120
```

```
gctggaaagg ggcttgaatg gatcgggagg atattctact cagggaagac aaactacaat    180
agtagcctca agtccagggt gaccatgtcc gctgatactt ccaagaatca atttagcctt    240
aaattgtcct ccgttacagc cgctgatacc gcagtgtact actgtgcaag aggtgagtac    300
agtggcgaat actcatattc ctttgacatc tggggtcagg cactactgt gactgtttca     360 tct                                                                  363
```

<210> SEQ ID NO 78
<211> LENGTH: 339
<212> TYPE: DNA
<213> ORGANISM: Artificial Sequence
<220> FEATURE:
<223> OTHER INFORMATION: Chemically Synthesized, CD9B390 VL

<400> SEQUENCE: 78

```
gaaatagtga tgacgcagtc tccactctcc ctgcccgtca cccctggaga gccggcctcc     60
atttcctgcc ggtctagtca gagcctcttg gatagtgatg atggaaacac ctatgtggac    120
tggttcctgc agaagccagg gcagtctcca caactcctga tctatacgct ttcctatcgg    180
gcctctggag tcccagacag gttcagtggc agtgggtcag acactgattt cacactgaaa    240
atcagcaggg tggaggctga agatgttgga atttattact gcatgcaacg tatggagttt    300
ccgctcactt tcggcggagg gaccaaggtg gagatcaaa                           339
```

<210> SEQ ID NO 79
<211> LENGTH: 480
<212> TYPE: PRT
<213> ORGANISM: Artificial Sequence
<220> FEATURE:
<223> OTHER INFORMATION: Chemically Synthesized, CD79b full length scFv

<400> SEQUENCE: 79

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Arg Asn Tyr
            20                  25                  30

Trp Met Ser Trp Val Arg Gln Ala Pro Gly Cys Gly Leu Glu Trp Val
        35                  40                  45

Ala Asn Ile Asn Gln Asp Gly Ser Glu Lys Tyr Tyr Val Asp Ser Val
    50                  55                  60

Glu Gly Arg Phe Thr Ile Ser Arg Asp Asn Ala Lys Lys Ser Leu Trp
65                  70                  75                  80

Leu Gln Met Ser Ser Leu Arg Val Glu Asp Thr Ala Val Tyr Tyr Cys
                85                  90                  95

Ala Arg Asp Pro Ile Glu Ser Arg Phe Asp Tyr Trp Gly Gln Gly Thr
            100                 105                 110

Leu Val Thr Val Ser Ser Gly Gly Gly Ser Gly Gly Ser Gly Gly Cys
        115                 120                 125

Pro Pro Cys Gly Gly Ser Gly Gly Asp Val Val Met Thr Gln Ser Pro
    130                 135                 140

Leu Ser Leu Pro Val Thr Leu Gly Gln Pro Ala Ser Ile Ser Cys Arg
145                 150                 155                 160

Ser Ser Gln Ser Leu Val Tyr Ser Asp Gly Asn Thr Tyr Leu Ser Trp
                165                 170                 175

Phe Gln Gln Arg Pro Gly Gln Ser Pro Arg Arg Leu Ile Tyr Lys Val
            180                 185                 190
```

```
Ser Asn Arg Asp Ser Gly Val Pro Asp Arg Phe Ser Gly Ser Gly Ser
            195                 200                 205

Gly Thr Asp Phe Thr Leu Lys Ile Ser Arg Val Glu Ala Glu Asp Val
    210                 215                 220

Gly Val Tyr Tyr Cys Met Gln Gly Thr His Trp Pro Pro Thr Phe Gly
225                 230                 235                 240

Cys Gly Thr Lys Val Glu Ile Lys Glu Pro Lys Ser Ser Asp Lys Thr
                245                 250                 255

His Thr Cys Pro Pro Cys Pro Ala Pro Glu Ala Ala Gly Gly Pro Ser
            260                 265                 270

Val Phe Leu Phe Pro Pro Lys Pro Lys Asp Thr Leu Tyr Ile Thr Arg
        275                 280                 285

Glu Pro Glu Val Thr Cys Val Val Val Ser Val Ser His Glu Asp Pro
    290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Ala Leu Pro Ala Pro Ile Glu Lys Thr
        355                 360                 365

Ile Ser Lys Ala Lys Gly Gln Pro Arg Glu Pro Gln Val Tyr Thr Leu
    370                 375                 380

Pro Pro Ser Arg Glu Glu Met Thr Lys Asn Gln Val Ser Leu Trp Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Lys Leu Thr Val Asp Lys Ser
        435                 440                 445

Arg Trp Gln Gln Gly Asn Val Phe Ser Cys Ser Val Met His Glu Ala
    450                 455                 460

Leu His Asn His Tyr Thr Gln Lys Ser Leu Ser Leu Ser Pro Gly Lys
465                 470                 475                 480

<210> SEQ ID NO 80
<211> LENGTH: 118
<212> TYPE: PRT
<213> ORGANISM: Artificial Sequence
<220> FEATURE:
<223> OTHER INFORMATION: Chemically Synthesized, CD79b scFv vH

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Arg Asn Tyr
            20                  25                  30

Trp Met Ser Trp Val Arg Gln Ala Pro Gly Cys Gly Leu Glu Trp Val
        35                  40                  45

Ala Asn Ile Asn Gln Asp Gly Ser Glu Lys Tyr Tyr Val Asp Ser Val
    50                  55                  60

Glu Gly Arg Phe Thr Ile Ser Arg Asp Asn Ala Lys Lys Ser Leu Trp
65                  70                  75                  80
```

```
Leu Gln Met Ser Ser Leu Arg Val Glu Asp Thr Ala Val Tyr Tyr Cys
                85                  90                  95

Ala Arg Asp Pro Ile Glu Ser Arg Phe Asp Tyr Trp Gly Gln Gly Thr
            100                 105                 110

Leu Val Thr Val Ser Ser
        115
```

<210> SEQ ID NO 81
<211> LENGTH: 112
<212> TYPE: PRT
<213> ORGANISM: Artificial Sequence
<220> FEATURE:
<223> OTHER INFORMATION: Chemically Synthesized, CD79b scFv vL

<400> SEQUENCE: 81

```
Asp Val Val Met Thr Gln Ser Pro Leu Ser Leu Pro Val Thr Leu Gly
1               5                   10                  15

Gln Pro Ala Ser Ile Ser Cys Arg Ser Gln Ser Leu Val Tyr Ser
            20                  25                  30

Asp Gly Asn Thr Tyr Leu Ser Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Cys Gly Thr Lys Val Glu Ile Lys
            100                 105                 110
```

<210> SEQ ID NO 82
<211> LENGTH: 248
<212> TYPE: PRT
<213> ORGANISM: Artificial Sequence
<220> FEATURE:
<223> OTHER INFORMATION: Chemically Synthesized, CD79b scFV

<400> SEQUENCE: 82

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Arg Asn Tyr
            20                  25                  30

Trp Met Ser Trp Val Arg Gln Ala Pro Gly Cys Gly Leu Glu Trp Val
        35                  40                  45

Ala Asn Ile Asn Gln Asp Gly Ser Glu Lys Tyr Tyr Val Asp Ser Val
    50                  55                  60

Glu Gly Arg Phe Thr Ile Ser Arg Asp Asn Ala Lys Lys Ser Leu Trp
65                  70                  75                  80

Leu Gln Met Ser Ser Leu Arg Val Glu Asp Thr Ala Val Tyr Tyr Cys
                85                  90                  95

Ala Arg Asp Pro Ile Glu Ser Arg Phe Asp Tyr Trp Gly Gln Gly Thr
            100                 105                 110

Leu Val Thr Val Ser Ser Gly Gly Gly Ser Gly Gly Cys
        115                 120                 125

Pro Pro Cys Gly Gly Ser Gly Gly Asp Val Val Met Thr Gln Ser Pro
    130                 135                 140

Leu Ser Leu Pro Val Thr Leu Gly Gln Pro Ala Ser Ile Ser Cys Arg
145                 150                 155                 160
```

```
Ser Ser Gln Ser Leu Val Tyr Ser Asp Gly Asn Thr Tyr Leu Ser Trp
            165                 170                 175

Phe Gln Gln Arg Pro Gly Gln Ser Pro Arg Arg Leu Ile Tyr Lys Val
            180                 185                 190

Ser Asn Arg Asp Ser Gly Val Pro Asp Arg Phe Ser Gly Ser Gly Ser
            195                 200                 205

Gly Thr Asp Phe Thr Leu Lys Ile Ser Arg Val Glu Ala Glu Asp Val
            210                 215                 220

Gly Val Tyr Tyr Cys Met Gln Gly Thr His Trp Pro Pro Thr Phe Gly
225                 230                 235                 240

Cys Gly Thr Lys Val Glu Ile Lys
            245

<210> SEQ ID NO 83
<211> LENGTH: 452
<212> TYPE: PRT
<213> ORGANISM: Artificial Sequence
<220> FEATURE:
<223> OTHER INFORMATION: Chemically Synthesized, CD22 Heavy chain Fab

<400> SEQUENCE: 83

Gln Val Thr Leu Arg Glu Ser Gly Pro Ala Leu Val Lys Pro Thr Gln
1               5                   10                  15

Thr Leu Thr Leu Thr Cys Thr Ser Gly Leu Pro Leu Ser Thr Ser
            20                  25                  30

Gly Met Ala Val Thr Trp Ile Arg Gln Pro Pro Gly Lys Ala Leu Glu
            35                  40                  45

Trp Leu Ala Leu Ile Asp Trp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Arg Met Gly Tyr Ser Tyr Gly Trp Asp Ala Phe Asp Leu Trp
            100                 105                 110

Gly Gln Gly Thr Met Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
            245                 250                 255

Tyr Ile Thr Arg Glu Pro Glu Val Thr Cys Val Val Val Ser Val Ser
            260                 265                 270
```

```
His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
                355                 360                 365

Ser Leu Ser Cys Ala Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn Arg Phe Thr Gln Lys Ser Leu Ser Leu
    435                 440                 445

Ser Pro Gly Lys
        450

<210> SEQ ID NO 84
<211> LENGTH: 214
<212> TYPE: PRT
<213> ORGANISM: Artificial Sequence
<220> FEATURE:
<223> OTHER INFORMATION: Chemically Synthesized, CD22 light chain Fab

<400> SEQUENCE: 84

Glu Val Val Met Thr Gln Ser Pro Ala Thr Leu Ser Val Ser Pro Gly
1               5                   10                  15

Glu Gly Ala Thr Leu Ser Cys Arg Ala Ser Gln Ser Gly Ser Arg Asn
            20                  25                  30

Ile Ala Trp Tyr Gln Gln Lys Pro Gly Gln Ala Pro Arg Leu Leu Ile
        35                  40                  45

Phe Gly Ala Ser Ala Arg Ala Thr Gly Ile Pro Ala Arg Phe Thr Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 85
<211> LENGTH: 330
<212> TYPE: PRT
<213> ORGANISM: Artificial Sequence
<220> FEATURE:
<223> OTHER INFORMATION: Chemically Synthesized, wild-type IgG1

<400> SEQUENCE: 85

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

Gln Lys Ser Leu Ser Leu Ser Pro Gly Lys
            325                 330

<210> SEQ ID NO 86
<211> LENGTH: 326
<212> TYPE: PRT
<213> ORGANISM: Artificial Sequence
<220> FEATURE:
<223> OTHER INFORMATION: Chemically Synthesized, wild-type IgG2

<400> SEQUENCE: 86

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 87

<211> LENGTH: 327
<212> TYPE: PRT
<213> ORGANISM: Artificial Sequence
<220> FEATURE:
<223> OTHER INFORMATION: Chemically Synthesized, wild-type IgG4

<400> SEQUENCE: 87

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 88
<211> LENGTH: 232
<212> TYPE: PRT
<213> ORGANISM: Artificial Sequence
<220> FEATURE:
<223> OTHER INFORMATION: Chemically Synthesized, IgG derivative

<400> SEQUENCE: 88

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 89
<211> LENGTH: 232
<212> TYPE: PRT
<213> ORGANISM: Artificial Sequence
<220> FEATURE:
<223> OTHER INFORMATION: Chemically Synthesized, IgG derivative with variants

<400> SEQUENCE: 89

```
Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Tyr Ile Thr Arg Glu Pro Glu Val Thr Cys Val Val
        35                  40                  45

Val Ser Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110
```

```
Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
        130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 90
<211> LENGTH: 330
<212> TYPE: PRT
<213> ORGANISM: Artificial Sequence
<220> FEATURE:
<223> OTHER INFORMATION: Chemically Synthesized, IgG1 with variants

<400> SEQUENCE: 90

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Tyr Ile Thr Arg Glu Pro Glu Val Thr Cys
    130                 135                 140

Val Val Val Ser Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240
```

```
Met Thr Lys Asn Gln Val Ser Leu Ser Cys Ala Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Val Ser Lys Leu Thr Val Asp Lys Ser Arg Trp Gln Gln Gly Asn
        290                 295                 300

Val Phe Ser Cys Ser Val Met His Glu Ala Leu His Asn Arg Phe Thr
305                 310                 315                 320

Gln Lys Ser Leu Ser Leu Ser Pro Gly Lys
            325                 330
```

<210> SEQ ID NO 91
<211> LENGTH: 18
<212> TYPE: PRT
<213> ORGANISM: Artificial Sequence
<220> FEATURE:
<223> OTHER INFORMATION: Chemically Synthesized, linker

<400> SEQUENCE: 91

```
Gly Gly Gly Ser Gly Gly Ser Gly Gly Cys Pro Pro Cys Gly Gly Ser
1               5                   10                  15

Gly Gly
```

<210> SEQ ID NO 92
<211> LENGTH: 20
<212> TYPE: PRT
<213> ORGANISM: Artificial Sequence
<220> FEATURE:
<223> OTHER INFORMATION: Chemically Synthesized, linker

<400> SEQUENCE: 92

```
Gly Gly Ser Glu Gly Lys Ser Ser Gly Ser Gly Ser Glu Ser Lys Ser
1               5                   10                  15

Thr Gly Gly Ser
            20
```

<210> SEQ ID NO 93
<211> LENGTH: 8
<212> TYPE: PRT
<213> ORGANISM: Artificial Sequence
<220> FEATURE:
<223> OTHER INFORMATION: Chemically Synthesized, linker

<400> SEQUENCE: 93

```
Gly Gly Gly Ser Gly Gly Gly Ser
1               5
```

<210> SEQ ID NO 94
<211> LENGTH: 12
<212> TYPE: PRT
<213> ORGANISM: Artificial Sequence
<220> FEATURE:
<223> OTHER INFORMATION: Chemically Synthesized, linker

<400> SEQUENCE: 94

```
Gly Gly Gly Ser Gly Gly Gly Ser Gly Gly Gly Ser
1               5                   10
```

<210> SEQ ID NO 95
<211> LENGTH: 16
<212> TYPE: PRT

<213> ORGANISM: Artificial Sequence
<220> FEATURE:
<223> OTHER INFORMATION: Chemically Synthesized, linker

<400> SEQUENCE: 95

Gly Gly Gly Ser Gly Gly Gly Ser Gly Gly Gly Ser Gly Gly Gly Ser
1               5                   10                  15

<210> SEQ ID NO 96
<211> LENGTH: 20
<212> TYPE: PRT
<213> ORGANISM: Artificial Sequence
<220> FEATURE:
<223> OTHER INFORMATION: Chemically Synthesized, linker

<400> SEQUENCE: 96

Gly Gly Gly Ser Gly Gly Gly Ser Gly Gly Gly Ser Gly Gly Gly Ser
1               5                   10                  15

Gly Gly Gly Ser
            20

<210> SEQ ID NO 97
<211> LENGTH: 15
<212> TYPE: PRT
<213> ORGANISM: Artificial Sequence
<220> FEATURE:
<223> OTHER INFORMATION: Chemically Synthesized, linker

<400> SEQUENCE: 97

Gly Gly Gly Gly Ser Gly Gly Gly Gly Ser Gly Gly Gly Gly Ser
1               5                   10                  15

<210> SEQ ID NO 98
<211> LENGTH: 20
<212> TYPE: PRT
<213> ORGANISM: Artificial Sequence
<220> FEATURE:
<223> OTHER INFORMATION: Chemically Synthesized, linker

<400> SEQUENCE: 98

Gly Gly Gly Gly Ser Gly Gly Gly Gly Ser Gly Gly Gly Gly Ser Gly
1               5                   10                  15

Gly Gly Gly Ser
            20

<210> SEQ ID NO 99
<211> LENGTH: 25
<212> TYPE: PRT
<213> ORGANISM: Artificial Sequence
<220> FEATURE:
<223> OTHER INFORMATION: Chemically Synthesized, linker

<400> SEQUENCE: 99

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 100
<211> LENGTH: 18
<212> TYPE: PRT
<213> ORGANISM: Artificial Sequence
<220> FEATURE:
<223> OTHER INFORMATION: Chemically Synthesized, linker

<400> SEQUENCE: 100

Gly Ser Thr Ser Gly Ser Gly Lys Pro Gly Ser Gly Glu Ser Thr
1               5                   10                  15

Lys Gly

<210> SEQ ID NO 101
<211> LENGTH: 14
<212> TYPE: PRT
<213> ORGANISM: Artificial Sequence
<220> FEATURE:
<223> OTHER INFORMATION: Chemically Synthesized, linker

<400> SEQUENCE: 101

Ile Arg Pro Arg Ala Ile Gly Gly Ser Lys Pro Arg Val Ala
1               5                   10

<210> SEQ ID NO 102
<211> LENGTH: 15
<212> TYPE: PRT
<213> ORGANISM: Artificial Sequence
<220> FEATURE:
<223> OTHER INFORMATION: Chemically Synthesized, linker

<400> SEQUENCE: 102

Gly Lys Gly Gly Ser Gly Lys Gly Gly Ser Gly Lys Gly Gly Ser
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Chemically Synthesized, linker

<400> SEQUENCE: 103

Gly Gly Lys Gly Ser Gly Gly Lys Gly Ser Gly Gly Lys Gly Ser
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Chemically Synthesized, linker

<400> SEQUENCE: 104

Gly Gly Gly Lys Ser Gly Gly Gly Lys Ser Gly Gly Gly Lys Ser
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Chemically Synthesized, linker

<400> SEQUENCE: 105

Gly Lys Gly Lys Ser Gly Lys Gly Lys Ser Gly Lys Gly Lys Ser
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Chemically Synthesized, linker

```
<400> SEQUENCE: 106

Gly Gly Gly Lys Ser Gly Gly Lys Gly Ser Gly Lys Gly Gly Ser
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Chemically Synthesized, linker

<400> SEQUENCE: 107

Gly Lys Pro Gly Ser Gly Lys Pro Gly Ser Gly Lys Pro Gly Ser
1               5                   10                  15

<210> SEQ ID NO 108
<211> LENGTH: 20
<212> TYPE: PRT
<213> ORGANISM: Artificial Sequence
<220> FEATURE:
<223> OTHER INFORMATION: Chemically Synthesized, linker

<400> SEQUENCE: 108

Gly Lys Pro Gly Ser Gly Lys Pro Gly Ser Gly Lys Pro Gly Ser Gly
1               5                   10                  15

Lys Pro Gly Ser
            20

<210> SEQ ID NO 109
<211> LENGTH: 20
<212> TYPE: PRT
<213> ORGANISM: Artificial Sequence
<220> FEATURE:
<223> OTHER INFORMATION: Chemically Synthesized, linker

<400> SEQUENCE: 109

Gly Lys Gly Lys Ser Gly Lys Gly Lys Ser Gly Lys Gly Lys Ser Gly
1               5                   10                  15

Lys Gly Lys Ser
            20

<210> SEQ ID NO 110
<211> LENGTH: 14
<212> TYPE: PRT
<213> ORGANISM: Artificial Sequence
<220> FEATURE:
<223> OTHER INFORMATION: Chemically Synthesized, linker

<400> SEQUENCE: 110

Ser Thr Ala Gly Asp Thr His Leu Gly Gly Glu Asp Phe Asp
1               5                   10

<210> SEQ ID NO 111
<211> LENGTH: 15
<212> TYPE: PRT
<213> ORGANISM: Artificial Sequence
<220> FEATURE:
<223> OTHER INFORMATION: Chemically Synthesized, linker

<400> SEQUENCE: 111

Gly Glu Gly Gly Ser Gly Glu Gly Gly Ser Gly Glu Gly Gly Ser
1               5                   10                  15

<210> SEQ ID NO 112
<211> LENGTH: 15
```

```
<212> TYPE: PRT
<213> ORGANISM: Artificial Sequence
<220> FEATURE:
<223> OTHER INFORMATION: Chemically Synthesized, linker

<400> SEQUENCE: 112

Gly Gly Glu Gly Ser Gly Gly Glu Gly Ser Gly Gly Glu Gly Ser
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Chemically Synthesized, linker

<400> SEQUENCE: 113

Gly Glu Gly Glu Ser Gly Glu Gly Glu Ser Gly Glu Gly Glu Ser
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Chemically Synthesized, linker

<400> SEQUENCE: 114

Gly Gly Gly Glu Ser Gly Gly Glu Gly Ser Gly Glu Gly Gly Ser
1               5                   10                  15

<210> SEQ ID NO 115
<211> LENGTH: 20
<212> TYPE: PRT
<213> ORGANISM: Artificial Sequence
<220> FEATURE:
<223> OTHER INFORMATION: Chemically Synthesized, linker

<400> SEQUENCE: 115

Gly Glu Gly Glu Ser Gly Glu Gly Glu Ser Gly Glu Gly Glu Ser Gly
1               5                   10                  15

Glu Gly Glu Ser
            20

<210> SEQ ID NO 116
<211> LENGTH: 18
<212> TYPE: PRT
<213> ORGANISM: Artificial Sequence
<220> FEATURE:
<223> OTHER INFORMATION: Chemically Synthesized, linker

<400> SEQUENCE: 116

Gly Ser Thr Ser Gly Ser Gly Lys Pro Gly Ser Gly Glu Gly Ser Thr
1               5                   10                  15

Lys Gly

<210> SEQ ID NO 117
<211> LENGTH: 19
<212> TYPE: PRT
<213> ORGANISM: Artificial Sequence
<220> FEATURE:
<223> OTHER INFORMATION: Chemically Synthesized, linker

<400> SEQUENCE: 117

Pro Arg Gly Ala Ser Lys Ser Gly Ser Ala Ser Gln Thr Gly Ser Ala
1               5                   10                  15
```

Pro Gly Ser

<210> SEQ ID NO 118
<211> LENGTH: 19
<212> TYPE: PRT
<213> ORGANISM: Artificial Sequence
<220> FEATURE:
<223> OTHER INFORMATION: Chemically Synthesized, linker

<400> SEQUENCE: 118

Gly Thr Ala Ala Ala Gly Ala Gly Ala Ala Gly Gly Ala Ala Ala Gly
1               5                   10                  15

Ala Ala Gly

<210> SEQ ID NO 119
<211> LENGTH: 19
<212> TYPE: PRT
<213> ORGANISM: Artificial Sequence
<220> FEATURE:
<223> OTHER INFORMATION: Chemically Synthesized, linker

<400> SEQUENCE: 119

Gly Thr Ser Gly Ser Ser Gly Ser Gly Ser Gly Gly Ser Gly Ser Gly
1               5                   10                  15

Gly Gly Gly

<210> SEQ ID NO 120
<211> LENGTH: 20
<212> TYPE: PRT
<213> ORGANISM: Artificial Sequence
<220> FEATURE:
<223> OTHER INFORMATION: Chemically Synthesized, linker

<400> SEQUENCE: 120

Gly Lys Pro Gly Ser Gly Lys Pro Gly Ser Gly Lys Pro Gly Ser Gly
1               5                   10                  15

Lys Pro Gly Ser
            20

<210> SEQ ID NO 121
<211> LENGTH: 4
<212> TYPE: PRT
<213> ORGANISM: Artificial Sequence
<220> FEATURE:
<223> OTHER INFORMATION: Chemically Synthesized, linker

<400> SEQUENCE: 121

Gly Ser Gly Ser
1

<210> SEQ ID NO 122
<211> LENGTH: 10
<212> TYPE: PRT
<213> ORGANISM: Artificial Sequence
<220> FEATURE:
<223> OTHER INFORMATION: Chemically Synthesized, linker

<400> SEQUENCE: 122

Ala Pro Ala Pro Ala Pro Ala Pro Ala Pro
1               5                   10

<210> SEQ ID NO 123
<211> LENGTH: 20
<212> TYPE: PRT

<213> ORGANISM: Artificial Sequence
<220> FEATURE:
<223> OTHER INFORMATION: Chemically Synthesized, linker

<400> SEQUENCE: 123

```
Ala Pro Ala Pro Ala Pro Ala Pro Ala Pro Ala Pro Ala Pro Ala Pro
1               5                   10                  15
Ala Pro Ala Pro
            20
```

<210> SEQ ID NO 124
<211> LENGTH: 32
<212> TYPE: PRT
<213> ORGANISM: Artificial Sequence
<220> FEATURE:
<223> OTHER INFORMATION: Chemically Synthesized, linker

<400> SEQUENCE: 124

```
Ala Glu Ala Ala Ala Lys Glu Ala Ala Ala Lys Glu Ala Ala Ala Ala
1               5                   10                  15
Lys Glu Ala Ala Ala Ala Lys Glu Ala Ala Ala Lys Ala Ala Ala
                20                  25                  30
```

<210> SEQ ID NO 125
<211> LENGTH: 10
<212> TYPE: PRT
<213> ORGANISM: Artificial Sequence
<220> FEATURE:
<223> OTHER INFORMATION: Chemically Synthesized, linker

<400> SEQUENCE: 125

```
Gly Gly Gly Gly Ser Gly Gly Gly Gly Ser
1               5                   10
```

<210> SEQ ID NO 126
<211> LENGTH: 229
<212> TYPE: PRT
<213> ORGANISM: Artificial Sequence
<220> FEATURE:
<223> OTHER INFORMATION: Chemically Synthesized, full length CD79b

<400> SEQUENCE: 126

```
Met Ala Arg Leu Ala Leu Ser Pro Val Pro Ser His Trp Met Val Ala
1               5                   10                  15
Leu Leu Leu Leu Leu Ser Ala Glu Pro Val Pro Ala Ala Arg Ser Glu
                20                  25                  30
Asp Arg Tyr Arg Asn Pro Lys Gly Ser Ala Cys Ser Arg Ile Trp Gln
            35                  40                  45
Ser Pro Arg Phe Ile Ala Arg Lys Arg Gly Phe Thr Val Lys Met His
        50                  55                  60
Cys Tyr Met Asn Ser Ala Ser Gly Asn Val Ser Trp Leu Trp Lys Gln
65                  70                  75                  80
Glu Met Asp Glu Asn Pro Gln Gln Leu Lys Leu Glu Lys Gly Arg Met
                85                  90                  95
Glu Glu Ser Gln Asn Glu Ser Leu Ala Thr Leu Thr Ile Gln Gly Ile
            100                 105                 110
Arg Phe Glu Asp Asn Gly Ile Tyr Phe Cys Gln Gln Lys Cys Asn Asn
        115                 120                 125
Thr Ser Glu Val Tyr Gln Gly Cys Gly Thr Glu Leu Arg Val Met Gly
    130                 135                 140
Phe Ser Thr Leu Ala Gln Leu Lys Gln Arg Asn Thr Leu Lys Asp Gly
```

-continued

```
            145                 150                 155                 160
Ile Ile Met Ile Gln Thr Leu Leu Ile Ile Leu Phe Ile Ile Val Pro
                    165                 170                 175

Ile Phe Leu Leu Leu Asp Lys Asp Asp Ser Lys Ala Gly Met Glu Glu
                180                 185                 190

Asp His Thr Tyr Glu Gly Leu Asp Ile Asp Gln Thr Ala Thr Tyr Glu
        195                 200                 205

Asp Ile Val Thr Leu Arg Thr Gly Glu Val Lys Trp Ser Val Gly Glu
    210                 215                 220

His Pro Gly Gln Glu
225
```

ANTIBODY TARGETING CD22 AND CD79B

CROSS REFERENCE TO RELATED APPLICATIONS

This application claims priority to U.S. Provisional Application No. 63/165,416, filed Mar. 24, 2021, which is hereby incorporated by reference herein in its entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in the ASCII text file: 206389-0044-00US_SequenceListing.txt; created on Mar. 15, 2022, and having a file size of 80,036 bytes, is hereby incorporated by reference.

TECHNICAL FIELD

The disclosure provides multispecific antibodies that bind cluster of differentiation 79B protein (CD79B) and cluster of differentiation 22 (CD22), polynucleotides encoding the multispecific antibodies, vectors, host cells, as well as methods of making and using the multispecific antibodies.

BACKGROUND

The prevalence of autoimmune disease is estimated to be 3-5% of the general population, and dysregulation of B cells, autoreactive B cells, and the presence of autoantibodies is a common feature of many autoimmune diseases (Wang et al, 2015, J Intern Med 2015; 278: 369-395).

B cells, or B lymphocytes, are central components of adaptive immunity, responding to different pathogens by producing antibodies, performing the role of antigen-presenting cells, secreting cytokines, and developing into memory B cells after activation (Packard and Cambier, 2013, F1000Prime Rep, 5:40). B cells circulate in the blood and lymphatic systems. In the lymphoid organs, a B cell encounters its cognate antigen, and together with an additional signal from a T helper cell, the B cell can differentiate into effector plasma cells. These cells secrete specific antibodies that will circulate in the blood to target and eliminate antigens or pathogens (Puri et al., 2013, Int Rev Immunol, 32(4):397-427).

In healthy individuals, immune tolerance prevents the immune system from recognizing self-antigens, thus limiting targeting and destruction of healthy cells and tissues by B, T, and myeloid cells. Autoimmune diseases, however, are characterized by a break in tolerance, wherein immune cells recognize and react to self-antigens. In such cases, B cells recognize and produce antibodies directed against self-antigens ("autoantibodies"), which are then capable of targeting cells and tissues for destruction by other components of the immune system, such as complement, cytotoxic T cells, and myeloid cells.

To detect an antigen, either pathogen-derived or self-antigen, B cells express cell surface receptors (BCRs), which are multicomponent receptors composed of a transmembrane immunoglobulin molecule (mIg) and a disulfide linked heterodimer of CD79a (Igα) and CD79b (Igβ) (Chu et al., 2001, Appl Immunohistochem Mol Morphol, June; 9(2):97-106). CD79b is selectively expressed within the B cell lineage across many differentiation states of B cells. Activation of the BCR results in multiple immune-activating consequences, including B cell differentiation, antibody and autoantibody production, cytokine production, and antigen presentation to T cells.

SUMMARY

In some embodiments, the invention provides a multispecific antibody or multispecific binding fragment comprising:
  a) a first antigen-binding arm that binds cluster of differentiation 79B protein (CD79B), comprising a first variable heavy domain (VH1) and further comprising a first variable light domain (VL1); and
  b) a second antigen-binding arm that binds cluster of differentiation 22 (CD22), comprising a second variable heavy domain (VH2) and further comprising a second variable light domain (VL2).

In some embodiments, the first antigen-binding arm that binds CD79b comprises
  a) a heavy chain complementarity determining region (HCDR)1 of SEQ ID NOs: 9, 17, 25, 33, 41, 49, or 57;
  b) a HCDR2 of SEQ ID NOs: 10, 18, 26, 34, 42, 50 or 58;
  c) a HCDR3 of SEQ ID NOs: 11, 19, 27, 35, 43, 51, or 59;
  d) a light chain complementarity determining region (LCDR)1 of SEQ ID NOs: 12, 20, 28, 36, 44, 52, or 60;
  e) a LCDR2 of SEQ ID NOs: 13, 21, 29, 37, 45, 53, or 61; or
  f) a LCDR3 of SEQ ID NOs: 14, 22, 30, 38, 46, 54, and 62.

In some embodiment, the first antigen-binding arm that binds CD79b comprises
  (a) the HCDR1 of SEQ ID NO:9, the HCDR2 of SEQ ID NO:10, and the HCDR3 of SEQ ID NO:11; and the LCDR1 of SEQ ID NO:12, the LCDR2 of SEQ ID NO:13, and the LCDR3 of SEQ ID NO:14;
  (b) the HCDR1 of SEQ ID NO:17, the HCDR2 of SEQ ID NO:18, and the HCDR3 of SEQ ID NO:19; and the LCDR1 of SEQ ID NO:20, the LCDR2 of SEQ ID NO:21, and the LCDR3 of SEQ ID NO:22;
  (c) the HCDR1 of SEQ ID NO:25, the HCDR2 of SEQ ID NO:26, and the HCDR3 of SEQ ID NO:27; and the LCDR1 of SEQ ID NO:28, the LCDR2 of SEQ ID NO:29, and the LCDR3 of SEQ ID NO:30;
  (d) the HCDR1 of SEQ ID NO:33, the HCDR2 of SEQ ID NO:34, and the HCDR3 of SEQ ID NO:35; and the LCDR1 of SEQ ID NO:36, the LCDR2 of SEQ ID NO:37, and the LCDR3 of SEQ ID NO:38;
  (e) the HCDR1 of SEQ ID NO:41, the HCDR2 of SEQ ID NO:42, and the HCDR3 of SEQ ID NO:43; and the LCDR1 of SEQ ID NO:44, the LCDR2 of SEQ ID NO:45, and the LCDR3 of SEQ ID NO:46;
  (f) the HCDR1 of SEQ ID NO:49, the HCDR2 of SEQ ID NO:50, and the HCDR3 of SEQ ID NO:51; and the LCDR1 of SEQ ID NO:52, the LCDR2 of SEQ ID NO:53, and the LCDR3 of SEQ ID NO:54; or
  (g) the HCDR1 of SEQ ID NO:57, the HCDR2 of SEQ ID NO:58, and the HCDR3 of SEQ ID NO:59; and the LCDR1 of SEQ ID NO:60, the LCDR2 of SEQ ID NO:61, and the LCDR3 of SEQ ID NO:62.

In some embodiments, the first antigen-binding arm that binds CD79b comprises a VH and VL of:
  a) the VH of SEQ ID NO: 15 and the VL of SEQ ID NO: 16;
  b) the VH of SEQ ID NO: 23 and the VL of SEQ ID NO: 24;
  c) the VH of SEQ ID NO: 31 and the VL of SEQ ID NO: 32;

d) the VH of SEQ ID NO: 39 and the VL of SEQ ID NO: 40;

e) the VH of SEQ ID NO: 47 and the VL of SEQ ID NO: 48;

f) the VH of SEQ ID NO: 55 and the VL of SEQ ID NO: 56;

g) the VH of SEQ ID NO: 63 and the VL of SEQ ID NO: 64; or h) the VH of SEQ ID NO: 80 and the VL of SEQ ID NO: 81.

In some embodiments, the antigen-binding arm that binds CD79b comprises: a VH1 comprising the HCDR1 of SEQ ID NO:9, the HCDR2 of SEQ ID NO:10, and the HCDR3 of SEQ ID NO:11; and a VL1 comprising the LCDR1 of SEQ ID NO:12, the LCDR2 of SEQ ID NO:13, and the LCDR3 of SEQ ID NO:14.

In some embodiments, the antigen-binding arm that binds CD79b comprises the VH1 of SEQ ID NO: 80 and the VL1 of SEQ ID NO: 81.

In some embodiments, the second antigen-binding arm that binds CD22 comprises a VH2 comprising the HCDR1 of SEQ ID NO:1, the HCDR2 of SEQ ID NO:2, and the HCDR3 of SEQ ID NO:3, and a VL2 comprising the LCDR1 of SEQ ID NO:4, the LCDR2 of SEQ ID NO:5, and the LCDR3 of SEQ ID NO:6.

In some embodiments, the VH2 comprises SEQ ID NO:7 and the VL2 comprises SEQ ID NO:8.

In some embodiments, the first antigen-binding arm that binds CD79b comprises
a) a heavy chain complementarity determining region (HCDR)1 of SEQ ID NOs: 9, 17, 25, 33, 41, 49, or 57;
b) a HCDR2 of SEQ ID NOs: 10, 18, 26, 34, 42, 50 or 58;
c) a HCDR3 of SEQ ID NOs: 11, 19, 27, 35, 43, 51, or 59;
d) a light chain complementarity determining region (LCDR)1 of SEQ ID NOs: 12, 20, 28, 36, 44, 52, or 60;
e) a LCDR2 of SEQ ID NOs: 13, 21, 29, 37, 45, 53, or 61; or
f) a LCDR3 of SEQ ID NOs: 14, 22, 30, 38, 46, 54, and 62, and
the second antigen-binding arm that binds CD22 comprises a VH2 comprising the HCDR1 of SEQ ID NO:1, the HCDR2 of SEQ ID NO:2, and the HCDR3 of SEQ ID NO:3, and a VL2 comprising the LCDR1 of SEQ ID NO:4, the LCDR2 of SEQ ID NO:5, and the LCDR3 of SEQ ID NO:6.

In some embodiments, the first antigen-binding arm that binds CD79b comprises the HCDR1 of SEQ ID NO:9, the HCDR2 of SEQ ID NO:10, and the HCDR3 of SEQ ID NO:11; and a VL1 comprising the LCDR1 of SEQ ID NO:12, the LCDR2 of SEQ ID NO:13, and the LCDR3 of SEQ ID NO:14, and the second antigen-binding arm that binds CD22 comprises a VH2 comprising the HCDR1 of SEQ ID NO:1, the HCDR2 of SEQ ID NO:2, and the HCDR3 of SEQ ID NO:3, and a VL2 comprising the LCDR1 of SEQ ID NO:4, the LCDR2 of SEQ ID NO:5, and the LCDR3 of SEQ ID NO:6.

In some embodiments, the first antigen-binding arm that binds CD79b comprises the VH1 of SEQ ID NO: 80 and the VL1 of SEQ ID NO: 81, and the second antigen-binding arm that binds CD22 comprises the VH2 comprises SEQ ID NO:7 and the VL2 comprises SEQ ID NO:8.

In some embodiments, the first or second antigen-binding arm comprises a single-chain variable fragment (scFv), an (scFv)$_2$, an antigen-binding fragment (Fab), a F(ab')$_2$, a Fd, a Fv, a VHH, or a dAB.

In some embodiments, the first antigen-binding arm comprises an scFv, and the second antigen-binding arm comprises a Fab.

In some embodiments, the first antigen-binding arm comprises an scFv having the amino acid sequence of SEQ ID NO:82.

In some embodiments, the first antigen-binding arm that binds CD79b comprises or is operably linked to a first Fragment crystallizable (Fc) domain, and the second antigen-binding arm that binds CD22 comprises or is operably linked to a second Fc domain.

In some embodiments, at least one of the first and second Fc domain comprises one or more mutations that promote heterodimerization of the Fc domains, reduce Fc binding to a Fcγ receptor, reduce Fc binding to protein A, extend the half-life of the multispecific antibody or multispecific binding fragment, or any combination thereof.

In some embodiments, the one or more mutations that promote heterodimerization of the Fc domains are selected from T366S, L368A, T366W, and Y407V (EU numbering).

In some embodiments, the first Fc domain comprise mutation T366W, and the second Fc domain comprises mutations T366S, L368A, and Y407V (EU numbering).

In some embodiments, the one or more mutations that reduce Fc binding to a Fcγ receptor are selected from L234A, L235A, and D265S (EU numbering).

In some embodiments, both the first Fc domain and the second Fc domain comprise mutations L234A, L235A, and D265S (EU numbering).

In some embodiments, the one or more mutations that reduce Fc binding to protein A are selected from H435R and Y436F (EU numbering).

In some embodiments, the second Fc domain comprises mutations H435R and Y436F (EU numbering).

In some embodiments, the one or more mutations that extend the half-life of the multispecific antibody or multispecific binding fragment are selected from M252Y, S254T, and T256E (EU numbering).

In some embodiments, both the first Fc domain and the second Fc domain comprise mutations M252Y, S254T, and T256E.

In some embodiments, the first Fc domain comprises SEQ ID NO:89, and the second Fc domain comprises SEQ ID NO:90.

In some embodiments, the multispecific antibody or multispecific binding fragment comprises the amino acid sequences of SEQ ID NO:79, SEQ ID NO: 83, and SEQ ID NO: 84.

In some embodiments, the invention provides an immunoconjugate comprising a multispecific antibody or multispecific binding fragment according to this disclosure conjugated to a therapeutic agent or an imaging agent. In some embodiments, the immunoconjugate comprises the amino acid sequences of SEQ ID NO:79, SEQ ID NO: 83, and SEQ ID NO: 84, wherein at least one of SEQ ID NO:79, SEQ ID NO: 83, and SEQ ID NO: 84 is conjugated to a therapeutic agent or an imaging agent.

In some embodiments, the invention provides a pharmaceutical composition comprising a multispecific antibody or immunoconjugate molecule according to this disclosure and a pharmaceutically acceptable carrier. In some embodiments, the pharmaceutical composition comprises a multispecific antibody or immunoconjugate molecule comprising the amino acid sequences of SEQ ID NO:79, SEQ ID NO: 83, and SEQ ID NO: 84 and a pharmaceutically acceptable carrier.

In some embodiments, the invention provides at least one nucleic acid molecule encoding an antigen-binding arm or fragment thereof of a multispecific antibody or immunoconjugate molecule according to this disclosure. In some embodiments the invention provides a combination of nucleic acid molecules, wherein the combination of nucleic acid molecules encodes each of SEQ ID NO:79, SEQ ID NO: 83, and SEQ ID NO: 84.

In some embodiments, the invention provides at least one vector comprising a nucleic acid molecule encoding an antigen-binding arm or fragment thereof of a multispecific antibody or immunoconjugate molecule according to this disclosure. In some embodiments the invention provides a combination of vectors comprising a combination of nucleic acid molecules, wherein the combination of nucleic acid molecules encodes each of SEQ ID NO:79, SEQ ID NO: 83, and SEQ ID NO: 84.

In some embodiments, the invention provides at least one host cell comprising at least one vector comprising a nucleic acid molecule encoding at least one antigen-binding arm or fragment of a multispecific antibody or immunoconjugate molecule according to this disclosure. In some embodiments the invention provides a combination of vectors comprising a combination of nucleic acid molecules, wherein the combination of nucleic acid molecules encodes each of SEQ ID NO:79, SEQ ID NO: 83, and SEQ ID NO: 84.

In some embodiments, the invention provides a method of treating an autoimmune disease in a subject, comprising administering a therapeutically effective amount of the multispecific antibody or multispecific binding fragment or immunoconjugate according to this disclosure, to the subject for a time sufficient to treat the autoimmune disease. In some embodiments, the invention provides a method of treating an autoimmune disease in a subject, comprising administering a therapeutically effective amount of the multispecific antibody or multispecific binding fragment or immunoconjugate comprising SEQ ID NO:79, SEQ ID NO: 83, and SEQ ID NO: 84. In some embodiments, the invention provides a method of treating an autoimmune disease in a subject, comprising administering a therapeutically effective amount of the multispecific antibody or multispecific binding fragment or immunoconjugate comprising SEQ ID NO:79, SEQ ID NO: 83, and SEQ ID NO: 84 and further comprising a pharmaceutical carrier.

In some embodiments, the autoimmune disease is Systemic lupus erythematosus (SLE), Sjögren's syndrome (SjS), Rheumatoid arthritis, Autoimmune myopathies, Type I diabetes, Addison disease, Pernicious anemia, Autoimmune hepatitis, Primary biliary cholangitis (PBC), Autoimmune pancreatitis, Celiac disease, Focal segmental glomerulosclerosis, Primary membranous nephropathy, Ovarian insufficiency, Autoimmune orchitis, Dry eye disease, Idiopathic interstitial pneumonias, Thyroid disease (e.g, Grave's), Systemic sclerosis (Scleroderma), Myasthenic syndromes, Autoimmune encephalitis, Bullous skin diseases, TTP, ITP, AIHA, Anca vasculitis, Myocarditis/dilatory CM, NMOSD, Maternal-fetal alloimmunity, Maternal-fetal autoimmunity, Anti-cardiolipin/antiphospholipid syndrome, Hypergammaglobulinemia, Transplant-associated ID, or Multifocal motor neuropathy.

In some embodiments, the invention provides a method of modulating B cell activation or inhibiting aberrant B cell activation, comprising administering the multispecific antibody or multispecific binding fragment or immunoconjugate according to this disclosure, to the subject. In some embodiments, the invention provides a method of modulating B cell activation or inhibiting aberrant B cell activation, comprising administering the multispecific antibody or multispecific binding fragment or immunoconjugate comprising SEQ ID NO:79, SEQ ID NO: 83, and SEQ ID NO: 84.

In some embodiments, the invention provides a method of modulating B cell activation or inhibiting aberrant B cell activation in a subject, comprising administering an effective amount of the multispecific antibody or multispecific binding fragment or immunoconjugate according to this disclosure, to the subject for a time sufficient to modulate B cell activation or inhibit aberrant B cell activation. In some embodiments, the invention provides a method of modulating B cell activation or inhibiting aberrant B cell activation in a subject, comprising administering an effective amount of the multispecific antibody or multispecific binding fragment or immunoconjugate comprising SEQ ID NO:79, SEQ ID NO: 83, and SEQ ID NO: 84 to the subject for a time sufficient to modulate B cell activation or inhibit aberrant B cell activation.

In some embodiments, the invention relates to the use of an effective amount of a multispecific antibody or multispecific binding fragment or immunoconjugate according to this disclosure for modulating B cell activation, inhibiting aberrant B cell activation, or treating an autoimmune disease, in a subject. In some embodiments, the invention relates to the use of an effective amount of a multispecific antibody or multispecific binding fragment or immunoconjugate for modulating B cell activation, inhibiting aberrant B cell activation, or treating an autoimmune disease, in a subject, wherein the multispecific antibody or multispecific binding fragment or immunoconjugate comprises SEQ ID NO:79, SEQ ID NO: 83, and SEQ ID NO: 84.

In some embodiments, the invention provides a method of decreasing B cell proliferation, decreasing cytokine production or reducing B cell activation in a subject, comprising administering an effective amount of the multispecific antibody or multispecific binding fragment or immunoconjugate according to this disclosure, to the subject for a time sufficient to decrease B cell proliferation, decrease cytokine production or reduce B cell activation. In some embodiments, the invention provides a method of decreasing B cell proliferation, decreasing cytokine production or reducing B cell activation in a subject, comprising administering an effective amount of the multispecific antibody or multispecific binding fragment or immunoconjugate comprising SEQ ID NO:79, SEQ ID NO: 83, and SEQ ID NO: 84.

In some embodiments, the invention relates to the use of an effective amount of a multispecific antibody or multispecific binding fragment or immunoconjugate according to this disclosure for decreasing B cell proliferation, decreasing cytokine production or reducing B cell activation. In some embodiments, the invention relates to the use of an effective amount of a multispecific antibody or multispecific binding fragment or immunoconjugate for decreasing B cell proliferation and cytokine production or reducing B cell activation, wherein the multispecific antibody or multispecific binding fragment or immunoconjugate comprises SEQ ID NO:79, SEQ ID NO: 83, and SEQ ID NO: 84.

BRIEF DESCRIPTION OF THE DRAWINGS

FIG. 3 depicts experimental results demonstrating B-cell distal read-outs (proliferation, cytokine secretion) were significantly inhibited by a CD22×CD79b bispecific antibody. Purified B-cells were cultured for 30 minutes with the following prior to stimulation: CD22×CD79b bispecific antibody (C192B30), a CD22×Isotype bispecific antibody (C192B36), and an Isotype×CD79b bispecific antibody (C192B2). After the 30 minutes B-cells were stimulated with a synergistic dose of anti-IgM F(ab)'2 (2.5 μg/mL) and CPG (0.3125 μM). As shown the CD22×CD79b antibody was able to significantly reduce B-cell proliferation in response to BCR+TLR stimulation in comparison to the isotype control arms. Further, B-cell IL-6 production was significantly impacted while again the isotype control arms show little to no effect.

FIG. 4 depicts experimental results demonstrating CD22× CD79b bispecific antibody inhibited in vivo IgM antibody production from an NSG-human PBMC transfer model. Human PBMCs were transferred into irradiated immunodeficient mice—NSG (NOD-scid IL2Rgamma$^{null}$). The mice were then treated with varying doses of a CD22×CD79b bispecific antibody (0.2 mg/kg, 1 mg/kg, and 5 mg/kg) or an isotype control antibody (5 mg/kg). The cells were then allowed to engraft for 7 days. During this time the B-cells began to produce human antibody in vivo. After 7 days the animal were sacrificed and splenocytes for flow cytometry and serum was taken for analysis. The serum showed a significant reduction of human IgM in the 5 mg/kg group treated with the CD22× CD79b bispecific antibody in comparison to controls (PBS and Isotype).

FIG. 5 depicts experimental results demonstrating that stapling the CD79b-scFv arm mitigated aggregation.

DETAILED DESCRIPTION

Figure 1:
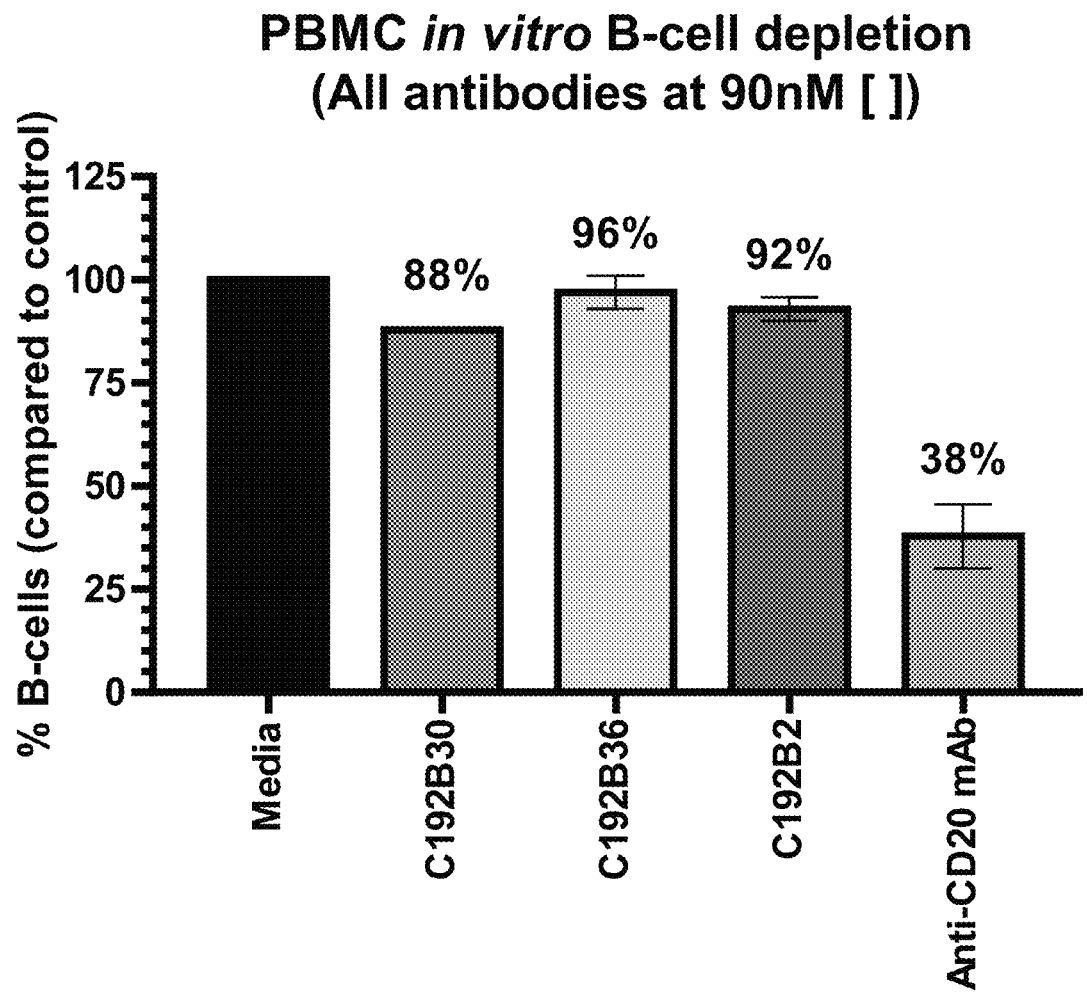
FIG. 1 depicts experimental results demonstrating the non-depleting capacity of the CD22× CD79b bispecific antibodies. PBMCs were cultured for 48-hours with: media alone, a CD22×CD79b bispecific antibody (C192B30), a CD22×Isotype bispecific antibody (C192B36), an Isotype× CD79b bispecific antibody (C192B2) or an anti-CD20 depleting mAb. After 48-hours, the cells were stained for live cells (Zombie Dye Aqua), T-cell (CD3), and B-cells (CD22, CD20, CD19). The percent of b-cells were then calculated in comparison to the media alone wells. The bispecific antibodies had little to no depletion of B-cells in any bispecific format while the positive control of anti-CD20 depleting mAb showed a significant decrease of B-cells in PBMCs.

The disclosed methods may be understood more readily by reference to the following detailed description. It is to be understood that the disclosed methods are not limited to the specific methods described and/or shown herein, and that the terminology used herein is for the purpose of describing particular embodiments by way of example only and is not intended to be limiting of the claimed methods.

All patents, published patent applications and publications cited herein are incorporated by reference as if set forth fully herein.

When a list is presented, unless stated otherwise, it is to be understood that each individual element of that list, and every combination of that list, is a separate embodiment. For example, a list of embodiments presented as "A, B, or C" is to be interpreted as including the embodiments "A," "B," "C," "A or B," "A or C," "B or C," or "A, B, or C."

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Definitions

As used in this specification and the appended claims, the singular forms "a," "an," and "the" include plural referents unless the content clearly dictates otherwise. Thus, for example, reference to "a cell" includes a combination of two or more cells, and the like.

The transitional terms "comprising," "consisting essentially of," and "consisting of" are intended to connote their generally accepted meanings in the patent vernacular; that is, (i) "comprising," which is synonymous with "including," "containing," or "characterized by," is inclusive or open-ended, and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents) also provide as embodiments those independently described in terms of "consisting of" and "consisting essentially of."

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is larger.

"Activation," "stimulation," "activated," or "stimulated" refer to induction of a change in the biologic state of a cell resulting in expression of activation markers, cytokine production, proliferation or mediating cytotoxicity of target cells. Cells may be activated by primary stimulatory signals. Co-stimulatory signals can amplify the magnitude of the primary signals and suppress cell death following initial stimulation resulting in a more durable activation state and thus a higher cytotoxic capacity. A "co-stimulatory signal" refers to a signal, which in combination with a primary signal, such as TCR/CD3 ligation, leads to T cell and/or natural killer (NK) cell proliferation and/or upregulation or downregulation of key molecules.

"Alternative scaffold" refers to a single chain protein framework that contains a structured core associated with variable domains of high conformational tolerance. The variable domains tolerate variation to be introduced without compromising scaffold integrity, and hence the variable domains can be engineered and selected for binding to a specific antigen.

"Antibody-dependent cellular cytotoxicity", "antibody-dependent cell-mediated cytotoxicity" or "ADCC" refers to the mechanism of inducing cell death that depends upon the interaction of antibody-coated target cells with effector cells possessing lytic activity, such as NK cells, monocytes, macrophages and neutrophils via Fc gamma receptors (FcgR) expressed on effector cells.

"Antibody-dependent cellular phagocytosis" or "ADCP" refers to the mechanism of elimination of antibody-coated target cells by internalization by phagocytic cells, such as macrophages or dendritic cells.

"Antigen" refers to any molecule (e.g., protein, peptide, polysaccharide, glycoprotein, glycolipid, nucleic acid, portions thereof, or combinations thereof) capable of being bound by an antigen binding domain. Antigens may be expressed by genes, synthetized, or purified from biological samples such as a tissue sample, a tumor sample, a cell or a fluid with other biological components, organisms, subunits of proteins/antigens, and killed or inactivated whole cells or lysates.

"Antigen binding fragment" or "antigen binding domain" refers to a portion of the protein that binds an antigen. Antigen binding fragments may be synthetic, enzymatically obtainable or genetically engineered polypeptides and include portions of an immunoglobulin that bind an antigen, such as VH, the VL, the VH and the VL, Fab, Fab', F(ab')$_2$, Fd and Fv fragments, domain antibodies (dAb) consisting of one VH domain or one VL domain, shark variable IgNAR domains, camelized VH domains, VHH domains, minimal recognition units consisting of the amino acid residues that mimic the CDRs of an antibody, such as FR3-CDR3-FR4 portions, the HCDR1, the HCDR2 and/or the HCDR3 and the LCDR1, the LCDR2 and/or the LCDR3, alternative scaffolds that bind an antigen, and multispecific proteins comprising the antigen binding fragments. Antigen binding fragments (such as VH and VL) may be linked together via a synthetic linker to form various types of single antibody designs where the VH/VL domains may pair intramolecularly, or intermolecularly in those cases when the VH and VL domains are expressed by separate single chains, to form a monovalent antigen binding domain, such as single chain Fv (scFv) or diabody. Antigen binding fragments may also be conjugated to other antibodies, proteins, antigen binding fragments or alternative scaffolds which may be monospecific or multispecific to engineer bispecific and multispecific proteins.

"Antibodies" is meant in a broad sense and includes immunoglobulin molecules including monoclonal antibodies including murine, human, humanized and chimeric monoclonal antibodies, antigen binding fragments, multi-specific antibodies, such as bispecific, trispecific, tetraspecific etc., dimeric, tetrameric or multimeric antibodies, single chain antibodies, domain antibodies and any other modified configuration of the immunoglobulin molecule that comprises an antigen binding site of the required specificity. "Full length antibodies" are comprised of two heavy chains (HC) and two light chains (LC) inter-connected by disulfide bonds as well as multimers thereof (e.g. IgM). Each HC is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL regions may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4. Immunoglobulins may be assigned to five major classes: IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species may be assigned to one of two clearly distinct types, namely kappa (κ) and lambda (λ), based on the amino acid sequences of their constant domains.

"Bispecific" refers to a molecule (such as an antibody) that specifically binds two distinct antigens or two distinct epitopes within the same antigen. The bispecific molecule may have cross-reactivity to other related antigens, for example to the same antigen from other species (homologs), such as human or monkey, for example *Macaca cynomolgus* (*Cynomolgus*, cyno) or *Pan troglodytes*, or may bind an epitope that is shared between two or more distinct antigens.

As used herein, the term "chimeric" refers to an antibody, or antigen-binding fragment thereof, having at least some portion of at least one variable domain derived from the antibody amino acid sequence of a non-human mammal, a rodent, or a reptile, while the remaining portions of the antibody, or antigen-binding fragment thereof, are derived from a human.

"Chimeric antigen receptor" (CAR) as used herein is defined as a cell-surface receptor comprising an extracellular target-binding domain, a transmembrane domain and an intracellular signaling domain, all in a combination that is not naturally found together on a single protein. This includes receptors wherein the extracellular domain and the intracellular signaling domain are not naturally found together on a single receptor protein. CARs are intended primarily for use with lymphocyte such as T cells and NK cells.

A "clone" is a population of cells derived from a single cell or common ancestor by mitosis. A "cell line" is a clone of a primary cell that is capable of stable growth in vitro for many generations. In some examples provided herein, cells are transformed by transfecting the cells with DNA.

"Complement-dependent cytotoxicity" or "CDC", refers to the mechanism of inducing cell death in which the Fc effector domain of a target-bound protein binds and activates complement component C1q which in turn activates the complement cascade leading to target cell death. Activation of complement may also result in deposition of complement components on the target cell surface that facilitate CDC by binding complement receptors (e.g., CR3) on leukocytes "Complementarity determining regions" (CDR) are antibody regions that bind an antigen. There are three CDRs in the VH (HCDR1, HCDR2, HCDR3) and three CDRs in the VL (LCDR1, LCDR2, LCDR3). CDRs may be defined using various delineations such as Kabat (Wu et al. (1970) J Exp Med 132: 211-50; Kabat et al., Sequences of Proteins of Immunological Interest, 5th Ed. Public Health Service, National Institutes of Health, Bethesda, Md., 1991), Chothia (Chothia et al. (1987) J Mol Biol 196: 901-17), IMGT (Lefranc et al. (2003) Dev Comp Immunol 27: 55-77) and AbM (Martin and Thornton J Bmol Biol 263: 800-15, 1996). The correspondence between the various delineations and variable region numbering is described (see e.g. Lefranc et al. (2003) Dev Comp Immunol 27: 55-77; Honegger and Pluckthun, J Mol Biol (2001) 309:657-70; International ImMunoGeneTics (IMGT) database; Web resources, http://www_imgt_org). Available programs such as abYsis by UCL Business PLC may be used to delineate CDRs. The term "CDR", "HCDR1", "HCDR2", "HCDR3", "LCDR1", "LCDR2" and "LCDR3" as used herein includes CDRs defined by any of the methods described supra, Kabat, Chothia, IMGT or AbM, unless otherwise explicitly stated in the specification.

Typically, CDRs form a loop structure that can be classified as a canonical structure. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia et al., "Canonical Structures For the Hypervariable Regions of Immunoglobulins," *J. Mol. Biol.* 196: 901 (1987); Chothia et al., "Conformations of Immunoglobulin Hypervariable Regions," I 342:877 (1989); Martin and Thornton, "Structural Families in Loops of Homologous Proteins: Automatic Classification, Modelling and Application to Antibodies," *J. Mol. Biol.* 263:800 (1996), each of which is incorporated by reference in its entirety). Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues "Decrease," "lower," "lessen," "reduce," or "abate" refers generally to the ability of a test molecule to mediate a reduced response (i.e., downstream effect) when compared to the response mediated by a control or a vehicle. Exemplary responses are T cell expansion, T cell activation or T-cell mediated tumor cell killing or binding of a protein to its antigen or receptor, and enhanced binding to a Fcγ or enhanced Fc effector functions such as enhanced ADCC, CDC and/or ADCP. Decrease may be a statistically significant difference in the measured response between the test molecule and the control (or the vehicle), or a decrease in the measured response, such as a decrease of about 1.1, 1.2, 1.5, 2, 3, 4, 5, 6, 7, 8, 9, 10, 15, 20 or 30 fold or more, such as 500, 600, 700, 800, 900 or 1000 fold or more (including all integers and decimal points in between and above 1, e.g., 1.5, 1.6, 1.7, 1.8, etc.).

"Domain Antibody," "dAb," or "dAb fragment" refers to an antibody fragment composed of either VH and the VL domains from a single arm of the antibody.

"Differentiation" refers to a method of decreasing the potency or proliferation of a cell or moving the cell to a more developmentally restricted state.

"Encode" or "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence, and the non-coding strand, used as the template for transcription of a gene or cDNA, can be referred to as encoding the protein or other product of that gene or cDNA.

"Enhance," "promote," "increase," "expand" or "improve" refers generally to the ability of a test molecule to mediate a greater response (i.e., downstream effect) when compared to the response mediated by a control or a vehicle. Exemplary responses are T cell expansion, T cell activation or T-cell mediated tumor cell killing or binding of a protein to its antigen or receptor, and enhanced binding to a Fcγ or enhanced Fc effector functions such as enhanced ADCC, CDC and/or ADCP Enhance may be a statistically significant difference in the measured response between the test molecule and control (or vehicle), or an increase in the measured response, such as an increase of about 1.1, 1.2, 1.5, 2, 3, 4, 5, 6, 7, 8, 9, 10, 15, 20 or 30 fold or more, such as 500, 600, 700, 800, 900 or 1000 fold or more (including all integers and decimal points in between and above 1, e.g., 1.5, 1.6, 1.7, 1.8, etc.).

"Expansion" refers to the outcome of cell division and cell death.

"Express" and "expression" refers the to the well-known transcription and translation occurring in cells or in vitro. The expression product, e.g., the protein, is thus expressed by the cell or in vitro and may be an intracellular, extracellular or a transmembrane protein.

"Expression vector" refers to a vector that can be utilized in a biological system or in a reconstituted biological system to direct the translation of a polypeptide encoded by a polynucleotide sequence present in the expression vector. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

"dAb" or "dAb fragment" refers to an antibody fragment composed of a VH domain (Ward et al., Nature 341:544 546 (1989)).

"Fab" or "Fab fragment" refers to an antibody fragment composed of VH, CH1, VL and CL domains.

"F(ab')₂" or "F(ab')₂ fragment" refers to an antibody fragment containing two Fab fragments connected by a disulfide bridge in the hinge region.

"Fd" or "Fd fragment" refers to an antibody fragment composed of VH and CH1 domains.

"Fv" or "Fv fragment" refers to an antibody fragment composed of the VH and the VL domains from a single arm of the antibody.

"Full length antibody" is comprised of two heavy chains (HC) and two light chains (LC) inter-connected by disulfide bonds as well as multimers thereof (e.g. IgM). Each heavy chain is comprised of a heavy chain variable domain (VH) and a heavy chain constant domain, the heavy chain constant domain comprised of subdomains CH1, hinge, CH2 and CH3. Each light chain is comprised of a light chain variable domain (VL) and a light chain constant domain (CL). The VH and the VL may be further subdivided into regions of hypervariability, termed complementarity determining regions (CDR), interspersed with framework regions (FR).

Each VH and VL is composed of three CDRs and four FR segments, arranged from amino-to-carboxy-terminus in the following order: FR1, CDR1, FR2, CDR2, FR3, CDR3 and FR4.

"Genetic modification" refers to the introduction of a "foreign" (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences operably linked to the polynucleotide encoding the chimeric antigen receptor, such as start, stop, promoter, signal, secretion, or other sequences used by a cell's genetic machinery. The gene or sequence may include nonfunctional sequences or sequences with no known function. A host cell that receives and expresses introduced DNA or RNA has been "genetically engineered." The DNA or RNA introduced to a host cell can come from any source, including cells of the same genus or species as the host cell, or from a different genus or species.

"Heterologous" refers to two or more polynucleotides or two or more polypeptides that are not found in the same relationship to each other in nature.

"Heterologous polynucleotide" refers to a non-naturally occurring polynucleotide that encodes two or more neoantigens as described herein.

"Heterologous polypeptide" refers to a non-naturally occurring polypeptide comprising two or more neoantigen polypeptides as described herein.

"Host cell" refers to any cell that contains a heterologous nucleic acid. An exemplary heterologous nucleic acid is a vector (e.g., an expression vector).

"Human antibody" refers to an antibody that is optimized to have minimal immune response when administered to a human subject. Variable regions of human antibody are derived from human immunoglobulin sequences. If human antibody contains a constant region or a portion of the constant region, the constant region is also derived from human immunoglobulin sequences. Human antibody comprises heavy and light chain variable regions that are "derived from" sequences of human origin if the variable regions of the human antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci. "Human antibody" typically contains amino acid differences when compared to the immunoglobulins expressed in humans due to differences between the systems used to obtain the human antibody and human immunoglobulin loci, introduction of somatic mutations or intentional introduction of substitutions into the frameworks or CDRs, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., (2000) J Mol Biol 296:57-86, or a synthetic HCDR3 incorporated into human immunoglobulin gene libraries displayed on phage, for example as described in Shi et al., (2010) J Mol Biol 397:385-96, and in Int. Patent Publ. No. WO2009/085462. Antibodies in which at least one CDR is derived from a non-human species are not included in the definition of "human antibody".

"Humanized antibody" refers to an antibody in which at least one CDR is derived from non-human species and at least one framework is derived from human immunoglobulin sequences. Humanized antibody may include substitutions in the frameworks so that the frameworks may not be exact copies of expressed human immunoglobulin or human immunoglobulin germline gene sequences.

"In combination with" means that two or more therapeutic agents are be administered to a subject together in a mixture, concurrently as single agents or sequentially as single agents in any order.

"Isolated" refers to a homogenous population of molecules (such as synthetic polynucleotides or polypeptides) which have been substantially separated and/or purified away from other components of the system the molecules are produced in, such as a recombinant cell, as well as a protein that has been subjected to at least one purification or isolation step. "Isolated" refers to a molecule that is substantially free of other cellular material and/or chemicals and encompasses molecules that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity. "Isolated" nucleic acids, peptides and proteins can be part of a composition and still be isolated if such composition is not part of the native environment of the nucleic acid, peptide, or protein. The term also embraces nucleic acids, peptides and proteins prepared by recombinant expression in a host cell as well as chemically synthesized nucleic acids. An "isolated" antibody or antigen-binding fragment, as used herein, is intended to refer to an antibody or antigen-binding fragment which is substantially free of other antibodies or antigen-binding fragments having different antigenic specificities (for instance, an isolated antibody that specifically binds to CD79b is substantially free of antibodies that specifically bind antigens other than CD79b). An isolated antibody that specifically binds to an epitope, isoform or variant of CD79b may, however, have cross-reactivity to other related antigens, for instance from other species (such as CD79b species homologs).

"Cluster of Differentiation CD22 protein" or "CD22" refers to a known protein which is also called CD22. The amino acid sequences of the various isoforms are retrievable from GenBank, including, for example, GenBank accession numbers NP_001762.2, NP_001172028.1, NP_001172029.1, NP_001172030.1, and NP_001265346.1.

"Cluster of Differentiation CD79B protein" or "CD79b" refers to a known protein which is also called CD79b. The amino acid sequences of the various isoforms are retrievable from GenBank accession numbers AAH32651.1, EAW94232.1, AAH02975.2, NP_000617.1, and NP_001035022.1. The amino acid sequence of the full length CD79b sequence is shown below. The sequence includes the extracellular domain (residues 29-159) and the cytoplasmic domain (residues 181-229).

(SEQ ID NO: 126)
MARLALSPVPSHWMVALLLLLSAEPVPAARSEDRYRNPKGSACSRIWQSPR

FIARKRGFTVKMHCYMNSASGNVSWLWKQEMDENPQQLKLEKGRMEESQNE

-continued
SLATLTIQGIRFEDNGIYFCQQKCNNTSEVYQGCGTELRVMGFSTLAQLKQ

RNTLKDGIIMIQTLLIILFIIVPIFLLLDKDDSKAGMEEDHTYEGLDIDQT

ATYEDIVTLRTGEVKWSVGEHPGQE

"Modulate" refers to either enhanced or decreased ability of a test molecule to mediate an enhanced or a reduced response (i.e., downstream effect) when compared to the response mediated by a control or a vehicle.

"Monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation. Monoclonal antibodies typically bind one antigenic epitope. A bispecific monoclonal antibody binds two distinct antigenic epitopes. Monoclonal antibodies may have heterogeneous glycosylation within the antibody population. Monoclonal antibody may be monospecific or multispecific such as bispecific, monovalent, bivalent or multivalent.

"Minibody" to refers to scFv fragments which are linked via CH3 domains.

"Multispecific" refers to a molecule, such as an antibody that specifically binds two or more distinct antigens or two or more distinct epitopes within the same antigen. Multispecific molecule may have cross-reactivity to other related antigens, for example to the same antigen from other species (homologs), such as human or monkey, for example *Macaca fascicularis* (*Cynomolgus*, cyno) or *Pan troglodytes*, or may bind an epitope that is shared between two or more distinct antigens.

"Natural killer cell" and "NK cell" are used interchangeably and synonymously herein. NK cell refers to a differentiated lymphocyte with a $CD16^+CD56^+$ and/or $CD57^+$ $TCR^-$ phenotype. NK cells are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

"Operatively linked" and similar phrases, when used in reference to nucleic acids or amino acids, refers to the operational linkage of nucleic acid sequences or amino acid sequence, respectively, placed in functional relationships with each other. For example, an operatively linked promoter, enhancer elements, open reading frame, 5' and 3' UTR, and terminator sequences result in the accurate production of a nucleic acid molecule (e.g., RNA) and in some instances to the production of a polypeptide (i.e., expression of the open reading frame). "Operatively linked peptide" refers to a peptide in which the functional domains of the peptide are placed with appropriate distance from each other to impart the intended function of each domain.

"Pharmaceutical combination" refers to a combination of two or more active ingredients administered either together or separately.

"Pharmaceutical composition" refers to a composition that results from combining an active ingredient and a pharmaceutically acceptable carrier.

"Pharmaceutically acceptable carrier" or "excipient" refers to an ingredient in a pharmaceutical composition, other than the active ingredient, which is nontoxic to a subject. Exemplary pharmaceutically acceptable carriers are a buffer, stabilizer or preservative.

"Polynucleotide" or "nucleic acid" refers to a synthetic molecule comprising a chain of nucleotides covalently linked by a sugar-phosphate backbone or other equivalent covalent chemistry. cDNA is a typical example of a polynucleotide. Polynucleotide may be a DNA or a RNA molecule.

"Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

"Prevent," "preventing," "prevention," or "prophylaxis" of a disease or disorder means preventing a disorder from occurring in a subject.

"Proliferation" refers to an increase in cell division, either symmetric or asymmetric division of cells.

"Promoter" refers to the minimal sequences required to initiate transcription. Promoter may also include enhancers or repressor elements which enhance or suppress transcription, respectively.

"Protein" or "polypeptide" are used interchangeably herein are refers to a molecule that comprises one or more polypeptides each comprised of at least two amino acid residues linked by a peptide bond. Protein may be a monomer, or may be protein complex of two or more subunits, the subunits being identical or distinct. Small polypeptides of less than 50 amino acids may be referred to as "peptides". Protein may be a heterologous fusion protein, a glycoprotein, or a protein modified by post-translational modifications such as phosphorylation, acetylation, myristoylation, palmitoylation, glycosylation, oxidation, formylation, amidation, citrullination, polyglutamylation, ADP-ribosylation, pegylation or biotinylation. Protein may be recombinantly expressed.

"Recombinant" refers to polynucleotides, polypeptides, vectors, viruses and other macromolecules that are prepared, expressed, created or isolated by recombinant means.

"Regulatory element" refers to any cis- or trans acting genetic element that controls some aspect of the expression of nucleic acid sequences.

"Relapsed" refers to the return of a disease or the signs and symptoms of a disease after a period of improvement after prior treatment with a therapeutic.

"Refractory" refers to a disease that does not respond to a treatment. A refractory disease can be resistant to a treatment before or at the beginning of the treatment, or a refractory disease can become resistant during a treatment.

"Single chain Fv" or "scFv" refers to a fusion protein comprising at least one antibody fragment comprising a light chain variable region (VL) and at least one antibody fragment comprising a heavy chain variable region (VH), wherein the VL and the VH are contiguously linked via a polypeptide linker, and capable of being expressed as a single chain polypeptide. Unless specified, as used herein, a scFv may have the VL and VH variable regions in either order, e.g., with respect to the N-terminal and C-terminal ends of the polypeptide, the scFv may comprise VL-linker-VH or may comprise VH-linker-VL. An scFv may be a stapled single chain Fv, as in Example 2.

"Specifically binds," "specific binding," "specifically binding" or "binds" refer to a proteinaceous molecule binding to an antigen or an epitope within the antigen with greater affinity than for other antigens. Typically, the proteinaceous molecule binds to the antigen or the epitope within the antigen with an equilibrium dissociation constant ($K_D$) of about $1 \times 10^{-7}$ M or less, for example about $5 \times 10^{-8}$ M or less, about $1 \times 10^{-8}$ M or less, about $1 \times 10^{-9}$ M or less, about $1 \times 10^{10}$ M or less, about $1 \times 10^{11}$ M or less, or about $1 \times 10^{12}$ M or less, typically with a $K_D$ that is at least one hundred fold less than its $K_D$ for binding to a non-specific antigen (e.g., BSA, casein). In the context of the CD79b antigens described here, "specific binding" refers to binding of the proteinaceous molecule to the CD79b antigen without detectable binding to a wild-type protein the antigen is a variant of.

"Subject" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. The terms "subject" and "patient" can be used interchangeably herein.

The meaning of "substantially the same" can differ depending on the context in which the term is used. Because of the natural sequence variation likely to exist among heavy and light chains and the genes encoding them, one would expect to find some level of variation within the amino acid sequences or the genes encoding the antibodies or antigen-binding fragments described herein, with little or no impact on their unique binding properties (e.g., specificity and affinity). Such an expectation is due in part to the degeneracy of the genetic code, as well as to the evolutionary success of conservative amino acid sequence variations, which do not appreciably alter the nature of the encoded protein. Accordingly, in the context of nucleic acid sequences, "substantially the same" means at least 65% identity between two or more sequences. Preferably, the term refers to at least 70% identity between two or more sequences, more preferably at least 75% identity, more preferably at least 80% identity, more preferably at least 85% identity, more preferably at least 90% identity, more preferably at least 91% identity, more preferably at least 92% identity, more preferably at least 93% identity, more preferably at least 94% identity, more preferably at least 95% identity, more preferably at least 96% identity, more preferably at least 97% identity, more preferably at least 98% identity, and more preferably at least 99% or greater identity. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

"T cell" and "T lymphocyte" are interchangeable and used synonymously herein. T cell includes thymocytes, naïve T lymphocytes, memory T cells, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4$^+$ T cell) CD4$^+$ T cell, a cytotoxic T cell (CTL; CD8$^+$ T cell), a tumor infiltrating cytotoxic T cell (TIL; CD8$^+$ T cell), CD4$^+$CD8$^+$ T cell, or any other subset of T cells. Also included are "NKT cells", which refer to a specialized population of T cells that express a semi-invariant αβ T-cell receptor, but also express a variety of molecular markers that are typically associated with NK cells, such as NK1.1. NKT cells include NK1.1$^+$ and NK1.1$^-$, as well as CD4$^+$, CD4$^-$, CD8$^+$ and CD8$^-$ cells. The TCR on NKT cells is unique in that it recognizes glycolipid antigens presented by the MHC I-like molecule CD Id. NKT cells can have either protective or deleterious effects due to their abilities to produce cytokines that promote either inflammation or immune tolerance. Also included are "gamma-delta T cells (γδ T cells)," which refer to a specialized population that to a small subset of T cells possessing a distinct TCR on their surface, and unlike the majority of T cells in which the TCR is composed of two glycoprotein chains designated α- and β-TCR chains, the TCR in γδ T cells is made up of a γ-chain and a δ-chain. γδ T cells can play a role in immunosurveillance and immunoregulation, and were found to be an important source of IL-17 and to induce robust CD8$^+$ cytotoxic T cell response. Also included are "regulatory T cells" or "Tregs" which refer to T cells that suppress an abnormal or excessive immune response and play a role in immune tolerance. Tregs are typically transcription factor Foxp3-positive CD4$^+$ T cells and can also include transcription factor Foxp3-negative regulatory T cells that are IL-10-producing CD4$^+$ T cells.

"Therapeutically effective amount" or "effective amount" as used interchangeably herein, refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit a desired response in the individual. Example indicators of an effective therapeutic or combination of therapeutics include, for example, improved wellbeing of the patient, reduction of a tumor burden, arrested or slowed growth of a tumor, and/or absence of metastasis of cancer cells to other locations in the body.

"Transduction" refers to the introduction of a foreign nucleic acid into a cell using a viral vector.

"Treat," "treating" or "treatment" of a disease or disorder such as cancer refers to accomplishing one or more of the following: reducing the severity and/or duration of the disorder, inhibiting worsening of symptoms characteristic of the disorder being treated, limiting or preventing recurrence of the disorder in subjects that have previously had the disorder, or limiting or preventing recurrence of symptoms in subjects that were previously symptomatic for the disorder.

"Variant," "mutant" or "altered" refers to a polypeptide or a polynucleotide that differs from a reference polypeptide or a reference polynucleotide by one or more modifications, for example one or more substitutions, insertions or deletions.

The numbering of amino acid residues in the antibody constant region throughout the specification is according to the EU index as described in Kabat et al., Sequences of Proteins of Immunological Interest, 5th Ed. Public Health Service, National Institutes of Health, Bethesda, MD (1991), unless otherwise explicitly stated.

Mutations in the Ig constant regions are referred to as follows: L351Y_F405A_Y407V refers to L351Y, F405A and Y407V mutations in one immunoglobulin constant region. L351Y_F405A_Y407V/T394W refers to L351Y, F405A and Y407V mutations in the first Ig constant region and T394W mutation in the second Ig constant region, which are present in one multimeric protein.

Antibodies or antigen binding domains that target CD79B are therefore capable of delivering agents to the BCR complex. As such, CD79B targeting molecules are useful in the generation of bispecific agents to recruit naturally occurring inhibitory proteins to the BCR complex, to inhibit aberrant B cell activation. For example, a bispecific dual-affinity retargeting (DART) molecule with antigen binding domains recognizing both CD79B and the inhibitory Fc gamma receptor, CD32B, inhibits B cell activation, monitored by reduced B cell proliferation and immunoglobulin secretion. Similar bispecific molecules recognizing both CD79b and CD32B delayed the onset and reduced disease severity in a preclinical model of autoimmune arthritis, indicating that CD79b-mediated recruitment of inhibitory proteins to the BCR could provide therapeutic benefit to patients with autoimmune diseases (Veri et al., 2010, Arthritis & Rheumatism, 62: 1933-1943). CD79B-targeting bispecific antibodies or antigen binding domains could also target other inhibitory molecules expressed on the surface of B cells, including members of the Siglec family, such as CD22 or Siglec-10, which have also been demonstrated to inhibit BCR-mediated signaling (reviewed in Duan & Paulson 2020, Ann. Rev Immunol 38(1):365-369).

CD79B-targeting antibodies or antigen binding domains could also be useful in treating various forms of cancer. For example, polatuzumab vedotin, an anti-CD79b antibody-drug-conjugate is approved for treatment of diffuse large B-cell lymphoma patients (DLBCL) (reviewed in Walji 2020, PMID: 32700586; DOI: 10.1080/17474086.2020.1795828). Additionally, engineered T cells expressing chimeric antigen receptors (CAR T cells) that bind to CD79B eliminated CD79B-expressing B cell lymphoma cells in vitro and in vivo (Ding 2020, PMID: 32495161 DOI: 10.1007/s11523-020-00729-7; Jiang 2020, PMID: 31624374 DOI: 10.1038/s41375-019-0607-5; Ormhøj2019, PMID: 31439577 PMCID: PMC6891163 DOI: 10.1158/1078-0432.CCR-19-1337).

Antibodies

In some embodiments, the disclosure provides antibodies that bind to CD79b, binding fragments thereof, polynucleotides encoding the foregoing, vectors, host cells and methods of making and using the foregoing. In some embodiments, the disclosure provides antibodies that bind to CD22, binding fragments thereof, polynucleotides encoding the foregoing, vectors, host cells and methods of making and using the foregoing. In some embodiments, the antibody comprises an antigen binding domains that bind CD79b or CD22. In some embodiments, the antigen binding domains may be engineered into scFv (including a stapled scFv (spFv)), Fab, F(ab')$_2$, Fd or Fv format.

In one aspect, the disclosure provides a composition comprising an antigen binding domain that binds CD22. For example, in certain embodiments, the disclosure comprises an antibody comprising an antigen binding domain that binds CD22 (i.e., a CD22-binding domain). In some embodiments, the CD22-binding domain comprises heavy chain complementarity determining region (HCDR) 1, HCDR2 and an HCDR3. In one embodiment, the CD22-binding arm comprises an HCDR1 of SEQ ID NO: 1. In one embodiment, the CD22-binding domain comprises an HCDR2 of SEQ ID NO: 2. In one embodiment, the CD22-binding domain comprises an HCDR3 of SEQ ID NO: 3. In one embodiment, the CD22-binding domain comprises an HCDR1, HCDR, and HCDR3 of SEQ ID NOs: 1, 2, and 3, respectively.

In some embodiments, the CD22-binding domain comprises light chain complementarity determining region (LCDR) 1, LCDR2 and an LCDR3. In one embodiment, the CD22-binding domain comprises an LCDR1 of SEQ ID NO: 4. In one embodiment, the CD22-binding domain comprises an LCDR2 of SEQ ID NO: 5. In one embodiment, the CD22-binding domain comprises an LCDR3 of SEQ ID NO: 6. In one embodiment, the CD22-binding domain comprises an LCDR1, LCDR2, and LCDR3 of SEQ ID NOs: 4, 5, and 6, respectively.

In some embodiments, the CD22-binding domain comprises an HCDR1, an HCDR, an HCDR3, a LCDR1, a LCDR, and a LCDR3 of SEQ ID NOs: 1, 2, 3, 4, 5, and 6, respectively.

In some embodiments, the CD22-binding domain comprises a heavy chain variable domain (VH) of SEQ ID NO:7. In some embodiments, the CD22-binding domain comprises a light chain variable domain (VL) of SEQ ID NO:8.

In some embodiments, the CD22-binding domain comprises an HCDR1 of SEQ ID NO:1, an HCDR2 of SEQ ID NO:2, an HCDR3 of SEQ ID NO:3 and a VL of SEQ ID NO:8. In some embodiments, the CD22-binding domain comprises VH of SEQ ID NO:7, an LCDR1 of SEQ ID NO:4, an LCDR2 of SEQ ID NO:5, and an LCDR3 of SEQ ID NO:6.

In some embodiments, the CD22-binding domain comprises a VH of SEQ ID NO:7 and a VL of SEQ ID NO:8.

In some embodiments, the antibody comprising the CD22-binding domain is a scFv.

In some embodiments, the antibody comprising the CD22-binding domain is a (scFv)$_2$.

In some embodiments, the antibody comprising the CD22-binding domain is a Fv.

In some embodiments, the antibody comprising the CD22-binding domain is a Fab.

In some embodiments, the antibody comprising the CD22-binding domain is a F(ab')$_2$.

In some embodiments, the antibody comprising the CD22-binding domain is a Fd.

In some embodiments, the antibody comprising the CD22-binding domain is a dAb.

In some embodiments, the antibody comprising the CD22-binding domain is a VHH

In one aspect, the disclosure provides a composition comprising an antigen binding domain that binds CD79b. For example, in certain embodiments, the disclosure comprises an antibody comprising an antigen binding domain that binds CD79b (i.e., a CD79b-binding domain). In some embodiments, the CD79b-binding domain comprises an HCDR1, an HCDR2 and an HCDR3. In one embodiment, the CD79b-binding domain comprises an HCDR1 of SEQ ID NO: 9, 17, 25, 33, 41, 49 or 57. In one embodiment, the CD79b-binding domain comprises an HCDR2 of SEQ ID NO: 10, 18, 26, 34, 42, 50 or 58. In one embodiment, the CD79b-binding domain comprises an HCDR3 of SEQ ID NO: 11, 19, 27, 35, 43, 51 or 59.

In one embodiment, the CD79b-binding domain comprises an HCDR1 of SEQ ID NO: 9, 17, 25, 33, 41, 49 or 57, an HCDR2 of SEQ ID NO: 10, 18, 26, 34, 42, 50 or 58, and HCDR3 of SEQ ID NO: 11, 19, 27, 35, 43, 51 or 59. In one embodiment, the CD79b-binding domain comprises an HCDR1, HCDR2, and HCDR3 of:
SEQ ID NOs: 9, 10, and 11, respectively;
SEQ ID NOs: 17, 18, and 19, respectively;
SEQ ID NOs: 25, 26, and 27, respectively;
SEQ ID NOs: 33, 34, and 35, respectively;
SEQ ID NOs: 41, 42, and 43, respectively;
SEQ ID NOs: 49, 50, and 51, respectively; or
SEQ ID NOs: 57, 58, and 59, respectively.

In some embodiments, the CD79b-binding domain comprises an LCDR1, an LCDR2 and an LCDR3. In one embodiment, the CD79b-binding domain comprises an LCDR1 of SEQ ID NO: 12, 20, 28, 36, 44, 52 or 60. In one embodiment, the CD79b-binding domain comprises an LCDR2 of SEQ ID NO: 13, 21, 29, 37, 45, 53 or 61. In one embodiment, the CD79b-binding domain comprises an LCDR3 of SEQ ID NO: 14, 22, 30, 38, 46, 54 or 62. In one embodiment, the CD79b-binding domain comprises an LCDR1, LCDR2, and LCDR3 of:
SEQ ID NOs: 12, 13, and 14, respectively;
SEQ ID NOs: 20, 21, and 22, respectively;
SEQ ID NOs: 28, 29, and 30, respectively;
SEQ ID NOs: 36, 37, and 38, respectively;
SEQ ID NOs: 44, 45, and 46, respectively;
SEQ ID NOs: 52, 53, and 54, respectively; or
SEQ ID NOs: 60, 61, and 62, respectively.

In some embodiments, the CD79b-binding domain comprises an HCDR1, an HCDR2, an HCDR3, an LCDR1, an LCDR2 and an LCDR3. In one embodiment, the CD79b-binding domain comprises an HCDR1 of SEQ ID NO: 9, 17, 25, 33, 41, 49 or 57. In one embodiment, the CD79b-binding domain comprises an HCDR2 of SEQ ID NO: 10, 18, 26, 34, 42, 50 or 58. In one embodiment, the CD79b-binding domain comprises an HCDR3 of SEQ ID NO: 11, 19, 27, 35, 43, 51 or 59. In one embodiment, the CD79b-binding domain comprises an LCDR1 of SEQ ID NO: 12, 20, 28, 36, 44, 52 or 60. In one embodiment, the CD79b-binding domain comprises an LCDR2 of SEQ ID NO: 13, 21, 29, 37, 45, 53 or 61. In one embodiment, the CD79b-binding domain comprises an LCDR3 of SEQ ID NO: 14, 22, 30, 38, 46, 54 or 62. In one embodiment, the CD79b-binding domain comprises an HCDR1, an HCDR2, an HCDR3, an LCDR1, LCDR2, and LCDR3 of:
SEQ ID NOs: 9, 10, 11, 12, 13, and 14, respectively;
SEQ ID NOs: 17, 18, 19, 20, 21, and 22, respectively;
SEQ ID NOs: 25, 26, 27, 28, 29, and 30, respectively;
SEQ ID NOs: 33, 34, 35, 36, 37, and 38, respectively;
SEQ ID NOs: 41, 42, 43, 44, 45, and 46, respectively;
SEQ ID NOs: 49, 50, 51, 52, 53, and 54, respectively; or
SEQ ID NOs: 57, 58, 59, 60, 61, and 62, respectively.

In one embodiment, the CD79b-binding domain comprises a VH. In one embodiment, the CD79b-binding domain comprises a VH of SEQ ID NOs: 15, 23, 31, 39, 47, 55, 63 or 80. In one embodiment, the CD79b-binding domain comprises a VL. In one embodiment, the CD79b-binding domain comprises an VL of SEQ ID NOs: 16, 24, 32, 40, 48, 56, 64 or 81.

In one embodiment, the CD79b-binding domain comprises an HCDR1 of SEQ ID NO: 9, 17, 25, 33, 41, 49 or 57, an HCDR2 of SEQ ID NO: 10, 18, 26, 34, 42, 50 or 58, HCDR3 of SEQ ID NO: 11, 19, 27, 35, 43, 51 or 59 and a VL of SEQ ID NOs: 16, 24, 32, 40, 48, 56, 64 or 81.

In one embodiment, the CD79b-binding domain comprises a VH of SEQ ID NOs: 15, 23, 31, 39, 47, 55, 63 or 80; an LCDR1 of SEQ ID NO: 12, 20, 28, 36, 44, 52 or 60; an LCDR2 of SEQ ID NO: 13, 21, 29, 37, 45, 53 or 61; and an LCDR3 of SEQ ID NO: 14, 22, 30, 38, 46, 54 or 62.

In one embodiment, the CD79b-binding domain comprises an VH and a VL. In one embodiment, the CD79b-binding domain comprises a VH and a VL of:
SEQ ID NOs: 15 and 16, respectively;
SEQ ID NOs: 23 and 24, respectively;
SEQ ID NOs: 31 and 32, respectively;
SEQ ID NOs: 39 and 40, respectively;
SEQ ID NOs: 47 and 48, respectively;
SEQ ID NOs: 55 and 56, respectively;
SEQ ID NOs: 63 and 64, respectively; or
SEQ ID NOs: 80 and 81, respectively.

In some embodiments, the antibody comprising a CD79b-binding domain is a scFv.
In some embodiments, the antibody comprising a CD79b-binding domain is a (scFv)$_2$.
In some embodiments, the antibody comprising a CD79b-binding domain is a Fv.
In some embodiments, the antibody comprising a CD79b-binding domain is a Fab.
In some embodiments, the antibody comprising a CD79b-binding domain is a F(ab')$_2$.
In some embodiments, the antibody comprising a CD79b-binding domain is a Fd.
In some embodiments, the antibody comprising a CD79b-binding domain is a dAb.
In some embodiments, the antibody comprising a CD79b-binding domain is a VHH.
In some embodiments, the antibody comprising a CD79b-binding domain is a stapled scFv (spFv).

In some embodiments, the CD79b-binding arm is an scFv comprising an HCDR1, an HCDR2, an HCDR3, an LCDR1, LCDR2, and LCDR3 of:
SEQ ID NOs: 9, 10, 11, 12, 13, and 14, respectively;
SEQ ID NOs: 17, 18, 19, 20, 21, and 22, respectively;
SEQ ID NOs: 25, 26, 27, 28, 29, and 30, respectively;
SEQ ID NOs: 33, 34, 35, 36, 37, and 38, respectively;
SEQ ID NOs: 41, 42, 43, 44, 45, and 46, respectively;
SEQ ID NOs: 49, 50, 51, 52, 53, and 54, respectively; or
SEQ ID NOs: 57, 58, 59, 60, 61, and 62, respectively.

In some embodiments, the CD79b-binding arm is an scFv comprising a VH. In one embodiment, the scFv CD79b-binding arm comprises a VH of SEQ ID NOs: 15, 23, 31, 39, 47, 55, 63 or 80. In one embodiment, the scFv CD79b-binding arm comprises a VL. In one embodiment, the scFv CD79b-binding arm comprises an VL of SEQ ID NOs: 16, 24, 32, 40, 48, 56, 64 or 81.

In one embodiment, the scFv CD79b-binding arm comprises an HCDR1 of SEQ ID NO: 9, 17, 25, 33, 41, 49 or 57, an HCDR2 of SEQ ID NO: 10, 18, 26, 34, 42, 50 or 58, HCDR3 of SEQ ID NO: 11, 19, 27, 35, 43, 51 or 59 and a VL of SEQ ID NOs: 16, 24, 32, 40, 48, 56, 64 or 81.

In one embodiment, the scFv CD79b-binding arm comprises a VH of SEQ ID NOs: 15, 23, 31, 39, 47, 55, 63 or 80; an LCDR1 of SEQ ID NO: 12, 20, 28, 36, 44, 52 or 60; an LCDR2 of SEQ ID NO: 13, 21, 29, 37, 45, 53 or 61; and an LCDR3 of SEQ ID NO: 14, 22, 30, 38, 46, 54 or 62.

In some embodiments, the CD79b-binding arm is a stapled scFv (spFv) comprising a VH and VL. In one embodiment, the spFv CD79b-binding arm comprises a VH of SEQ ID NO: 80 and a VL of SEQ ID NO:81. In one embodiment, the spFv CD79b-binding arm comprises the VH and VL and linker of SEQ ID NO:82. In one embodiment, the spFv CD79b-binding arm comprises SEQ ID NO:79.

In one embodiment, the disclosure provides multispecific antibodies that bind to CD79b and CD22, multispecific binding fragments thereof, polynucleotides encoding the foregoing, vectors, host cells and methods of making and using the foregoing. Such antibodies or antibody fragments may allow for more specific targeting to particular subsets of cells as compared to antibodies targeting only one these targets.

In some embodiments, provided herein are bispecific antibodies that bind to CD79b and CD22, and bispecific binding fragments thereof. This can be achieved by, for example, making a molecule which comprises a first region binding specifically to CD79b, and a second binding region binding specifically to CD22. The antigen-binding regions can take any form that allows specific recognition of the target, for example the binding region may be or may include a heavy chain variable domain, an Fv (combination of a heavy chain variable domain and a light chain variable domain), an single-chain Fv (scFv), an Fab, a binding domain based on a fibronectin type III domain (such as from fibronectin, or based on a consensus of the type III domains from fibronectin, or from tenascin or based on a consensus of the type III domains from tenascin, such as the Centyrin molecules from Janssen Biotech, Inc., see e.g. WO2010/051274 and WO2010/093627). Accordingly, bispecific molecules comprising two different antigen-binding regions which bind CD79b and CD22, respectively, are provided.

In some embodiments, the CD79b×CD22-multispecific antibody comprises a first antigen-binding arm comprising a first antigen-binding site that binds a first antigen and a second antigen-binding arm comprising a second antigen-binding site that binds a second antigen. The first and second antigen-binding arm may each comprise a Fragment crystallizable (Fc) domain comprising a CH2-CH3 domain.

In some embodiments, the CD79b×CD22 bispecific antibody comprises a CD79b-specific arm comprising a first antigen-binding arm that comprises a first antigen-binding site that binds CD79b and a CD22-specific arm comprising a second antigen-binding arm that comprises a second antigen-binding site that binds CD22. In some embodiments, the CD79b×CD22 bispecific antibody comprises a CD22-specific arm comprising an antigen-binding site that binds CD22 and a CD79b-specific arm comprising an antigen-binding site that binds CD79b.

In some embodiments, the first antigen-binding site comprises a single-chain variable fragment (scFv). In some embodiments, the first antigen-binding site comprises a stapled single-chain variable fragment (spFv). In some embodiments, the first antigen-binding site comprises an antigen-binding fragment (Fab). In some embodiments, the second antigen-binding site comprises an antigen-binding fragment (Fab). In some embodiments, the second antigen-binding site comprises a single-chain variable fragment (scFv). In some embodiments, the second antigen-binding site comprises a stapled single-chain variable fragment (spFv).

In some embodiments, the CD79b×CD22-multispecific antibody comprises a first antigen-binding arm that comprises an scFv comprising a variable heavy (VH1) and variable light (VL1) domain that form an antigen-binding site that binds a first antigen and a second antigen-binding arm that comprises a Fab comprising a variable heavy (VH2) and variable light (VL2) domain that form a second antigen-binding site that binds a second antigen. The first and second antigen-binding arm may each comprise a Fragment crystallizable (Fc) domain.

In one embodiment, the CD79b-binding arm comprises an antigen-binding fragment (Fab), and the CD22-binding arm comprises a single-chain variable fragment (scFv).

In one embodiment, the CD22-binding arm comprises an antigen-binding fragment (Fab), and the CD79b-binding arm comprises a single-chain variable fragment (scFv).

In one embodiment, the CD22-binding arm comprises an antigen-binding fragment (Fab), and the CD79b-binding arm comprises a stapled single-chain variable fragment (spFv).

In some embodiments, the multispecific antibodies of the disclosure include antibodies having a full length antibody structure. "Full length antibody" as used herein refers to an antibody having two full length antibody heavy chains and two full length antibody light chains. A full length antibody heavy chain (HC) includes heavy chain variable and constant domains VH, CH1, CH2, and CH3. A full length antibody light chain (LC) includes light chain variable and constant domains VL and CL. The full length antibody may be lacking the C-terminal lysine (K) in either one or both heavy chains. The term "Fab-arm" or "half molecule" refers to one heavy chain-light chain pair that binds an antigen. In some embodiments, one of the antigen-binding domains is a non-antibody based binding domain, e.g. a binding domain of based on a fibronectin type 3 domain, e.g. Centyrin.

CD22-Binding Arm

In one embodiment, multispecific antibodies described herein comprise an antigen-binding site specific for CD22. In some embodiments, the CD22-binding arm binds human CD22. In some embodiments, the CD22-binding arm binds bind to an epitope including one or more residues from the CD22 extracellular domain (ECD). Such CD22-binding arms may bind to CD22 with an affinity of $5\times10^{-7}$M or less, such as $1\times10^{-7}$M or less, $5\times10^{-8}$M or less, $1\times10^{-8}$M or less, $5\times10^{-9}$M or less, $1\times10^{-9}$M, or $5\times10^{10}$ M or less. In one embodiment, the CD22-binding arm binds to the CD22 with an affinity of about $1\times10^{-11}$M to $1\times10^{-9}$M. In one embodiment, the CD22-binding arm binds to the CD22 with an affinity of about $1\times10^{-11}$M, about $2\times10^{-11}$M, about $3\times10^{-11}$M, about $4\times10^{-11}$M, about $5\times10^{-11}$M, about $6\times10^{-11}$M, about $7\times10^{-11}$M, about $8\times10^{-11}$M, about $9\times10^{-11}$M, $1\times10^{-10}$ M, about $2\times10^{-10}$ M, about $3\times10^{-10}$ M, about $4\times10^{-10}$ M, about $5\times10^{-10}$ M, about $6\times10^{-10}$ M, about $7\times10^{-10}$ M, about $8\times10^{-10}$ M, about $9\times10^{-10}$ M or about $1\times10^{-9}$M.

In some embodiments, the CD22-binding arm comprises heavy chain complementarity determining region (HCDR) 1, HCDR2 and an HCDR3. In one embodiment, the CD22-binding arm comprises an HCDR1 of SEQ ID NO: 1. In one embodiment, the CD22-binding arm comprises an HCDR2 of SEQ ID NO: 2. In one embodiment, the CD22-binding arm comprises an HCDR3 of SEQ ID NO: 3. In one embodiment, the CD22-binding arm comprises an HCDR1, HCDR, and HCDR3 of SEQ ID NOs: 1, 2, and 3, respectively.

In some embodiments, the CD22-binding arm comprises light chain complementarity determining region (LCDR) 1, LCDR2 and an LCDR3. In one embodiment, the CD22-binding arm comprises an LCDR1 of SEQ ID NO: 4. In one embodiment, the CD22-binding arm comprises an LCDR2 of SEQ ID NO: 5. In one embodiment, the CD22-binding arm comprises an LCDR3 of SEQ ID NO: 6. In one embodiment, the CD22-binding arm comprises an LCDR1, LCDR2, and LCDR3 of SEQ ID NOs: 4, 5, and 6, respectively.

In some embodiments, the CD22-binding arm comprises an HCDR1, an HCDR, an HCDR3, a LCDR1, a LCDR, and a LCDR3 of SEQ ID NOs: 1, 2, 3, 4, 5, and 6, respectively.

In some embodiments, the CD22-binding arm comprises a heavy chain variable domain (VH) of SEQ ID NO:7. In some embodiments, the CD22-binding arm comprises a light chain variable domain (VL) of SEQ ID NO:8.

In some embodiments, the CD22-binding arm comprises an HCDR1 of SEQ ID NO:1, an HCDR2 of SEQ ID NO:2, an HCDR3 of SEQ ID NO:3 and a VL of SEQ ID NO:8. In some embodiments, the CD22-binding arm comprises VH of SEQ ID NO:7, an LCDR1 of SEQ ID NO:4, an LCDR2 of SEQ ID NO:5, and an LCDR3 of SEQ ID NO:6.

In some embodiments, the CD22-binding arm comprises a VH of SEQ ID NO:7 and a VL of SEQ ID NO:8.

In some embodiments, the CD22-binding arm is a scFv.
In some embodiments, the CD22-binding arm is a (scFv)$_2$.
In some embodiments, the CD22-binding arm is a Fv.
In some embodiments, the CD22-binding arm is a Fab.
In some embodiments, the CD22-binding arm is a F(ab')$_2$.
In some embodiments, the CD22-binding arm is a Fd.
In some embodiments, the CD22-binding arm is a dAb.
In some embodiments, the CD22-binding arm is a VHH In some embodiments, the CD22-binding arm comprises humanized antigen-binding fragments. Humanized antigen-binding fragments may be derived from chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies or antigen-binding fragments are human immunoglobulins (recipient antibody) or antigen-binding fragments in which residues from a complementary-determining region (CDR) of the recipient are replaced by residues from a CDR of a non-human species (donor antibody) such as mouse, rat or rabbit having the desired specificity, affinity, and capacity. In general, the humanized antibody antigen-binding fragments will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody antigen-binding fragments may include at least a portion of an immunoglobulin constant region (Fc), typically that of a human immunoglobulin.

In some embodiments, the CD22-binding arm comprises a scFv. In some embodiments, the CD22-binding arm comprises a (scFv)$_2$. In some embodiments, the CD22-binding arm comprises a Fv. In some embodiments, the CD22-binding arm comprises a Fab. In some embodiments, the CD22-binding arm comprises a F(ab')$_2$. In some embodiments, the CD22-binding arm comprises a Fd. In some embodiments, the CD22-binding arm comprises a dAb. In some embodiments, the CD22-binding arm comprises a VHH.

In some embodiments, the CD22-binding arm is IgG, or a derivative thereof. In some embodiments, the CD22-binding arm is IgG1, IgG2, IgG3, or IgG4. In some embodiments where in the CD22-binding arm has an IgG4 isotype, it contains S228P, L234A, L235A, F405L, and R409K substitution(s) in its Fc region.

In some embodiments, the CD22-binding arm comprises an Fc domain. In one embodiment, the Fc domain comprises at least one mutation to promote heterodimerization, reduce Fc binding to a Fcγ receptor, reduce Fc binding to protein A, extend the half-life of the mutispecific binding molecule, or any combination thereof. Exemplary mutations for promoting heterodimerization include, but are not limited to, T366W, T366S, L368A, and Y407V. Exemplary mutations for reducing Fc binding to a Fcγ receptor include, but are not limited to, L234A, L235A, and D265S. Exemplary mutations for reducing Fc binding to protein A include, but are not limited to, H435R and Y436F. Exemplary mutations for extending the half-life include, but are not limited to, M252Y, S254T, and T256E.

In some embodiments, the CD22-binding arm comprises an Fc domain comprising SEQ ID NO:85 or a derivative thereof. In some embodiments, the CD22-binding arm comprises an derivative of an Fc domain comprising at least one of a L234A, L235A, D265S, M252Y, S254T, T256E, T366S, L368A, Y407V, H435R and Y436F substitution. In some embodiments, the CD22-binding arm comprises an derivative of an Fc domain comprising each of a L234A, L235A, D265S, M252Y, S254T, T256E, T366S, L368A, Y407V, H435R and Y436F substitution. In one embodiment, the multispecific antibody comprises the variant IgG set forth in SEQ ID NO:90.

CD79b-Binding Arm

In one embodiment, multispecific antibodies described herein comprise an antigen-binding site specific for CD79b. In some embodiments, the CD79b-binding arm binds human CD79b. In some embodiments, the CD79b-binding arm binds human CD79b and *Cynomolgus* monkey CD79b. In some embodiments, the CD79b-binding arm binds human CD79b but not to *Cynomolgus* monkey CD79b. In some embodiments, the CD79b-binding arm binds bind to an epitope including one or more residues from the CD79b extracellular domain (ECD). Such CD79b-binding arms may bind to CD79b with an affinity of $5 \times 10^{-7}$M or less, such as $1 \times 10^{-7}$M or less, $5 \times 10^{-8}$M or less, $1 \times 10^{-8}$M or less, $5 \times 10^{-9}$M or less, $1 \times 10^{-9}$M, or $5 \times 10^{-10}$ M or less. In one embodiment, the CD79b-binding arm binds to the CD79b with an affinity of about $1 \times 10^{-11}$M to $1 \times 10^{-9}$M. In one embodiment, the CD79b-binding arm binds to the CD79b with an affinity of about $1 \times 10^{-11}$M, about $2 \times 10^{-11}$M, about $3 \times 10^{-11}$M, about $4 \times 10^{-11}$M, about $5 \times 10^{-11}$M, about $6 \times 10^{-11}$M, about $7 \times 10^{-11}$M, about $8 \times 10^{-11}$M, about $9 \times 10^{-11}$M, $1 \times 10^{-10}$M, about $2 \times 10^{-10}$M, about $3 \times 10^{-10}$M, about $4 \times 10^{-10}$M, about $5 \times 10^{-10}$M, about $6 \times 10^{-10}$M, about $7 \times 10^{-10}$M, about $8 \times 10^{-10}$M, about $9 \times 10^{-10}$M or about $1 \times 10^{-9}$M.

In some embodiments, the CD79b-binding arm comprises an HCDR1, an HCDR2 and an HCDR3. In one embodiment, the CD79b-binding arm comprises an HCDR1 of SEQ ID NO: 9, 17, 25, 33, 41, 49 or 57. In one embodiment, the CD79b-binding arm comprises an HCDR2 of SEQ ID NO: 10, 18, 26, 34, 42, 50 or 58. In one embodiment, the CD79b-binding arm comprises an HCDR3 of SEQ ID NO: 11, 19, 27, 35, 43, 51 or 59.

In one embodiment, the CD79b-binding arm comprises an HCDR1 of SEQ ID NO: 9, 17, 25, 33, 41, 49 or 57, an HCDR2 of SEQ ID NO: 10, 18, 26, 34, 42, 50 or 58, and HCDR3 of SEQ ID NO: 11, 19, 27, 35, 43, 51 or 59. In one embodiment, the CD79b-binding arm comprises an HCDR1, HCDR2, and HCDR3 of:

SEQ ID NOs: 9, 10, and 11, respectively;
SEQ ID NOs: 17, 18, and 19, respectively;
SEQ ID NOs: 25, 26, and 27, respectively;
SEQ ID NOs: 33, 34, and 35, respectively;
SEQ ID NOs: 41, 42, and 43, respectively;
SEQ ID NOs: 49, 50, and 51, respectively; or
SEQ ID NOs: 57, 58, and 59, respectively.

In some embodiments, the CD79b-binding arm comprises an LCDR1, an LCDR2 and an LCDR3. In one embodiment, the CD79b-binding arm comprises an LCDR1 of SEQ ID NO: 12, 20, 28, 36, 44, 52 or 60. In one embodiment, the CD79b-binding arm comprises an LCDR2 of SEQ ID NO: 13, 21, 29, 37, 45, 53 or 61. In one embodiment, the CD79b-binding arm comprises an LCDR3 of SEQ ID NO: 14, 22, 30, 38, 46, 54 or 62. In one embodiment, the CD79b-binding arm comprises an LCDR1, LCDR2, and LCDR3 of:

SEQ ID NOs: 12, 13, and 14, respectively;
SEQ ID NOs: 20, 21, and 22, respectively;
SEQ ID NOs: 28, 29, and 30, respectively;
SEQ ID NOs: 36, 37, and 38, respectively;
SEQ ID NOs: 44, 45, and 46, respectively;
SEQ ID NOs: 52, 53, and 54, respectively; or
SEQ ID NOs: 60, 61, and 62, respectively.

In some embodiments, the CD79b-binding arm comprises an HCDR1, an HCDR2, an HCDR3, an LCDR1, an LCDR2 and an LCDR3. In one embodiment, the CD79b-binding arm comprises an HCDR1 of SEQ ID NO: 9, 17, 25, 33, 41, 49 or 57. In one embodiment, the CD79b-binding arm comprises an HCDR2 of SEQ ID NO: 10, 18, 26, 34, 42, 50 or 58. In one embodiment, the CD79b-binding arm comprises an HCDR3 of SEQ ID NO: 11, 19, 27, 35, 43, 51 or 59. In one embodiment, the CD79b-binding arm comprises an LCDR1 of SEQ ID NO: 12, 20, 28, 36, 44, 52 or 60. In one embodiment, the CD79b-binding arm comprises an LCDR2 of SEQ ID NO: 13, 21, 29, 37, 45, 53 or 61. In one embodiment, the CD79b-binding arm comprises an LCDR3 of SEQ ID NO: 14, 22, 30, 38, 46, 54 or 62. In one embodiment, the CD79b-binding arm comprises an HCDR1, an HCDR2, an HCDR3, an LCDR1, LCDR2, and LCDR3 of:

SEQ ID NOs: 9, 10, 11, 12, 13, and 14, respectively;
SEQ ID NOs: 17, 18, 19, 20, 21, and 22, respectively;
SEQ ID NOs: 25, 26, 27, 28, 29, and 30, respectively;
SEQ ID NOs: 33, 34, 35, 36, 37, and 38, respectively;
SEQ ID NOs: 41, 42, 43, 44, 45, and 46, respectively;
SEQ ID NOs: 49, 50, 51, 52, 53, and 54, respectively; or
SEQ ID NOs: 57, 58, 59, 60, 61, and 62, respectively.

In one embodiment, the CD79b-binding arm comprises a VH. In one embodiment, the CD79b-binding arm comprises a VH of SEQ ID NOs: 15, 23, 31, 39, 47, 55, 63 or 80. In one embodiment, the CD79b-binding arm comprises a VL. In one embodiment, the CD79b-binding arm comprises an VL of SEQ ID NOs: 16, 24, 32, 40, 48, 56, 64 or 81.

In one embodiment, the CD79b-binding arm comprises an HCDR1 of SEQ ID NO: 9, 17, 25, 33, 41, 49 or 57, an HCDR2 of SEQ ID NO: 10, 18, 26, 34, 42, 50 or 58, HCDR3 of SEQ ID NO: 11, 19, 27, 35, 43, 51 or 59 and a VL of SEQ ID NOs: 16, 24, 32, 40, 48, 56, 64 or 81.

In one embodiment, the CD79b-binding arm comprises a VH of SEQ ID NOs: 15, 23, 31, 39, 47, 55, 63 or 80; an LCDR1 of SEQ ID NO: 12, 20, 28, 36, 44, 52 or 60; an LCDR2 of SEQ ID NO: 13, 21, 29, 37, 45, 53 or 61; and an LCDR3 of SEQ ID NO: 14, 22, 30, 38, 46, 54 or 62.

In one embodiment, the CD79b-binding arm comprises an VH and a VL. In one embodiment, the CD79b-binding arm comprises a VH and a VL of:

SEQ ID NOs: 15 and 16, respectively;
SEQ ID NOs: 23 and 24, respectively;
SEQ ID NOs: 31 and 32, respectively;
SEQ ID NOs: 39 and 40, respectively;
SEQ ID NOs: 47 and 48, respectively;
SEQ ID NOs: 55 and 56, respectively;
SEQ ID NOs: 63 and 64, respectively; or
SEQ ID NOs: 80 and 81, respectively.

In some embodiments, the CD79b-binding arm is a scFv.
In some embodiments, the CD79b-binding arm is a (scFv)$_2$.
In some embodiments, the CD79b-binding arm is a Fv.
In some embodiments, the CD79b-binding arm is a Fab.
In some embodiments, the CD79b-binding arm is a F(ab')$_2$.
In some embodiments, the CD79b-binding arm is a Fd.
In some embodiments, the CD79b-binding arm is a dAb.
In some embodiments, the CD79b-binding arm is a VHH
In some embodiments, the CD79b-binding arm is a stapled scFv (spFv).

In some embodiments, the CD79b-binding arm is an scFv comprising an HCDR1, an HCDR2, an HCDR3, an LCDR1, LCDR2, and LCDR3 of:

SEQ ID NOs: 9, 10, 11, 12, 13, and 14, respectively;
SEQ ID NOs: 17, 18, 19, 20, 21, and 22, respectively;
SEQ ID NOs: 25, 26, 27, 28, 29, and 30, respectively;
SEQ ID NOs: 33, 34, 35, 36, 37, and 38, respectively;
SEQ ID NOs: 41, 42, 43, 44, 45, and 46, respectively;
SEQ ID NOs: 49, 50, 51, 52, 53, and 54, respectively; or
SEQ ID NOs: 57, 58, 59, 60, 61, and 62, respectively.

In some embodiments, the CD79b-binding arm is an scFv comprising a VH. In one embodiment, the scFv CD79b-binding arm comprises a VH of SEQ ID NOs: 15, 23, 31, 39, 47, 55, 63 or 80. In one embodiment, the scFv CD79b-binding arm comprises a VL. In one embodiment, the scFv CD79b-binding arm comprises an VL of SEQ ID NOs: 16, 24, 32, 40, 48, 56, 64 or 81.

In one embodiment, the scFv CD79b-binding arm comprises an HCDR1 of SEQ ID NO: 9, 17, 25, 33, 41, 49 or 57, an HCDR2 of SEQ ID NO: 10, 18, 26, 34, 42, 50 or 58, HCDR3 of SEQ ID NO: 11, 19, 27, 35, 43, 51 or 59 and a VL of SEQ ID NOs: 16, 24, 32, 40, 48, 56, 64 or 81.

In one embodiment, the scFv CD79b-binding arm comprises a VH of SEQ ID NOs: 15, 23, 31, 39, 47, 55, 63 or 80; an LCDR1 of SEQ ID NO: 12, 20, 28, 36, 44, 52 or 60; an LCDR2 of SEQ ID NO: 13, 21, 29, 37, 45, 53 or 61; and an LCDR3 of SEQ ID NO: 14, 22, 30, 38, 46, 54 or 62.

In some embodiments, the CD79b-binding arm is a stapled scFv comprising a VH. In one embodiment, the stapled scFv CD79b-binding arm comprises a VH of SEQ ID NO: 80 and a VL of SEQ ID NO:81. In one embodiment, the stapled scFv CD79b-binding arm comprises the VH and VL and linker of SEQ ID NO:82. In one embodiment, the stapled scFv CD79b-binding arm comprises SEQ ID NO:79.

In some embodiments, the CD79b-binding arm comprises humanized antigen-binding fragments. Humanized antigen-binding fragments may be derived from chimeric immunoglobulins, immunoglobulin chains or fragments thereof (such as Fv, Fab, Fab', F(ab')$_2$ or other antigen-binding subsequences of antibodies) that contain minimal sequence derived from non-human immunoglobulin. For the most part, humanized antibodies or antigen-binding fragments are human immunoglobulins (recipient antibody) or antigen-binding fragments in which residues from a complementary-determining region (CDR) of the recipient are replaced by residues from a CDR of a non-human species (donor antibody) such as mouse, rat or rabbit having the desired specificity, affinity, and capacity. In general, the humanized antibody antigen-binding fragments will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody antigen-binding fragments may include at least a portion of an immunoglobulin constant region (Fc), typically that of a human immunoglobulin.

In some embodiments, the CD79b-binding arm comprises a scFv, for example, a spFv. In some embodiments, the CD79b-binding arm comprises a (scFv)$_2$. In some embodiments, the CD79b-binding arm comprises a Fv. In some embodiments, the CD79b-binding arm comprises a Fab. In some embodiments, the CD79b-binding arm comprises a F(ab')$_2$. In some embodiments, the CD79b-binding arm comprises a Fd. In some embodiments, the CD79b-binding arm comprises a dAb. In some embodiments, the CD79b-binding arm comprises a VHH.

In some embodiments, the CD79b-binding arm is IgG, or a derivative thereof. In some embodiments, the CD79b-binding arm is IgG1, IgG2, IgG3, or IgG4. In some embodiments wherein the CD79b-binding arm has an IgG4 isotype, it contains S228P, L234A, L235A, F405L, and R409K substitution(s) in its Fc region.

In some embodiments, the CD79b-binding arm comprises an Fc domain. In one embodiment, the Fc domain comprises at least one mutation to promote heterodimerization, reduce Fc binding to a Fcγ receptor, reduce Fc binding to protein A, extend the half-life of the mutispecific binding molecule, or any combination thereof. Exemplary mutations for promoting heterodimerization include, but are not limited to, T366W, T366S, L368A, and Y407V. Exemplary mutations for reducing Fc binding to a Fcγ receptor include, but are not limited to, L234A, L235A, and D265S. Exemplary mutations for reducing Fc binding to protein A include, but are not limited to, H435R and Y436F. Exemplary mutations for extending the half-life include, but are not limited to, M252Y, S254T, and T256E.

In some embodiments, the CD79b-binding arm comprises SEQ ID NO:88 or a derivative thereof. In one embodiment, the multispecific antibody comprises the Fc domain set forth in SEQ ID NO:89.

Antibodies and Antibody Fragments

The CD79b and/or CD22 binding arms of the disclosure may be engineered into monospecific or multispecific proteins of various designs using standard methods. The disclosure also provides a monospecific protein comprising the antigen binding domain that binds CD79b and/or CD22 of the disclosure. In some embodiments, the monospecific protein is an antibody. In some embodiments, the multispecific protein is an antibody While not being limited by this approach, in general when constructing antibodies as multi-specific antibodies, the binding domain modules to each target (first, second, third etc.) are optional built from scFv, Fab, Fab', F(ab')$_2$, Fv, variable domain (e.g. VH or VL), diabody, minibody or full length antibodies. For example, each said binding domain or module is created in one or more of the following non-limiting formats wherein binding domains comprising variable domains, and/or full length antibodies, and/or antibody fragments, are operatively linked in series to generate multi-specific antibodies. In some embodiments, the multispecific protein is bispecific.

In one embodiment there is provided a multi-specific antibody comprising at least one first antibody-derived binding domain targeting CD79b and which is operatively linked to at least one second antibody binding domain targeting a CD22. Optionally, the binding domains comprise at least one or more VH and cognate VL binding domain, or one or more VH-CH1-CH2-CH2 and cognate VL-CL binding domain, or one or more antibody fragment binding domains.

Any of the VH and the VL domains identified herein that bind CD79b or CD22 may also be engineered into scFv, Fab, F(ab')$_2$, Fd or Fv format and their binding to CD79b or CD22 may be assessed using the assays described herein.

For example, any of the VH and the VL domains identified herein that bind CD79b or CD22 may be engineered into scFv format in either VH-linker-VL or VL-linker-VH orientation. In some embodiments, the scFv format is in either VH-linker-VL or VL-linker-VH orientation. Any of the VH and the VL domains identified herein may also be used to generate sc(Fv)$_2$ structures, such as VH-linker-VL-linker-VL-linker-VH, VH-linker-VL-linker-VH-linker-VL. VH-linker-VH-linker-VL-linker-VL. VL-linker-VH-linker-VH-linker-VL. VL-linker-VH-linker-VL-linker-VH or VL-linker-VL-linker-VH-linker-VH.

VH and the VL domains identified herein may be incorporated into a scFv format and the binding and thermostability of the resulting scFv to CD79b or CD22 may be assessed using known methods. Binding may be assessed using ProteOn XPR36, Biacore 3000 or KinExA instrumentation, ELISA or competitive binding assays known to those skilled in the art. Binding may be evaluated using purified scFvs or *E. coli* supernatants or lysed cells containing the expressed scFv. The measured affinity of a test scFv to CD79b or CD22 may vary if measured under different conditions (e.g., osmolarity, pH). Thus, measurements of affinity and other binding parameters (e.g., $K_D$, $K_{on}$, $K_{off}$) are typically made with standardized conditions and standardized buffers. Thermostability may be evaluated by heating the test scFv at elevated temperatures, such as at 50° C., 55° C. or 60° C. for a period of time, such as 5 minutes (min), 10 min, 15 min, 20 min, 25 min or 30 min and measuring binding of the test scFv to CD79b or CD22. The scFvs retaining comparable binding to CD79b or CD22 when compared to a non-heated scFv sample are referred to as being thermostable.

In recombinant expression systems, the linker is a peptide linker and may include any naturally occurring amino acid. Exemplary amino acids that may be included into the linker are Gly, Ser, Pro, Thr, Glu, Lys, Arg, Ile, Leu, His and The. The linker should have a length that is adequate to link the VH and the VL in such a way that they form the correct conformation relative to one another so that they retain the desired activity, such as binding to CD79b.

The linker may be about 5-50 amino acids long. In some embodiments, the linker is about 10-40 amino acids long. In some embodiments, the linker is about 10-35 amino acids long. In some embodiments, the linker is about 10-30 amino acids long. In some embodiments, the linker is about 10-25 amino acids long. In some embodiments, the linker is about 10-20 amino acids long. In some embodiments, the linker is about 15-20 amino acids long. In some embodiments, the linker is 6 amino acids long. In some embodiments, the linker is 7 amino acids long. In some embodiments, the linker is 8 amino acids long. In some embodiments, the linker is 9 amino acids long. In some embodiments, the linker is 10 amino acids long. In some embodiments, the linker is 11 amino acids long. In some embodiments, the linker is 12 amino acids long. In some embodiments, the linker is 13 amino acids long. In some embodiments, the linker is 14 amino acids long. In some embodiments, the linker is 15 amino acids long. In some embodiments, the linker is 16 amino acids long. In some embodiments, the linker is 17 amino acids long. In some embodiments, the linker is 18 amino acids long. In some embodiments, the linker is 19 amino acids long. In some embodiments, the linker is 20 amino acids long. In some embodiments, the linker is 21 amino acids long. In some embodiments, the linker is 22 amino acids long. In some embodiments, the linker is 23 amino acids long. In some embodiments, the linker is 24 amino acids long. In some embodiments, the linker is 25 amino acids long. In some embodiments, the linker is 26 amino acids long. In some embodiments, the linker is 27 amino acids long. In some embodiments, the linker is 28 amino acids long. In some embodiments, the linker is 29 amino acids long. In some embodiments, the linker is 30 amino acids long. In some embodiments, the linker is 31 amino acids long. In some embodiments, the linker is 32 amino acids long. In some embodiments, the linker is 33 amino acids long. In some embodiments, the linker is 34 amino acids long. In some embodiments, the linker is 35 amino acids long. In some embodiments, the linker is 36 amino acids long. In some embodiments, the linker is 37 amino acids long. In some embodiments, the linker is 38 amino acids long. In some embodiments, the linker is 39 amino acids long. In some embodiments, the linker is 40 amino acids long. Exemplary linkers that may be used are Gly rich linkers, Gly and Ser containing linkers, Gly and Ala containing linkers, Ala and Ser containing linkers, and other flexible linkers.

Other linker sequences may include portions of immunoglobulin hinge area, CL or CH1 derived from any immunoglobulin heavy or light chain isotype. Alternatively, a variety of non-proteinaceous polymers, including polyethylene glycol (PEG), polypropylene glycol, polyoxyalkylenes, or copolymers of polyethylene glycol and polypropylene glycol, may find use as linkers. Additional linkers are described for example in Int. Pat. Publ. No. WO2019/060695.

In some embodiments, the scFv comprises, from the N- to C-terminus, a VH, a first linker (L1) and a VL (VH-L1-VL). In some embodiments, the scFv comprises, from the N- to C-terminus, the VL, the L1 and the VH (VL-L1-VH).

In some embodiments, the scFv comprises, from the N- to C-terminus, a VH, a first linker (L1) and a VL (VH-L1-VL) or the VL, the L1 and the VH (VL-L1-VH). In some embodiments, the L1 comprises about 5-50 amino acids. In some embodiments, the L1 comprises about 5-40 amino acids. In some embodiments, the L1 comprises about 10-30 amino acids. In some embodiments, the L1 comprises about 10-20 amino acids. In some embodiments, the L1 comprises the amino acid sequence of SEQ ID NOs: 91-125.

Multispecific Antibodies

In some embodiments, the antigen-binding arms can be incorporated into the Dual Variable Domain Immunoglobulins (DVD) (Int. Pat. Publ. No. WO2009/134776; DVDs are full length antibodies comprising the heavy chain having a structure VH1-linker-VH2-CH and the light chain having the structure VL1-linker-VL2-CL; linker being optional), structures that include various dimerization domains to connect the two antibody arms with different specificity, such as leucine zipper or collagen dimerization domains (Int. Pat. Publ. No. WO2012/022811, U.S. Pat. Nos. 5,932,448; 6,833,441), two or more domain antibodies (dAbs) conjugated together, diabodies, heavy chain only antibodies such as camelid antibodies and engineered camelid antibodies, Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer), IgG-like Bispecific (InnClone/Eli Lilly), Ts2Ab (MedImmune/AZ) and BsAb (Zymogenetics), HERCULES (Biogen Idec) and TvAb (Roche), ScFv/Fc Fusions (Academic Institution), SCORPION (Emergent BioSolutions/Trubion, Zymogenetics/BMS), Dual Affinity Retargeting Technology (Fc-DART) (MacroGenics) and Dual(ScFv)$_2$-Fab (National Research Center for Antibody Medicine—China), Dual-Action or Bis-Fab (Genentech), Dock-and-Lock (DNL) (ImmunoMedics), Bivalent Bispecific (Biotecnol) and Fab-Fv (UCB-Celltech). ScFv-, diabody-based, and domain antibodies, include but are not limited to, Bispecific T Cell Engager (BiTE) (Micromet), Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies.

In some embodiments, the multispecific antibodies described herein may adopt any format which has been described in the art for multispecific antibodies. In some embodiments, the multispecific antibodies described herein is constructed based on a bispecific antibody format. This can be achieved by adding a third antigen-binding region to a bispecific antibody. Different formats of bispecific antibodies have been described and were recently reviewed by Chames and Baty (2009) Curr Opin Drug Disc Dev 12: 276. In some embodiments, the multispecific antibody comprises a bispecific antibody which is a diabody, a cross-body, or a bispecific antibody obtained via a controlled Fab arm exchange as those described in the present disclosure.

In some embodiments, the multispecific antibodies include IgG-like molecules with complementary CH3 domains to force heterodimerization; recombinant IgG-like dual targeting molecules, wherein the two sides of the molecule each contain the Fab fragment or part of the Fab fragment of at least two different antibodies; IgG fusion molecules, wherein full length IgG antibodies are fused to an extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

In some embodiments, IgG-like molecules with complementary CH3 domains molecules include the Triomab/Quadroma (Trion Pharma/Fresenius Biotech), the Knobs-into-Holes (Genentech), CrossMAbs (Roche) and the electrostatically-matched (Amgen), the LUZ-Y (Genentech), the Strand Exchange Engineered Domain body (SEEDbody) (EMD Serono), the Biclonic (Merus), the DuoBody (Genmab A/S), and other asymmetric mutations (e.g., Zymeworks).

In some embodiments, recombinant IgG-like dual targeting molecules include Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer).

In some embodiments, IgG fusion molecules include Dual Variable Domain (DVD)-Ig (Abbott), IgG-like Bispecific (InnClone/Eli Lilly), Ts2Ab (MedImmune/AZ) and BsAb (Zymogenetics), HERCULES (Biogen Idec) and TvAb (Roche).

In some embodiments, Fc fusion molecules include to ScFv/Fc Fusions (Academic Institution), SCORPION (Emergent BioSolutions/Trubion, Zymogenetics/BMS), Dual Affinity Retargeting Technology (Fc-DART) (MacroGenics) and Dual(ScFv)$_2$-Fab (National Research Center for Antibody Medicine—China).

In some embodiments, Fab fusion bispecific antibodies include F(ab)$_2$ (Medarex/AMGEN), Dual-Action or Bis-Fab (Genentech), Dock-and-Lock (DNL) (ImmunoMedics), Bivalent Bispecific (Biotecnol) and Fab-Fv (UCB-Celltech). ScFv-, diabody-based and domain antibodies include but are not limited to Bispecific T Cell Engager (BiTE) (Micromet), Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies.

Full length multispecific antibodies of the present disclosure may be generated for example using Fab arm exchange (or half molecule exchange) between two mono specific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy-chain disulfide bonds in the hinge regions of the parent mono specific antibodies are reduced. The resulting free cysteines of one of the parent monospecific antibodies form an inter heavychain disulfide bond with cysteine residues of a second parent mono specific antibody molecule and simultaneously CH3 domains of the parent antibodies release and reform by dissociation-association. The CH3 domains of the Fab arms may be engineered to favor heterodimerization over homodimerization. The resulting product is a bispecific antibody having two Fab arms or half molecules which each bind a distinct epitope, e.g., an epitope on CD79b and an epitope on CD22.

"Homodimerization" as used herein refers to an interaction of two heavy chains having identical CH3 amino acid sequences. "Homodimer" as used herein refers to an antibody having two heavy chains with identical CH3 amino acid sequences.

"Heterodimerization" as used herein refers to an interaction of two heavy chains having non-identical CH3 amino acid sequences. "Heterodimer" as used herein refers to an antibody having two heavy chains with non-identical CH3 amino acid sequences.

The "knob-in-hole" strategy (see, e.g., PCT Inti. Publ. No. WO 2006/028936) may be used to generate full length multispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody binding a first antigen and an amino acid with a large side chain (knob) is introduced into a heavy chain of an antibody binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

In some embodiments of the multispecific antibody or multispecific binding fragment described herein, the Fc domain of the first antigen-binding arm comprise mutations T366S, L368A and Y407V and the Fc domain of the second antigen-binding arm comprises mutation T366W. In some embodiments, the Fc domain of the second antigen-binding arm comprise mutations T366S, L368A and Y407V and the Fc domain of the first antigen-binding arm comprises mutation T366W.

Other strategies such as promoting heavy chain heterodimerization using electrostatic interactions by substituting positively charged residues at one CH3 surface and negatively charged residues at a second CH3 surface may be used, as described in US Pat. Publ. No. US2010/0015133; US Pat. Publ. No. US2009/0182127; US Pat. Publ. No. US2010/028637 or US Pat. Publ. No. US2011/0123532. In other strategies, heterodimerization may be promoted by the following substitutions (expressed as modified position in the first CH3 domain of the first heavy chain/modified position in the second CH3 domain of the second heavy chain): L351Y_F405AY407V/T394W, T366I_K392M_T394W/F405A_Y407V, T366L_K392M_T394W/F405A_Y407V, L351Y_Y407A/T366A_K409F, L351Y_Y407A/T366V_K409F_Y407A/T366A_K409F, or T350V_L351Y_F405A_Y407V/T350V_T366L_K392L_T394W as described in U.S. Pat. Publ. No. US2012/0149876 or U.S. Pat. Publ. No. US2013/0195849 (Zymeworks).

In addition to methods described above, multispecific antibodies of the invention may be generated in vitro in a cell-free environment by introducing asymmetrical mutations in the CH3 regions of two mono specific homodimeric antibodies and forming the multispecific heterodimeric antibody from two parent monospecific homodimeric antibodies in reducing conditions to allow disulfide bond isomerization according to methods described in Inti. Pat. Publ. No. WO2011/131746. In the methods, the first monospecific bivalent antibody (e.g., anti-CD79b antibody) and the second monospecific bivalent antibody (e.g., anti-CD3 antibody) are engineered to have certain substitutions at the CH3 domain that promotes heterodimer stability; the antibodies are incubated together under reducing conditions sufficient to allow the cysteines in the hinge region to undergo disulfide bond isomerization; thereby generating the multispecific antibody by Fab arm exchange. The incubation conditions may optimally be restored to non-reducing conditions. Exemplary reducing agents that may be used are 2-mercaptoethylamine (2-MEA), dithiothreitol (DTT), dithioerythritol (DTE), glutathione, tris (2-carboxyethyl) phosphine (TCEP), L-cysteine and beta-mercaptoethanol, preferably a reducing agent selected from the group consisting of: 2-mercaptoethylamine, dithiothreitol and tris (2-carboxyethyl) phosphine. For example, incubation for at least 90 min at a temperature of at least 20° C. in the presence of at least 25 mM 2-MEA or in the presence of at least 0.5 mM dithiothreitol at a pH from 5-8, for example at pH of 7.0 or at pH of 7.4 may be used.

In some embodiments, the multispecific antibodies or antigen-binding fragments are IgG, or derivatives thereof. The IgG class is divided in four isotypes: IgG1, IgG2, IgG3 and IgG4 in humans. They share more than 95% homology in the amino acid sequences of the Fc regions but show major differences in the amino acid composition and structure of the hinge region. The Fc region mediates effector functions, such as antibody-dependent cellular cytotoxicity (ADCC) and complement-dependent cytotoxicity (CDC). In ADCC, the Fc region of an antibody binds to Fc receptors (FcγRs) on the surface of immune effector cells such as natural killers and macrophages, leading to the phagocytosis or lysis of the targeted cells. In CDC, the antibodies kill the targeted cells by triggering the complement cascade at the cell surface. The antibodies described herein include antibodies with the described features of the variable domains in combination with any of the IgG isotypes, including modified versions in which the Fc sequence has been modified to effect different effector functions.

For many applications of therapeutic antibodies, Fc-mediated effector functions are not part of the mechanism of action. These Fc-mediated effector functions can be detrimental and potentially pose a safety risk by causing off-mechanism toxicity. Modifying effector functions can be achieved by engineering the Fc regions to reduce their binding to FcγRs or the complement factors. The binding of IgG to the activating (FcγRI, FcγRIIa, FcγRIIIa and FcγRIIIb) and inhibitory (FcγRIIb) FcγRs or the first component of complement (C1q) depends on residues located in the hinge region and the CH2 domain. Mutations have been introduced in IgG1, IgG2 and IgG4 to reduce or silence Fc functionalities. The antibodies described herein may include these modifications.

In one embodiment, the antibody comprises an Fc region with one or more of the following properties: (a) reduced effector function when compared to the parent Fc; (b) reduced affinity to FcγRI, FcγRIIa, FcγRIIb, FcγRIIIb and/or FcγRIIIa, (c) reduced affinity to FcγRI (d) reduced affinity to FcγRIIa (e) reduced affinity to FcγRIIb, (f) reduced affinity to FcγRIIIb or (g) reduced affinity to FcγRIIIa.

In some embodiments, the antibodies or antigen-binding fragments are IgG, or derivatives thereof, e.g., IgG1, IgG2, IgG3, and IgG4 isotypes. In some embodiments wherein the antibody has an IgG1 isotype, the antibody contains L234A, L235A, D265S and/or K409R substitution(s) in its Fc region. In some embodiments wherein the antibody has an IgG4 isotype, the antibody contains S228P, L234A, and L235A substitutions in its Fc region. The antibodies described herein may include these modifications.

In some embodiments, the Fc domains of a first and/or second antigen-binding arm of a multispecific antibody described herein each comprise one or more mutations selected from L234A, L235A, and D265S. In some embodiments, the Fc domains of first and second antigen-binding arm each comprise mutations L234A, L235A, and D265S.

In some embodiments, the Fc domains of a first or second antigen-binding arm of a multispecific antibody described herein further comprises one or more mutations which reduce Fc binding to protein A. In some embodiments, the Fc domains of a first and/or second antigen-binding arm comprises mutations H435R and/or Y436F. In some embodiments, the Fc domain of the CD22 antigen-binding arm comprises mutations H435R and/or Y436F.

In various embodiments, the scFv used in multispecific antibodies described herein comprises, from the N- to C-terminus, a VH, a linker and a VL (VH-L-VL) or the VL, the L and the VH (VL-L-VH). In some embodiments, the scFv comprises, from the N- to C-terminus, the VL, the linker and the VH (VL-L-VH). In some embodiments, the scFv comprises, from the N- to C-terminus, the VH, the linker and the VH (VL-L-VH).

Linkers used in the present disclosure may be about 5-50 amino acids long. In some embodiments, the linker is about 10-40 amino acids long. In some embodiments, the linker is about 10-35 amino acids long. In some embodiments, the linker is about 10-30 amino acids long. In some embodiments, the linker is about 10-25 amino acids long. In some embodiments, the linker is about 10-20 amino acids long. In some embodiments, the linker is about 15-20 amino acids long. In some embodiments, the linker is 6 amino acids long. In some embodiments, the linker is 7 amino acids long. In some embodiments, the linker is 8 amino acids long. In some embodiments, the linker is 9 amino acids long. In some embodiments, the linker is 10 amino acids long. In some embodiments, the linker is 11 amino acids long. In some embodiments, the linker is 12 amino acids long. In some embodiments, the linker is 13 amino acids long. In some embodiments, the linker is 14 amino acids long. In some embodiments, the linker is 15 amino acids long. In some embodiments, the linker is 16 amino acids long. In some embodiments, the linker is 17 amino acids long. In some embodiments, the linker is 18 amino acids long. In some embodiments, the linker is 19 amino acids long. In some embodiments, the linker is 20 amino acids long. In some embodiments, the linker is 21 amino acids long. In some embodiments, the linker is 22 amino acids long. In some embodiments, the linker is 23 amino acids long. In some embodiments, the linker is 24 amino acids long. In some embodiments, the linker is 25 amino acids long. In some embodiments, the linker is 26 amino acids long. In some embodiments, the linker is 27 amino acids long. In some embodiments, the linker is 28 amino acids long. In some embodiments, the linker is 29 amino acids long. In some embodiments, the linker is 30 amino acids long. In some embodiments, the linker is 31 amino acids long. In some embodiments, the linker is 32 amino acids long. In some embodiments, the linker is 33 amino acids long. In some embodiments, the linker is 34 amino acids long. In some embodiments, the linker is 35 amino acids long. In some embodiments, the linker is 36 amino acids long. In some embodiments, the linker is 37 amino acids long. In some embodiments, the linker is 38 amino acids long. In some embodiments, the linker is 39 amino acids long. In some embodiments, the linker is 40 amino acids long. Exemplary linkers that may be used are Gly rich linkers, Gly and Ser containing linkers, Gly and Ala containing linkers, Ala and Ser containing linkers, and other flexible linkers.

Other linker sequences may include portions of immunoglobulin hinge area, CL or CH1 derived from any immunoglobulin heavy or light chain isotype. Exemplary linkers that may be used are shown in Table 1. Additional linkers are described for example in Int. Pat. Publ. No. WO2019/060695.

In some embodiments, the linker comprises the amino acid sequence of one of SEQ ID NOs:91-125.

TABLE 1

Exemplary linker sequences

| Amino acid sequence | SEQ ID NO |
|---|---|
| GGGSGGSGGCPPCGGSGG | 91 |
| GGSEGKSSGSGSESKSTGGS | 92 |
| GGGSGGGS | 93 |
| GGGSGGGSGGGS | 94 |
| GGGSGGGSGGGSGGGS | 95 |
| GGGSGGGSGGGSGGGSGGGS | 96 |
| GGGGSGGGGSGGGGS | 97 |
| GGGGSGGGGSGGGGSGGGGS | 98 |

TABLE 1-continued

Exemplary linker sequences

| Amino acid sequence | SEQ ID NO |
|---|---|
| GGGGSGGGGSGGGGSGGGGSGGGGS | 99 |
| GSTSGSGKPGSGEGSTKG | 100 |
| IRPRAIGGSKPRVA | 101 |
| GKGGSGKGGSGKGGS | 102 |
| GGKGSGGKGSGGKGS | 103 |
| GGGKSGGGKSGGGKS | 104 |
| GKGKSGKGKSGKGKS | 105 |
| GGGKSGGKGSGKGGS | 106 |
| GKPGSGKPGSGKPGS | 107 |
| GKPGSGKPGSGKPGSGKPGS | 108 |
| GKGKSGKGKSGKGKSGKGKS | 109 |
| STAGDTHLGGEDFD | 110 |
| GEGGSGEGGSGEGGS | 111 |
| GGEGSGGEGSGGEGS | 112 |
| GEGESGEGESGEGES | 113 |
| GGGESGGEGSGEGGS | 114 |
| GEGESGEGESGEGESGEGES | 115 |
| GSTSGSGKPGSGEGSTKG | 116 |
| PRGASKSGSASQTGSAPGS | 117 |
| GTAAAGAGAAGGAAAGAAG | 118 |
| GTSGSSGSGSGGSGSGGG | 119 |
| GKPGSGKPGSGKPGSGKPGS | 120 |
| GSGS | 121 |
| APAPAPAPAP | 122 |
| APAPAPAPAPAPAPAPAP | 123 |
| AEAAAKEAAAKEAAAAKEAAAAKEAAAAKAAA | 124 |
| GGGGSGGGGS | 125 |

Bispecific Antibody

In some embodiments, a bispecific antibody, or a bispecific antibody fragment of the present disclosure comprises a CD79b-binding arm and a CD22-binding arm. In one embodiment, the bispecific antibody or bispecific antibody fragment comprises a first antigen-binding site that binds a first antigen and a second antigen-binding site that binds a second antigen.

In one embodiment, the bispecific antibody or bispecific antibody fragment comprises a first antigen-binding arm that binds CD22 and a second antigen-binding arm that binds CD79b.

In one embodiment, the bispecific antibody or bispecific antibody fragment comprises a first antigen-binding arm that binds CD79b and a second antigen-binding arm that binds CD22. In one embodiment, the first antigen-binding arm that binds CD79b comprises HCDR1 of SEQ ID NO: 9, 17, 25, 33, 41, 49 or 57; an HCDR2 of SEQ ID NO: 10, 18, 26, 34, 42, 50 or 58; an HCDR3 of SEQ ID NO: 11, 19, 27, 35, 43, 51 or 59; an LCDR1 of SEQ ID NO: 12, 20, 28, 36, 44, 52 or 60; LCDR2 of SEQ ID NO: 13, 21, 29, 37, 45, 53 or 61; and an LCDR3 of SEQ ID NO: 14, 22, 30, 38, 46, 54 or 62. In one embodiment, the antigen-binding arm that binds CD79b comprises an HCDR1, an HCDR2, an HCDR3, an LCDR1, LCDR2, and LCDR3 of:

SEQ ID NOs: 9, 10, 11, 12, 13, and 14, respectively;
SEQ ID NOs: 17, 18, 19, 20, 21, and 22, respectively;
SEQ ID NOs: 25, 26, 27, 28, 29, and 30, respectively;
SEQ ID NOs: 33, 34, 35, 36, 37, and 38, respectively;
SEQ ID NOs: 41, 42, 43, 44, 45, and 46, respectively;
SEQ ID NOs: 49, 50, 51, 52, 53, and 54, respectively; or
SEQ ID NOs: 57, 58, 59, 60, 61, and 62, respectively.

In one embodiment, the first antigen-binding arm that binds CD79b comprises a VH of SEQ ID NOs: 15, 23, 31, 39, 47, 55, 63 or 80 and a VL of SEQ ID NOs: 16, 24, 32, 40, 48, 56, 64 or 81. In one embodiment, the first antigen-binding arm that binds CD79b comprises an VH and a VL of:

SEQ ID NOs: 15 and 16, respectively;
SEQ ID NOs: 23 and 24, respectively;
SEQ ID NOs: 31 and 32, respectively;
SEQ ID NOs: 39 and 40, respectively;
SEQ ID NOs: 47 and 48, respectively;
SEQ ID NOs: 55 and 56, respectively;
SEQ ID NOs: 63 and 64, respectively; or
SEQ ID NOs: 80 and 81, respectively.

In one embodiment, the second antigen-binding arm that binds CD22 comprises an HCDR1 of SEQ ID NO: 1, an HCDR2 of SEQ ID NO: 2, and an HCDR3 of SEQ ID NO: 3. In one embodiment, the second antigen-binding arm that binds CD22 comprises a VH of SEQ ID NO: 7. In one embodiment, the second antigen-binding arm that binds CD22 comprises an LCDR1 of SEQ ID NO: 4, an LCDR2 of SEQ ID NO: 5, and an LCDR3 of SEQ ID NO: 6. In one embodiment, the second antigen-binding arm that binds CD22 comprises a VL of SEQ ID NO: 8.

In one embodiment, the bispecific antibody or bispecific antibody fragment comprises an antigen-binding arm that binds CD79b comprising a HCDR1 of SEQ ID NO: 9, an HCDR2 of SEQ ID NO: 10, an HCDR3 of SEQ ID NO: 11, LCDR1 of SEQ ID NO: 12, an LCDR2 of SEQ ID NO: 13, and an LCDR3 of SEQ ID NO: 14, and an antigen-binding arm that binds CD22 comprising an HCDR1 of SEQ ID NO: 1, an HCDR2 of SEQ ID NO: 2, and an HCDR3 of SEQ ID NO: 3; and an LCDR1 of SEQ ID NO: 4, an LCDR2 of SEQ ID NO: 5, and an LCDR3 of SEQ ID NO: 6.

In one embodiment, the bispecific antibody or bispecific antibody fragment comprises an antigen-binding arm that binds CD79b comprising a HCDR1 of SEQ ID NO: 9, an HCDR2 of SEQ ID NO: 10, an HCDR3 of SEQ ID NO: 11, LCDR1 of SEQ ID NO: 12, an LCDR2 of SEQ ID NO: 13, and an LCDR3 of SEQ ID NO: 14, and an antigen-binding arm that binds CD22 comprising a VH of SEQ ID NO:7, and an LCDR1 of SEQ ID NO: 4, an LCDR2 of SEQ ID NO: 5, and an LCDR3 of SEQ ID NO: 6.

In one embodiment, the bispecific antibody or bispecific antibody fragment comprises an antigen-binding arm that binds CD79b comprising a HCDR1 of SEQ ID NO: 9, an HCDR2 of SEQ ID NO: 10, an HCDR3 of SEQ ID NO: 11, LCDR1 of SEQ ID NO: 12, an LCDR2 of SEQ ID NO: 13, and an LCDR3 of SEQ ID NO: 14, and an antigen-binding arm that binds CD22 comprising an HCDR1 of SEQ ID NO: 1, an HCDR2 of SEQ ID NO: 2, and an HCDR3 of SEQ ID NO: 3; and a VL of SEQ ID NO:8.

In one embodiment, the bispecific antibody or bispecific antibody fragment comprises an antigen-binding arm that binds CD79b comprising a HCDR1 of SEQ ID NO: 9, an HCDR2 of SEQ ID NO: 10, an HCDR3 of SEQ ID NO: 11, LCDR1 of SEQ ID NO: 12, an LCDR2 of SEQ ID NO: 13, and an LCDR3 of SEQ ID NO: 14, and an antigen-binding arm that binds CD22 comprising a VH of SEQ ID NO:7 and a VL of SEQ ID NO:8.

In one embodiment, the bispecific antibody or bispecific antibody fragment comprises an antigen-binding arm that binds CD79b comprising a VH of SEQ ID NO:80, an LCDR1 of SEQ ID NO: 12, an LCDR2 of SEQ ID NO: 13, and an LCDR3 of SEQ ID NO: 14, and an antigen-binding arm that binds CD22 comprising an HCDR1 of SEQ ID NO: 1, an HCDR2 of SEQ ID NO: 2, an HCDR3 of SEQ ID NO: 3, an LCDR1 of SEQ ID NO: 4, an LCDR2 of SEQ ID NO: 5, and an LCDR3 of SEQ ID NO: 6.

In one embodiment, the bispecific antibody or bispecific antibody fragment comprises an antigen-binding arm that binds CD79b comprising a HCDR1 of SEQ ID NO: 9, an HCDR2 of SEQ ID NO: 10, an HCDR3 of SEQ ID NO: 11, and a VL of SEQ ID NO:81, and an antigen-binding arm that binds CD22 comprising an HCDR1 of SEQ ID NO: 1, an HCDR2 of SEQ ID NO: 2, an HCDR3 of SEQ ID NO: 3, LCDR1 of SEQ ID NO: 4, an LCDR2 of SEQ ID NO: 5, and an LCDR3 of SEQ ID NO: 6.

In one embodiment, the bispecific antibody or bispecific antibody fragment comprises an antigen-binding arm that binds CD79b comprising a VH of SEQ ID NO:80 and a VL of SEQ ID NO:81, and an antigen-binding arm that binds CD22 comprising an HCDR1 of SEQ ID NO: 1, an HCDR2 of SEQ ID NO: 2, an HCDR3 of SEQ ID NO: 3, an LCDR1 of SEQ ID NO: 4, an LCDR2 of SEQ ID NO: 5, and an LCDR3 of SEQ ID NO: 6.

In one embodiment, the bispecific antibody or bispecific antibody fragment comprises an antigen-binding arm that binds CD79b comprising a VH of SEQ ID NO:80 and a VL of SEQ ID NO:81, and an antigen-binding arm that binds CD22 comprising a VH of SEQ ID NO:7 and a VL of SEQ ID NO:8.

Homologous Antibodies

The antibodies, including monospecific antibodies, multispecific antibodies or antigen-binding fragments described herein, include variants having single or multiple amino acid substitutions, deletions, or additions that retain the biological properties (e.g., binding affinity or immune effector activity) of the described multispecific antibodies or antigen-binding fragments. For example, variants may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29 or more amino acid substitutions in the antigen binding domain that bind CD79b and/or CD22 as long as they retain or have improved functional properties when compared to the parent antigen binding domains. In some embodiments, the sequence identity may be about 80%, 81%, 82%, 83%, 84%, 85%, 86%, 87%, 88%, 89%, 90%, 91%, 92%, 93%, 94%, 95%, 96%, 97%, 98% or 99% to the antigen binding domains that bind CD79b and/or CD22 of the disclosure. In some embodiments, the variation is in the framework regions. In some embodiments, variants are generated by conservative substitutions.

In the context of the present invention the following notations are, unless otherwise indicated, used to describe a mutation; i) substitution of an amino acid in a given position is written as e.g. K409R which means a substitution of a Lysine in position 409 with an Arginine; and ii) for specific variants the specific three or one letter codes are used, including the codes Xaa and X to indicate any amino acid residue. Thus, the substitution of Arginine for Lysine in position 409 is designated as: K409R, or the substitution of any amino acid residue for Lysine in position 409 is designated as K409X. In case of deletion of Lysine in position 409 it is indicated by K409*. The skilled person may produce variants having single or multiple amino acid substitutions, deletions, or additions.

These variants may include: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies or antigen-binding fragments described herein may include variants in which amino acid residues from one species are substituted for the corresponding residue in another species, either at the conserved or nonconserved positions. In other embodiments, amino acid residues at nonconserved positions are substituted with conservative or nonconservative residues. The techniques for obtaining these variants, including genetic (deletions, mutations, etc.), chemical, and enzymatic techniques, are known to persons having ordinary skill in the art.

Methods of Generating Antigen Binding Fragment that Bind CD79b or CD22

Antigen binding domains that bind CD79b or CD22 provided in the disclosure may be generated using various technologies. For example, the hybridoma method of Kohler and Milstein may be used to identify VH/VL pairs that bind CD79b or CD22. In the hybridoma method, a mouse or other host animal, such as a hamster, rat or chicken is immunized with human and/or cyno CD79b or CD22, followed by fusion of spleen cells from immunized animals with myeloma cells using standard methods to form hybridoma cells. Colonies arising from single immortalized hybridoma cells may be screened for production of the antibodies containing the antigen binding domains that bind CD79b or CD22 with desired properties, such as specificity of binding, cross-reactivity or lack thereof, affinity for the antigen, and any desired functionality.

Antigen binding domains that bind CD79b or CD22 generated by immunizing non-human animals may be humanized. Exemplary humanization techniques including selection of human acceptor frameworks include CDR grafting (U.S. Pat. No. 5,225,539), SDR grafting (U.S. Pat. No. 6,818,749), Resurfacing (Padlan, (1991) *Mol Immunol* 28:489-499), Specificity Determining Residues Resurfacing (U.S. Patent Publ. No. 2010/0261620), human framework adaptation (U.S. Pat. No. 8,748,356) or superhumanization (U.S. Pat. No. 7,709,226). In these methods, CDRs or a subset of CDR residues of parental antibodies are transferred onto human frameworks that may be selected based on their overall homology to the parental frameworks, based on similarity in CDR length, or canonical structure identity, or a combination thereof.

Humanized antigen binding domains may be further optimized to improve their selectivity or affinity to a desired antigen by incorporating altered framework support residues to preserve binding affinity (backmutations) by techniques such as those described in Int. Patent Publ. Nos. WO1990/

007861 and WO1992/22653, or by introducing variation at any of the CDRs for example to improve affinity of the antigen binding domain.

Transgenic animals, such as mice, rat or chicken carrying human immunoglobulin (Ig) loci in their genome may be used to generate antigen binding fragments that bind CD79b or CD22, and are described in for example U.S. Pat. No. 6,150,584, Int. Patent Publ. No. WO1999/45962, Int. Patent Publ. Nos. WO2002/066630, WO2002/43478, WO2002/043478 and WO1990/04036. The endogenous immunoglobulin loci in such animal may be disrupted or deleted, and at least one complete or partial human immunoglobulin locus may be inserted into the genome of the animal using homologous or non-homologous recombination, using transchromosomes, or using minigenes. Companies such as Regeneron (www_regeneron_com), Harbour Antibodies (www_harbourantibodies_com), Open Monoclonal Technology, Inc. (OMT) (www_omtinc_net), KyMab (www_kymab_com), Trianni (www.trianni_com) and Ablexis (www_ablexis_com) may be engaged to provide human antibodies directed against a selected antigen using technologies as described above.

Antigen binding domains that bind CD79b or CD22 may be selected from a phage display library, where the phage is engineered to express human immunoglobulins or portions thereof such as Fabs, single chain antibodies (scFv), or unpaired or paired antibody variable regions. The antigen binding domains that bind CD79b or CD22 may be isolated for example from phage display library expressing antibody heavy and light chain variable regions as fusion proteins with bacteriophage pIX coat protein as described in Shi et al., (2010) *J Mol Biol* 397:385-96, and Int. Patent Publ. No. WO09/085462). The libraries may be screened for phage binding to human and/or cyno CD79b or CD22 and the obtained positive clones may be further characterized, the Fabs isolated from the clone lysates, and converted to scFvs or other configurations of antigen binding fragments.

Preparation of immunogenic antigens and expression and production of antigen binding domains of the disclosure may be performed using any suitable technique, such as recombinant protein production. The immunogenic antigens may be administered to an animal in the form of purified protein, or protein mixtures including whole cells or cell or tissue extracts, or the antigen may be formed de novo in the animal's body from nucleic acids encoding said antigen or a portion thereof Isotypes, Allotypes and Fc Engineering The antibodies, including monospecific antibodies, multispecific antibodies or antigen-binding fragments described herein may embody several antibody isotypes, such as IgM, IgD, IgG, IgA and IgE. In some embodiments the antibody isotype is IgG1, IgG2, IgG3, or IgG4 isotype, preferably IgG1 or IgG4 isotype. Antibody or antigen-binding fragment thereof specificity is largely determined by the amino acid sequence, and arrangement, of the CDRs. Therefore, the CDRs of one isotype may be transferred to another isotype without altering antigen specificity. Alternatively, techniques have been established to cause hybridomas to switch from producing one antibody isotype to another (isotype switching) without altering antigen specificity. Accordingly, such antibody isotypes are within the scope of the described antibodies or antigen-binding fragments.

The Ig constant region or the fragment of the Ig constant region, such as the Fc region present in the proteins of the disclosure may be of any allotype or isotype.

In some embodiments, the Ig constant region or the fragment of the Ig constant region is an IgG1 isotype. In some embodiments, the Ig constant region or the fragment of the Ig constant region is an IgG2 isotype. In some embodiments, the Ig constant region or the fragment of the Ig constant region is an IgG3 isotype. In some embodiments, the Ig constant region or the fragment of the Ig constant region is an IgG4 isotype.

The Ig constant region or the fragment of the Ig constant region may be of any allotype. It is expected that allotype has no influence on properties of the Ig constant region, such as binding or Fc-mediated effector functions. Immunogenicity of therapeutic proteins comprising Ig constant regions of fragments thereof is associated with increased risk of infusion reactions and decreased duration of therapeutic response (Baert et al., (2003) *N Engl. J. Med.* 348:602-08). The extent to which therapeutic proteins comprising Ig constant regions of fragments thereof induce an immune response in the host may be determined in part by the allotype of the Ig constant region (Stickler et al., (2011) *Genes and Immunity* 12:213-21). Ig constant region allotype is related to amino acid sequence variations at specific locations in the constant region sequences of the antibody. Table 2 shows select IgG1, IgG2 and IgG4 allotypes.

TABLE 2

| | Amino acid residue at position of diversity (residue numbering: EU Index) | | | | | | |
|---|---|---|---|---|---|---|---|
| | IgG2 | | IgG4 | | IgG1 | | |
| Allotype | 189 | 282 | 309 | 422 | 214 | 356 | 358 | 431 |
| G2m(n) | T | M | | | | | | |
| G2m(n-) | P | V | | | | | | |
| G2m(n)/(n-) | T | V | | | | | | |
| nG4m(a) | | | L | R | | | | |
| G1m(17) | | | | | K | E | M | A |
| G1m(17, 1) | | | | | K | D | L | A |

C-terminal lysine (CTL) may be removed from the Ig constant region by endogenous circulating carboxypeptidases in the blood stream (Cai et al., (2011) *Biotechnol. Bioeng.* 108:404-412). During manufacturing, CTL removal may be controlled to less than the maximum level by control of concentration of extracellular $Zn^{2+}$, EDTA or EDTA—$Fe^{3+}$ as described in U.S. Patent Publ. No. US20140273092. CTL content of proteins may be measured using known methods.

In some embodiments, the antibody has a C-terminal lysine content from about 10% to about 90%. In some embodiments, the C-terminal lysine content is from about 20% to about 80%. In some embodiments, the C-terminal lysine content is from about 40% to about 70%. In some embodiments, the C-terminal lysine content is from about 55% to about 70%. In some embodiments, the C-terminal lysine content is about 60%.

Fc region mutations may be made to the multispecific antibody comprising the Ig constant region or to the fragment of the Ig constant region to modulate their effector functions such as ADCC, ADCP and/or ADCP and/or pharmacokinetic properties. This may be achieved by introducing mutation(s) into the Fc that modulate binding of the mutated Fc to activating FcγRs (FcγRI, FcγRIIa, FcγRIII), inhibitory FcγRIIb and/or to FcRn.

In some embodiments, the multispecific antibody comprising the Ig constant region or the fragment of the Ig constant region comprises at least one mutation in the Ig constant region or in the fragment of the Ig constant region.

In some embodiments, the at least one mutation is in the Fc region.

In some embodiments, the multispecific antibody comprising the Ig constant region or to the fragment of the Ig constant region comprises at least one, two, three, four, five, six, seven, eight, nine, ten, eleven, twelve, thirteen, fourteen or fifteen mutations in the Fc region.

In some embodiments, the multispecific antibody comprising the Ig constant region or to the fragment of the Ig constant region comprises at least one mutation in the Fc region that modulates binding of the antibody to FcRn.

Fc positions that may be mutated to modulate half-life (e.g. binding to FcRn) include positions 250, 252, 253, 254, 256, 257, 307, 376, 380, 428, 434 and 435. Exemplary mutations that may be made singularly or in combination are mutations T250Q, M252Y, I253A, S254T, T256E, P257I, T307A, D376V, E380A, M428L, H433K, N434S, N434A, N434H, N434F, H435A and H435R. Exemplary singular or combination mutations that may be made to increase the half-life are mutations M428L/N434S, M252Y/S254T/T256E, T250Q/M428L, N434A and T307A/E380A/N434A. Exemplary singular or combination mutations that may be made to reduce the half-life are mutations H435A, P257I/N434H, D376V/N434H, M252Y/S254T/T256E/H433K/N434F, T308P/N434A and H435R.

In some embodiments, the multispecific antibody comprising the Ig constant region or to the fragment of the Ig constant region comprises M252Y/S254T/T256E mutation.

In some embodiments, the multispecific antibody comprising the Ig constant region or to the fragment of the Ig constant region comprises at least one mutation in the Fc region that reduces binding of the protein to an activating Fcγ receptor (FcγR) and/or reduces Fc effector functions such as C1q binding, complement dependent cytotoxicity (CDC), antibody-dependent cell-mediated cytotoxicity (ADCC) or phagocytosis (ADCP).

Fc positions that may be mutated to reduce binding of the protein to the activating FcγR and subsequently to reduce effector function include positions 214, 233, 234, 235, 236, 237, 238, 265, 267, 268, 270, 295, 297, 309, 327, 328, 329, 330, 331 and 365. Exemplary mutations that may be made singularly or in combination are mutations K214T, E233P, L234V, L234A, deletion of G236, V234A, F234A, L235A, G237A, P238A, P238S, D265A, S267E, H268A, H268Q, Q268A, N297A, A327Q, P329A, D270A, Q295A, V309L, A327S, L328F, A330S and P331S in IgG1, IgG2, IgG3 or IgG4.

Exemplary combination mutations that result in proteins with reduced ADCC are mutations L234A/L235A on IgG1, L234A/L235A/D265S on IgG1, V234A/G237A/P238S/H268A/V309L/A330S/P331S on IgG2, F234A/L235A on IgG4, S228P/F234A/L235A on IgG4, N297A on all Ig isotypes, V234A/G237A on IgG2, K214T/E233P/L234V/L235A/G236-deleted/A327G/P331A/D365E/L358M on IgG1, H268Q/V309L/A330S/P331S on IgG2, S267E/L328F on IgG1, L234F/L235E/D265A on IgG1, L234A/L235A/G237A/P238S/H268A/A330S/P331S on IgG1, S228P/F234A/L235A/G237A/P238S on IgG4, and S228P/F234A/L235A/G236-deleted/G237A/P238S on IgG4. Hybrid IgG2/4 Fc domains may also be used, such as Fc with residues 117-260 from IgG2 and residues 261-447 from IgG4.

An exemplary mutation that results in proteins with reduced CDC is a K322A mutation.

Well-known S228P mutation may be made in IgG4 to enhance IgG4 stability.

In some embodiments, the multispecific antibody comprising the Ig constant region or the fragment of the Ig constant region comprises at least one mutation selected from the group consisting of K214T, E233P, L234V, L234A, deletion of G236, V234A, F234A, L235A, G237A, P238A, P238S, M252Y, S254T, T256E, D265A, S267E, H268A, H268Q, Q268A, N297A, A327Q, P329A, D270A, Q295A, V309L, A327S, L328F, K322, A330S, P331S, T366W, T366S, L368A, Y407V, H318R, and Y319F.

In some embodiments, the Ig constant region, or to the fragment of the Ig constant region, comprises L234A and L235A mutations.

In some embodiments, the Fc domain, or the fragment of the Fc domain, comprises at least one mutation to reduce Fc binding to a Fcγ receptor. In some embodiments, the Fc domain, or the fragment of the Fc domain, comprises mutations corresponding to L234A, L235A, and D265S. In one embodiment, the multispecific antibody comprises the variant IgG set forth in SEQ ID NO:89. In one embodiment, the multispecific antibody comprises SEQ ID NO:79. In one embodiment, the multispecific antibody comprises the Fc domain set forth in SEQ ID NO:90. In one embodiment, the multispecific antibody comprises SEQ ID NO:83.

In some embodiments, the Fc domain, or the fragment of the Fc domain, comprises at least one mutation to extend the half-life of the multispecific binding molecule. In some embodiments, the Fc domain, or the fragment of the Fc domain, comprises mutations corresponding to M252Y, S254T, and T256E. In one embodiment, the multispecific antibody comprises the variant IgG set forth in SEQ ID NO:89. In one embodiment, the multispecific antibody comprises SEQ ID NO:79. In one embodiment, the multispecific antibody comprises the Fc domain set forth in SEQ ID NO:90. In one embodiment, the multispecific antibody comprises SEQ ID NO:83.

In some embodiments, the Fc domain, or the fragment of the Fc domain, comprises at least one mutation to promote heterodimerization. In some embodiments, the Fc domain, or the fragment of the Fc domain, comprises a mutation corresponding to T366W. In one embodiment, the multispecific antibody comprises the variant IgG set forth in SEQ ID NO:89. In one embodiment, the multispecific antibody comprises SEQ ID NO:79. In some embodiments, the Fc domain, or the fragment of the Fc domain, comprises mutations corresponding to T366S, L368A, and Y407V. In one embodiment, the multispecific antibody comprises the Fc domain set forth in SEQ ID NO:90. In one embodiment, the multispecific antibody comprises SEQ ID NO:83.

In some embodiments, the Fc domain, or the fragment of the Fc domain, comprises at least one mutation to reduce Fc binding to protein A. In some embodiments, the Fc domain, or the fragment of the Fc domain, comprises mutations corresponding to H435R and Y436F. In one embodiment, the multispecific antibody comprises the Fc domain set forth in SEQ ID NO:90. In one embodiment, the multispecific antibody comprises SEQ ID NO:83.

In some embodiments, the multispecific antibody comprising the Ig constant region or to the fragment of the Ig constant region comprises at least one mutation in the Fc region that enhances binding of the protein to an Fcγ receptor (FcγR) and/or enhances Fc effector functions such as C1q binding, complement dependent cytotoxicity (CDC), antibody-dependent cell-mediated cytotoxicity (ADCC) and/or phagocytosis (ADCP).

Fc positions that may be mutated to increase binding of the protein to the activating FcγR and/or enhance Fc effector functions include positions 236, 239, 243, 256, 290, 292, 298, 300, 305, 312, 326, 330, 332, 333, 334, 345, 360, 339, 378, 396 or 430 (residue numbering according to the EU index). Exemplary mutations that may be made singularly or in combination are G236A, S239D, F243L, T256A, K290A, R292P, S298A, Y300L, V305L, K326A, A330K, I332E, E333A, K334A, A339T and P396L. Exemplary combination mutations that result in proteins with increased ADCC or ADCP are a S239D/I332E, S298A/E333A/K334A, F243L/R292P/Y300L, F243L/R292P/Y300L/P396L, F243L/R292P/Y300L/V305I/P396L and G236A/S239D/I332E.

Fc positions that may be mutated to enhance CDC include positions 267, 268, 324, 326, 333, 345 and 430. Exemplary mutations that may be made singularly or in combination are S267E, F1268F, S324T, K326A, K326W, E333A, E345K, E345Q, E345R, E345Y, E430S, E430F and E430T. Exemplary combination mutations that result in proteins with increased CDC are K326A/E333A, K326W/E333A, H268F/S324T, S267E/H268F, S267E/S324T and S267E/H268F/S324T.

wild-type IgG1
SEQ ID NO: 85
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVF

SCSVMHEALHNHYTQKSLSLSPGK wild-type IgG2
SEQ ID NO: 86
ASTKGPSVFPLAPCSRSTSESTAALGCLVKDYFPEPVTVSWNSGALTSGVH

TFPAVLQSSGLYSLSSVVTVPSSNFGTQTYTCNVDHKPSNTKVDKTVERKC

CVECPPCPAPPVAGPSVFLFPPKPKDTLMISRTPEVTCVVVDVSHEDPEVQ

FNWYVDGVEVHNAKTKPREEQFNSTFRVVSVLTVVHQDWLNGKEYKCKVSN

KGLPAPIEKTISKTKGQPREPQVYTLPPSREEMTKNQVSLTCLVKGFYPSD

ISVEWESNGQPENNYKTTPPMLDSDGSFFLYSKLTVDKSRWQQGNVFSCSV

MHEALHNHYTQKSLSLSPGK wild-type IgG4
SEQ ID NO: 87
ASTKGPSVFPLAPCSRSTSESTAALGCLVKDYFPEPVTVSWNSGALTSGVH

TFPAVLQSSGLYSLSSVVTVPSSSLGTKTYTCNVDHKPSNTKVDKRVESKY

GPPCPSCPAPEFLGGPSVFLFPPKPKDTLMISRTPEVTCVVVDVSQEDPEV

QFNWYVDGVEVHNAKTKPREEQFNSTYRVVSVLTVLHQDWLNGKEYKCKVS

NKGLPSSIEKTISKAKGQPREPQVYTLPPSQEEMTKNQVSLTCLVKGFYPS

DIAVEWESNGQPENNYKTTPPVLDSDGSFFLYSRLTVDKSRWQEGNVFSCS

VMHEALHNHYTQKSLSLSLGK

IgG derivative
SEQ ID NO: 88
EPKSSDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTCL

VKGFYPSDIAVEWESNGQPENNYKTTPPVLDSDGSFFLYSKLTVDKSRWQQ

GNVFSCSVMHEALHNHYTQKSLSLSPGK

IgG derivative with variants in bold
SEQ ID NO: 89
EPKSSDKTHTCPPCPAPEAAGGPSVFLFPPKPKDTLYITREPEVTCVVVSV

SHEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLWCL

VKGFYPSDIAVEWESNGQPENNYKTTPPVLDSDGSFFLYSKLTVDKSRWQQ

GNVFSCSVMHEALHNHYTQKSLSLSPGK

IgG1 with variants in bold
SEQ ID NO: 90
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPEAAGGPSVFLFPPKPKDTLYITREPEVTCVVVSVSHED

PEVKFNWYVDGVEVHNAKTKPREEQYNSTYRVVSVLTVLHQDWLNGKEYKC

KVSNKALPAPIEKTISKAKGQPREPQVYTLPPSREEMTKNQVSLSCAVKGF

YPSDIAVEWESNGQPENNYKTTPPVLDSDGSFFLVSKLTVDKSRWQQGNVF

SCSVMHEALHNRFTQKSLSLSPGK

Binding of the antibody to FcγR or FcRn may be assessed on cells engineered to express each receptor using flow cytometry. In an exemplary binding assay, 2×10⁵ cells per well are seeded in 96-well plate and blocked in BSA Stain Buffer (BD Biosciences, San Jose, USA) for 30 min at 4° C. Cells are incubated with a test antibody on ice for 1.5 hour at 4° C. After being washed twice with BSA stain buffer, the cells are incubated with R-PE labeled anti-human IgG secondary antibody (Jackson Immunoresearch Laboratories) for 45 min at 4° C. The cells are washed twice in stain buffer and then resuspended in 150 μL of Stain Buffer containing 1:200 diluted DRAQ7 live/dead stain (Cell Signaling Technology, Danvers, USA). PE and DRAQ7 signals of the stained cells are detected by Miltenyi MACSQuant flow cytometer (Miltenyi Biotec, Auburn, USA) using B2 and B4 channel respectively. Live cells are gated on DRAQ7 exclusion and the geometric mean fluorescence signals are determined for at least 10,000 live events collected. FlowJo software (Tree Star) is used for analysis. Data is plotted as the logarithm of antibody concentration versus mean fluorescence signals. Nonlinear regression analysis is performed.

Generation of Multispecific Proteins

The multispecific proteins may be generated using Fab arm exchange, in which substitutions are introduced into two monospecific bivalent antibodies within the Ig constant region CH3 domain which promote Fab arm exchange in vitro. In the methods, two monospecific bivalent antibodies are engineered to have certain substitutions at the CH3 domain that promote heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris(2-carboxyethyl)phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

CH3 mutations that may be used include technologies such as Knob-in-Hole mutations (Genentech), electrostatically-matched mutations (Chugai, Amgen, NovoNordisk, Oncomed), the Strand Exchange Engineered Domain body (SEEDbody) (EMD Serono), Duobody® mutations (Genmab), and other asymmetric mutations (e.g. Zymeworks).

Knob-in-hole mutations are disclosed for example in WO1996/027011 and include mutations on the interface of CH3 region in which an amino acid with a small side chain (hole) is introduced into the first CH3 region and an amino acid with a large side chain (knob) is introduced into the second CH3 region, resulting in preferential interaction between the first CH3 region and the second CH3 region. Exemplary CH3 region mutations forming a knob and a hole are T366Y/F405A, T366W/F405W, F405W/Y407A, T394W/Y407T, T394S/Y407A, T366W/T394S, F405W/T394S and T366W/T366S_L368A_Y407V.

Heavy chain heterodimer formation may be promoted by using electrostatic interactions by substituting positively charged residues on the first CH3 region and negatively charged residues on the second CH3 region as described in US2010/0015133, US2009/0182127, US2010/028637 or US2011/0123532.

Other asymmetric mutations that can be used to promote heavy chain heterodimerization are L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/T350V_T366L_K392L_T394W as described in US2012/0149876 or US2013/0195849 (Zymeworks).

SEEDbody mutations involve substituting select IgG residues with IgA residues to promote heavy chai heterodimerization as described in US20070287170.

Other exemplary mutations that may be used are R409D_K370E/D399K_E357K, S354C_T366W/Y349C_T366S_L368A_Y407V, Y349C_T366W/S354C_T366S_L368A_Y407V, T366K/L351D, L351K/Y349E, L351K/Y349D, L351K/L368E, L351Y_Y407A/T366A_K409F, L351Y_Y407A/T366V_K409F, K392D/D399K, K392D/E356K, K253E_D282K_K322D/D239K_E240K_K292D, K392D_K409D/D356K D399K as described in WO2007/147901, WO 2011/143545, WO2013157954, WO2013096291 and US2018/0118849.

Duobody® mutations (Genmab) are disclosed for example in U.S. Pat. No. 9,150,663 and US2014/0303356 and include mutations F405L/K409R, wild-type/F405L_R409K, T350I_K370T_F405L/K409R, K370W/K409R, D399AFGHILMNRSTVWY/K409R, T366ADEFGHILMQVY/K409R, L368ADEGHNRSTVQ/K409AGRH, D399FHKRQ/K409AGRH, F405IKLSTVW/K409AGRH and Y407LWQ/K409AGRH.

Additional bispecific or multispecific structures include Dual Variable Domain Immunoglobulins (DVD) (Int. Pat. Publ. No. WO2009/134776; DVDs are full length antibodies comprising the heavy chain having a structure VH1-linker-VH2-CH and the light chain having the structure VL1-linker-VL2-CL; linker being optional), structures that include various dimerization domains to connect the two antibody arms with different specificity, such as leucine zipper or collagen dimerization domains (Int. Pat. Publ. No. WO2012/022811, U.S. Pat. Nos. 5,932,448; 6,833,441), two or more domain antibodies (dAbs) conjugated together, diabodies, heavy chain only antibodies such as camelid antibodies and engineered camelid antibodies, Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer), IgG-like Bispecific (InnClone/Eli Lilly), Ts2Ab (MedImmune/AZ) and BsAb (Zymogenetics), HERCULES (Biogen Idec) and TvAb (Roche), ScFv/Fc Fusions (Academic Institution), SCORPION (Emergent BioSolutions/Trubion, Zymogenetics/BMS), Dual Affinity Retargeting Technology (Fc-DART) (MacroGenics) and Dual(ScFv)$_2$-Fab (National Research Center for Antibody Medicine—China), Dual-Action or Bis-Fab (Genentech), Dock-and-Lock (DNL) (ImmunoMedics), Bivalent Bispecific (Biotecnol) and Fab-Fv (UCB-Celltech). ScFv-, diabody-based, and domain antibodies, include but are not limited to, Bispecific T Cell Engager (BiTE) (Micromet), Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies.

In some embodiments, the multispecific proteins comprise three polypeptide chains. In such designs, at least one antigen binding domain is in the form of a scFv. Exemplary designs include (in which "1" indicates the first antigen binding domain, "2" indicates the second antigen binding domain and "3" indicates the third antigen binding domain:

Design 1: Chain A) scFv1-CH2-CH3; Chain B) VL2-CL; Chain C) VH2-CH1-hinge-CH2-CH3

Design 2: Chain A) scFv1-hinge-CH2-CH3; Chain B) VL2-CL; Chain C) VH2-CH1-hinge-CH2-CH3

Design 3: Chain A) scFv1-CH1-hinge-CH2-CH3; Chain B) VL2-CL; Chain C) VH2-CH1-hinge-CH2-CH3

Design 4: Chain A) CH2-CH3-scFv1; Chain B) VL2-CL; Chain C) VH2-CH1-hinge-CH2-CH3

CH3 engineering may be incorporated to the Designs 1-4, such as mutations L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/T350V_T366L_K392L_T394W as described in US2012/0149876 or US2013/0195849 (Zymeworks).

Conjugation to Immunoglobulin (Ig) Constant Regions or Fragments of the Ig Constant Regions In some embodiments, the CD79b binding arm and/or CD22 binding arm of the disclosure are conjugated to an Ig constant region or a fragment of the Ig constant region to impart antibody-like properties, including Fc effector functions C1q binding, complement dependent cytotoxicity (CDC), Fc receptor binding, antibody-dependent cell-mediated cytotoxicity (ADCC), phagocytosis or down regulation of cell surface receptors (e.g., B cell receptor; BCR). The Ig constant region or the fragment of the Ig constant region functions also as a half-life extending moiety as discussed herein. The antigen binding domains that bind CD79b of the disclosure may be engineered into conventional full length antibodies using standard methods. The full length antibodies comprising the antigen binding domain that binds CD79b may further be engineered as described herein.

In some embodiments, an immunoglobulin heavy chain constant region is comprised of subdomains CH1, hinge, CH2 and CH3. In some embodiments, the CH1 domain spans residues A118-V215, the CH2 domain residues A231-K340 and the CH3 domain residues G341-K447 on the heavy chain, residue numbering according to the EU Index. In some instances, G341 is referred as a CH2 domain residue. Hinge is generally defined as including E216 and terminating at P230 of human IgG1. In some embodiments, the Ig Fc region comprises at least the CH2 and the CH3 domains of the Ig constant region, and therefore comprises at least a region from about A231 to K447 of Ig heavy chain constant region.

The invention also provides an antigen binding domain that binds CD79b conjugated to an immunoglobulin (Ig) constant region or a fragment of the Ig constant region.

In some embodiments, the Ig constant region is a heavy chain constant region.

In some embodiments, the Ig constant region is a light chain constant region.

In some embodiments, the fragment of the Ig constant region comprises a Fc region.

In some embodiments, the fragment of the Ig constant region comprises a CH2 domain.

In some embodiments, the fragment of the Ig constant region comprises a CH3 domain.

In some embodiments, the fragment of the Ig constant region comprises the CH2 domain and the CH3 domain.

In some embodiments, the fragment of the Ig constant region comprises at least portion of a hinge, the CH2 domain and the CH3 domain. Portion of the hinge refers to one or more amino acid residues of the Ig hinge.

In some embodiments, the fragment of the Ig constant region comprises the hinge, the CH2 domain and the CH3 domain.

In some embodiments, the antigen binding domain that binds CD79b is conjugated to the N-terminus of the Ig constant region or the fragment of the Ig constant region.

In some embodiments, the antigen binding domain that binds CD79b is conjugated to the C-terminus of the Ig constant region or the fragment of the Ig constant region.

In some embodiments, the CD79b binding arm and/or CD22 binding arm is conjugated to the Ig constant region or the fragment of the Ig constant region via a second linker (L2).

In some embodiments, the L2 comprises the amino acid sequence of SEQ ID NOs: 79-112.

The antigen binding domains that binds CD79b of the disclosure conjugated to Ig constant region or the fragment of the Ig constant region may be assessed for their functionality using several known assays. Binding to CD79b or CD22 may be assessed using methods described herein. Altered properties imparted by the Ig constant domain or the fragment of the Ig constant region such as Fc region may be assayed in Fc receptor binding assays using soluble forms of the receptors, such as the FcγRI, FcγRII, FcγRIII or FcRn receptors, or using cell-based assays measuring for example ADCC, CDC or ADCP.

ADCC may be assessed using an in vitro assay using CD79b or CD22 expressing cells as target cells and NK cells as effector cells. Cytolysis may be detected by the release of label (e.g. radioactive substrates, fluorescent dyes or natural intracellular proteins) from the lysed cells. In an exemplary assay, target cells are used with a ratio of 1 target cell to 4 effector cells. Target cells are pre-labeled with BATDA and combined with effector cells and the test antibody. The samples are incubated for 2 hours and cell lysis measured by measuring released BATDA into the supernatant. Data is normalized to maximal cytotoxicity with 0.67% Triton X-100 (Sigma Aldrich) and minimal control determined by spontaneous release of BATDA from target cells in the absence of any antibody.

ADCP may be evaluated by using monocyte-derived macrophages as effector cells and any CD79b expressing cells as target cells which are engineered to express GFP or other labeled molecule. In an exemplary assay, effector: target cell ratio may be for example 4:1. Effector cells may be incubated with target cells for 4 hours with or without the antibody of the invention. After incubation, cells may be detached using accutase. Macrophages may be identified with anti-CD1 lb and anti-CD14 antibodies coupled to a fluorescent label, and percent phagocytosis may be determined based on % GFP fluorescence in the $CD11^+CD14^+$ macrophages using standard methods.

CDC of cells may be measured for example by plating Daudi cells at $1\times10^5$ cells/well (50 μL/well) in RPMI-B (RPMI supplemented with 1% BSA), adding 50 μL of test protein to the wells at final concentration between 0-100 μg/mL, incubating the reaction for 15 min at room temperature, adding 11 μL of pooled human serum to the wells, and incubation the reaction for 45 min at 37° C. Percentage (%) lysed cells may be detected as % propidium iodide stained cells in FACS assay using standard methods.

Glycoengineering

The ability of the multispecific antibody comprising an Ig constant region or to the fragment of the Ig constant region to mediate ADCC can be enhanced by engineering the Ig constant region or the fragment of the Ig constant region oligosaccharide component. Human IgG1 or IgG3 are N-glycosylated at Asn297 with the majority of the glycans in the well-known biantennary G0, G0F, G1, G1F, G2 or G2F forms. Ig constant region containing proteins may be produced by non-engineered CHO cells typically have a glycan fucose content of about at least 85%. The removal of the core fucose from the biantennary complex-type oligosaccharides attached to the ant multispecific antibody comprising an Ig constant region or to the fragment of the Ig constant region enhances the ADCC of the protein via improved FcγRIIIa binding without altering antigen binding or CDC activity. Such proteins can be achieved using different methods reported to lead to the successful expression of relatively high defucosylated immunoglobulins bearing the biantennary complex-type of Fc oligosaccharides such as control of culture osmolality (Konno et al., *Cytotechnology* 64:249-65, 2012), application of a variant CHO line Lec13 as the host cell line (Shields et al., *J Biol Chem* 277:26733-26740, 2002), application of a variant CHO line EB66 as the host cell line (Olivier et al., *MAbs;* 2(4): 405-415, 2010; PMID:20562582), application of a rat hybridoma cell line YB2/0 as the host cell line (Shinkawa et al., *J Biol Chem* 278:3466-3473, 2003), introduction of small interfering RNA specifically against the a 1,6-fucosyltrasferase (FUT8) gene (Mori et al., *Biotechnol Bioeng* 88:901-908, 2004), or coexpression of β-1,4-N-acetylglucosaminyltransferase III and Golgi α-mannosidase II or a potent alpha-mannosidase I inhibitor, kifunensine (Ferrara et al., *J Biol Chem* 281:5032-5036, 2006, Ferrara et al., *Biotechnol Bioeng* 93:851-861, 2006; Xhou et al., *Biotechnol Bioeng* 99:652-65, 2008).

In some embodiments, the multispecific antibody comprising an Ig constant region or to the fragment of the Ig constant region of the disclosure has a biantennary glycan structure with fucose content of about between 1% to about 15%, for example about 15%, 14%, 13%, 12%, 11% 10%, 9%, 8%, 7%, 6%, 5%, 4%, 3%, 2% or 1%. In some embodiments, multispecific antibody comprising the Ig constant region or to the fragment of the Ig constant region has a glycan structure with fucose content of about 50%, 40%, 45%, 40%, 35%, 30%, 25%, or 20%.

"Fucose content" means the amount of the fucose monosaccharide within the sugar chain at Asn297. The relative amount of fucose is the percentage of fucose-containing structures related to all glycostructures. These may be characterized and quantified by multiple methods, for example: 1) using MALDI-TOF of N-glycosidase F treated sample (e.g. complex, hybrid and oligo- and high-mannose structures) as described in Int Pat. Publ. No. WO2008/077546 2); 2) by enzymatic release of the Asn297 glycans with subsequent derivatization and detection/quantitation by HPLC (UPLC) with fluorescence detection and/or HPLC-MS (UPLC-MS); 3) intact protein analysis of the native or reduced mAb, with or without treatment of the Asn297 glycans with Endo S or other enzyme that cleaves between the first and the second GlcNAc monosaccharides, leaving the fucose attached to the first GlcNAc; 4) digestion of the mAb to constituent peptides by enzymatic digestion (e.g., trypsin or endopeptidase Lys-C), and subsequent separation, detection and quantitation by HPLC-MS (UPLC-MS); 5) Separation of the mAb oligosaccharides from the mAb protein by specific enzymatic deglycosylation with PNGase F at Asn 297. The oligosaccharides thus released can be labeled with a fluorophore, separated and identified by various complementary techniques which allow: fine characterization of the glycan structures by matrix-assisted laser desorption ionization (MALDI) mass spectrometry by comparison of the experimental masses with the theoretical masses, determination of the degree of sialylation by ion exchange HPLC (GlycoSep C), separation and quantification of the oligosaccharide forms according to hydrophilicity criteria by normal-phase HPLC (GlycoSep N), and separation and quantification of the oligosaccharides by high performance capillary electrophoresis-laser induced fluorescence (HPCE-LIF).

"Low fucose" or "low fucose content" as used herein refers to the multispecific antibody comprising the Ig constant region or to the fragment of the Ig constant region with fucose content of about between 1%-15%.

"Normal fucose" or 'normal fucose content" as used herein refers to the multispecific antibody comprising the Ig constant region or to the fragment of the Ig constant region with fucose content of about over 50%, typically about over 80% or over 85%.

Anti-Idiotypic Antibodies

Provided herein are anti-idiotypic that bind to antibodies comprising a CD79b-binding arm and/or CD22-binding arm of the disclosure. An anti-idiotypic (Id) antibody is an antibody which recognizes the antigenic determinants (e.g. the paratope or CDRs) of the antibody. The Id antibody may be antigen-blocking or non-blocking. The antigen-blocking Id may be used to detect the free antigen binding domain in a sample (e.g. the antigen binding domain that binds CD79b of the disclosure). The non-blocking Id may be used to detect the total antibody (free, partially bond to antigen, or fully bound to antigen) in a sample. An Id antibody may be prepared by immunizing an animal with the antibody to which an anti-Id is being prepared.

An anti-Id antibody may also be used as an immunogen to induce an immune response in yet another animal, producing a so-called anti-anti-Id antibody. An anti-anti-Id may be epitopically identical to the original antigen binding domain which induced the anti-Id. Thus, by using antibodies to the idiotypic determinants of the antigen binding domain, it is possible to identify other clones expressing antigen binding domains of identical specificity. Anti-Id antibodies may be varied (thereby producing anti-Id antibody variants) and/or derivatized by any suitable technique, such as those described elsewhere herein.

Immunoconjugates

The antibodies, CD79b-binding arms and/or CD22-binding arms of the disclosure may be conjugated to a heterologous molecule. In some embodiments, the heterologous molecule is a detectable label or a therapeutic agent.

In some embodiments, the disclosure provides a protein comprising an CD79b-binding arm conjugated to a detectable label. In some embodiments, the disclosure provides a protein comprising an CD22-binding arm conjugated to a detectable label. In some embodiments, the disclosure provides a protein comprising an CD79b-binding arm and CD22-binding arm conjugated to a detectable label.

In some embodiments, the disclosure provides a protein comprising an CD79b-binding arm conjugated to a therapeutic agent. In some embodiments, the disclosure provides a protein comprising an CD22-binding arm conjugated to a therapeutic agent. In some embodiments, the disclosure provides a protein comprising an CD79b-binding arm and CD22-binding arm conjugated to a therapeutic agent.

In some embodiments, the detectable label is also a therapeutic agent.

The proteins of the disclosure conjugated to a detectable label may be used to evaluate expression of CD79b and/or CD22 on a variety of samples. Detectable label includes compositions that when conjugated to a protein comprising a CD79b-binding arm and/or CD22-binding arm of the disclosure renders the latter detectable, via spectroscopic, photochemical, biochemical, immunochemical, or chemical means.

Exemplary detectable labels include radioactive isotopes, magnetic beads, metallic beads, colloidal particles, fluorescent dyes, electron-dense reagents, enzymes (for example, as commonly used in an ELISA), biotin, digoxigenin, haptens, luminescent molecules, chemiluminescent molecules, fluorochromes, fluorophores, fluorescent quenching agents, colored molecules, radioactive isotopes, scintillates, avidin, streptavidin, protein A, protein G, antibodies or fragments thereof, polyhistidine, $Ni^{2+}$, Flag tags, myc tags, heavy metals, enzymes, alkaline phosphatase, peroxidase, luciferase, electron donors/acceptors, acridinium esters, and colorimetric substrates.

A detectable label may emit a signal spontaneously, such as when the detectable label is a radioactive isotope. In other cases, the detectable label emits a signal as a result of being stimulated by an external field.

Exemplary radioactive isotopes may be γ-emitting, Auger-emitting, β-emitting, an alpha-emitting or positron-emitting radioactive isotope. Exemplary radioactive isotopes include $^{3}H$, $^{11}C$, $^{13}C$, $^{15}N$, $^{18}F$, $^{19}F$, $^{55}Co$, $^{57}Co$, $^{60}Co$, $^{61}Cu$, $^{62}Cu$, $^{64}Cu$, $^{67}Cu$, $^{68}Ga$, $^{72}As$, $^{75}Br$, $^{86}Y$, $^{89}Zr$, $^{90}Sr$, $^{94m}Tc$, $^{99m}Tc$, $^{115}In$, $^{123}I$, $^{124}I$, $^{125}I$, $^{131}I$, $^{211}At$, $^{212}Bi$, $^{213}Bi$, $^{223}Ra$, $^{226}Ra$, $^{225}Ac$ and $^{227}Ac$.

Exemplary metal atoms are metals with an atomic number greater than 20, such as calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, leand atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, *neptunium* atoms, plutonium atoms, americium atoms, curium atoms, berkelium atoms, californium atoms, einsteinium atoms, fermium atoms, mendelevium atoms, nobelium atoms, or lawrencium atoms.

In some embodiments, the metal atoms may be alkaline earth metals with an atomic number greater than twenty.

In some embodiments, the metal atoms may be lanthanides.

In some embodiments, the metal atoms may be actinides.

In some embodiments, the metal atoms may be transition metals.

In some embodiments, the metal atoms may be poor metals.

In some embodiments, the metal atoms may be gold atoms, bismuth atoms, tantalum atoms, and gadolinium atoms.

In some embodiments, the metal atoms may be metals with an atomic number of 53 (i.e. iodine) to 83 (i.e. bismuth).

In some embodiments, the metal atoms may be atoms suitable for magnetic resonance imaging.

The metal atoms may be metal ions in the form of +1, +2, or +3 oxidation states, such as $Ba^{2+}$, $Bi^{3+}$, $Cs^+$, $Ca^{2+}$, $Cr^{2+}$, $Cr^{3+}$, $Cr^{6+}$, $Co^{2+}$, $Co^{3+}$, $Cu^+$, $Cu^{2+}$, $Cu^{3+}$, $Ga^{3+}$, $Gd^{3+}$, $Au^+$, $Au^{3+}$, $Fe^{2+}$, $Fe^{3+}$, $F^{3+}$, $Pb^{2+}$, $Mn^{2+}$, $Mn^{3+}$, $Mn^{4+}$, $Mn^{7+}$, $Hg^{2+}$, $Ni^{2+}$, $Ni^{3+}$, $Ag^+$, $Sr^{2+}$, $Sn^{2+}$, $Sn^{4+}$, and $Zn^{2+}$. The metal atoms may comprise a metal oxide, such as iron oxide, manganese oxide, or gadolinium oxide.

Suitable dyes include any commercially available dyes such as, for example, 5(6)-carboxyfluorescein, IRDye 680RD maleimide or IRDye 800CW, ruthenium polypyridyl dyes, and the like.

Suitable fluorophores are fluorescein isothiocyanate (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), near infrared (NIR) (700-900 nm) fluorescent dyes, and carbocyanine and aminostyryl dyes.

The protein comprising a CD79b-binding arm and/or CD22-binding arm of the disclosure conjugated to a detectable label may be used as an imaging agent.

In some embodiments, the therapeutic agent is a cytotoxic agent. In some embodiments, the cytotoxic agent is a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

In some embodiments, the cytotoxic agent is daunomycin, doxorubicin, methotrexate, vindesine, bacterial toxins such as diphtheria toxin, ricin, geldanamycin, maytansinoids or calicheamicin. The cytotoxic agent may elicit their cytotoxic and cytostatic effects by mechanisms including tubulin binding, DNA binding, or topoisomerase inhibition.

In some embodiments, the cytotoxic agent is an enzymatically active toxin such as diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In some embodiments, the cytotoxic agent is a radionuclide, such as $^{212}Bi$, $^{131}I$, $^{131}In$, $^{90}Y$, and $^{186}Re$.

In some embodiments, the cytotoxic agent is dolastatins or dolostatin peptidic analogs and derivatives, auristatin or monomethyl auristatin phenylalanine Exemplary molecules are disclosed in U.S. Pat. Nos. 5,635,483 and 5,780,588. Dolastatins and auristatins have been shown to interfere with microtubule dynamics, GTP hydrolysis, and nuclear and cellular division (Woyke et al (2001) Antimicrob Agents and Chemother. 45(12):3580-3584) and have anticancer and antifungal activity. The dolastatin or auristatin drug moiety may be attached to the antibody of the invention through the N (amino) terminus or the C (carboxyl) terminus of the peptidic drug moiety (WO02/088172), or via any cysteine engineered into the antibody.

The protein comprising a CD79b-binding arm and/or CD22-binding arm of the disclosure may be conjugated to a detectable label using known methods.

In some embodiments, the detectable label is complexed with a chelating agent.

In some embodiments, the detectable label is conjugated to the CD79b binding proteins of the disclosure via a linker.

The detectable label or the cytotoxic moiety may be linked directly, or indirectly, to the CD79b binding proteins of the disclosure using known methods. Suitable linkers are known in the art and include, for example, prosthetic groups, non-phenolic linkers (derivatives of N-succimidyl-benzoates; dodecaborate), chelating moieties of both macrocyclics and acyclic chelators, such as derivatives of 1,4,7,10-tetraazacyclododecane-1,4,7,10, tetraacetic acid (DOTA), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tetraacetic acid (TETA), N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene) and other chelating moieties. Suitable peptide linkers are well known.

Polynucleotides, Host Cells and Vectors

In addition to the described antibodies, multispecific antibodies and antigen-binding fragments, also provided are polynucleotide sequences capable of encoding the described antibodies, multispecific antibodies and antigen-binding fragments.

Polynucleotides Encoding a CD22-Binding Arm

In some embodiments, the disclosure provides a polynucleotide encoding comprising a sequence encoding a CD22-binding arm. In some embodiments, polynucleotide encodes a CD22-binding arm comprising a heavy chain complementarity determining region (HCDR) 1, HCDR2 and an HCDR3. In one embodiment, the polynucleotide encodes a CD22-binding arm comprising an HCDR1 of SEQ ID NO: 1. In one embodiment, the polynucleotide encodes a CD22-binding arm comprising an HCDR2 of SEQ ID NO: 2. In one embodiment, the polynucleotide encodes a CD22-binding arm comprising an HCDR3 of SEQ ID NO: 3. In one embodiment, the polynucleotide encodes a CD22-binding arm comprising an HCDR1, HCDR, and HCDR3 of SEQ ID NOs: 1, 2, and 3, respectively.

In some embodiments, the polynucleotide encodes a CD22-binding arm comprising a light chain complementarity determining region (LCDR) 1, LCDR2 and an LCDR3. In one embodiment, the polynucleotide encodes a CD22-binding arm comprising an LCDR1 of SEQ ID NO: 4. In one embodiment, the polynucleotide encodes a CD22-binding arm comprising an LCDR2 of SEQ ID NO: 5. In one embodiment, the polynucleotide encodes a CD22-binding arm comprising an LCDR3 of SEQ ID NO: 6. In one embodiment, the polynucleotide encodes a CD22-binding arm comprising an LCDR1, LCDR2, and LCDR3 of SEQ ID NOs: 4, 5, and 6, respectively.

In some embodiments, the polynucleotide encodes a CD22-binding arm comprising an HCDR1, an HCDR, an HCDR3, a LCDR1, a LCDR, and a LCDR3 of SEQ ID NOs: 1, 2, 3, 4, 5, and 6, respectively.

In some embodiments, the polynucleotide encodes a CD22-binding arm comprising a heavy chain variable domain (VH) of SEQ ID NO:7. In some embodiments, the polynucleotide encodes a CD22-binding arm comprising a light chain variable domain (VL) of SEQ ID NO:8.

In some embodiments, the polynucleotide encodes a CD22-binding arm comprising an HCDR1 of SEQ ID NO:1, an HCDR2 of SEQ ID NO:2, an HCDR3 of SEQ ID NO:3 and a VL of SEQ ID NO:8. In some embodiments, the polynucleotide encodes a CD22-binding arm comprising VH of SEQ ID NO:7, an LCDR1 of SEQ ID NO:4, an LCDR2 of SEQ ID NO:5, and an LCDR3 of SEQ ID NO:6.

In some embodiments, the polynucleotide encodes a CD22-binding arm comprising a VH of SEQ ID NO:7 and a VL of SEQ ID NO:8.

Polynucleotides Encoding a CD79b-Binding Arm

In some embodiments, the disclosure provides a polynucleotide encoding comprising a sequence encoding a CD79b-binding arm In some embodiments, the polynucleotide encodes a CD79b-binding arm comprising an HCDR1, an HCDR2 and an HCDR3. In one embodiment, the polynucleotide encodes a CD79b-binding arm comprising an HCDR1 of SEQ ID NO: 9, 17, 25, 33, 41, 49 or 57. In one embodiment, the polynucleotide encodes a CD79b-binding arm comprising an HCDR2 of SEQ ID NO: 10, 18, 26, 34, 42, 50 or 58. In one embodiment, the polynucleotide encodes a CD79b-binding arm comprising an HCDR3 of SEQ ID NO: 11, 19, 27, 35, 43, 51 or 59.

In one embodiment, the polynucleotide encodes a CD79b-binding arm comprising an HCDR1 of SEQ ID NO: 9, 17, 25, 33, 41, 49 or 57, an HCDR2 of SEQ ID NO: 10, 18, 26, 34, 42, 50 or 58, and HCDR3 of SEQ ID NO: 11, 19, 27, 35, 43, 51 or 59. In one embodiment, the polynucleotide encodes a CD79b-binding arm comprising an HCDR1, HCDR2, and HCDR3 of:
SEQ ID NOs: 9, 10, and 11, respectively;
SEQ ID NOs: 17, 18, and 19, respectively;
SEQ ID NOs: 25, 26, and 27, respectively;
SEQ ID NOs: 33, 34, and 35, respectively;
SEQ ID NOs: 41, 42, and 43, respectively;
SEQ ID NOs: 49, 50, and 51, respectively; or
SEQ ID NOs: 57, 58, and 59, respectively.

In some embodiments, the polynucleotide encodes a CD79b-binding arm comprising an LCDR1, an LCDR2 and an LCDR3. In one embodiment, the polynucleotide encodes a CD79b-binding arm comprising an LCDR1 of SEQ ID NO: 12, 20, 28, 36, 44, 52 or 60. In one embodiment, the polynucleotide encodes a CD79b-binding arm comprising an LCDR2 of SEQ ID NO: 13, 21, 29, 37, 45, 53 or 61. In one embodiment, the polynucleotide encodes a CD79b-binding arm comprising an LCDR3 of SEQ ID NO: 14, 22, 30, 38, 46, 54 or 62. In one embodiment, the polynucleotide encodes a CD79b-binding arm comprising an LCDR1, LCDR2, and LCDR3 of:
SEQ ID NOs: 12, 13, and 14, respectively;
SEQ ID NOs: 20, 21, and 22, respectively;
SEQ ID NOs: 28, 29, and 30, respectively;
SEQ ID NOs: 36, 37, and 38, respectively;
SEQ ID NOs: 44, 45, and 46, respectively;
SEQ ID NOs: 52, 53, and 54, respectively; or
SEQ ID NOs: 60, 61, and 62, respectively.

In some embodiments, the polynucleotide encodes a CD79b-binding arm comprising an HCDR1, an HCDR2, an HCDR3, an LCDR1, an LCDR2 and an LCDR3. In one embodiment, the polynucleotide encodes a CD79b-binding arm comprising s an HCDR1 of SEQ ID NO: 9, 17, 25, 33, 41, 49 or 57. In one embodiment, the polynucleotide encodes a CD79b-binding arm comprising an HCDR2 of SEQ ID NO: 10, 18, 26, 34, 42, 50 or 58. In one embodiment, the polynucleotide encodes a CD79b-binding arm comprising an HCDR3 of SEQ ID NO: 11, 19, 27, 35, 43, 51 or 59. In one embodiment, the polynucleotide encodes a CD79b-binding arm comprising an LCDR1 of SEQ ID NO: 12, 20, 28, 36, 44, 52 or 60. In one embodiment, the polynucleotide encodes a CD79b-binding arm comprising an LCDR2 of SEQ ID NO: 13, 21, 29, 37, 45, 53 or 61. In one embodiment, the polynucleotide encodes a CD79b-binding arm comprising an LCDR3 of SEQ ID NO: 14, 22, 30, 38, 46, 54 or 62. In one embodiment, the polynucleotide encodes a CD79b-binding arm comprising an HCDR1, an HCDR2, an HCDR3, an LCDR1, LCDR2, and LCDR3 of:
SEQ ID NOs: 9, 10, 11, 12, 13, and 14, respectively;
SEQ ID NOs: 17, 18, 19, 20, 21, and 22, respectively;
SEQ ID NOs: 25, 26, 27, 28, 29, and 30, respectively;
SEQ ID NOs: 33, 34, 35, 36, 37, and 38, respectively;
SEQ ID NOs: 41, 42, 43, 44, 45, and 46, respectively;
SEQ ID NOs: 49, 50, 51, 52, 53, and 54, respectively; or
SEQ ID NOs: 57, 58, 59, 60, 61, and 62, respectively.

In one embodiment, the polynucleotide encodes a CD79b-binding arm comprising a VH. In one embodiment, the polynucleotide encodes a CD79b-binding arm comprising a VH of SEQ ID NOs: 15, 23, 31, 39, 47, 55, 63 or 80. In one embodiment, the polynucleotide encodes a CD79b-binding arm comprising a VL. In one embodiment, the polynucleotide encodes a CD79b-binding arm comprising an VL of SEQ ID NOs: 16, 24, 32, 40, 48, 56, 64 or 81.

In one embodiment, the polynucleotide encodes a CD79b-binding arm comprising an HCDR1 of SEQ ID NO: 9, 17, 25, 33, 41, 49 or 57, an HCDR2 of SEQ ID NO: 10, 18, 26, 34, 42, 50 or 58, HCDR3 of SEQ ID NO: 11, 19, 27, 35, 43, 51 or 59 and a VL of SEQ ID NOs: 16, 24, 32, 40, 48, 56, 64 or 81.

In one embodiment, the polynucleotide encodes a CD79b-binding arm comprising a VH of SEQ ID NOs: 15, 23, 31, 39, 47, 55, 63 or 80; an LCDR1 of SEQ ID NO: 12, 20, 28, 36, 44, 52 or 60; an LCDR2 of SEQ ID NO: 13, 21, 29, 37, 45, 53 or 61; and an LCDR3 of SEQ ID NO: 14, 22, 30, 38, 46, 54 or 62.

In one embodiment, the polynucleotide encodes a CD79b-binding arm comprising an VH and a VL. In one embodiment, the polynucleotide encodes a CD79b-binding arm comprising a VH and a VL of:
SEQ ID NOs: 15 and 16, respectively;
SEQ ID NOs: 23 and 24, respectively;
SEQ ID NOs: 31 and 32, respectively;
SEQ ID NOs: 39 and 40, respectively;
SEQ ID NOs: 47 and 48, respectively;
SEQ ID NOs: 55 and 56, respectively;
SEQ ID NOs: 63 and 64, respectively; or
SEQ ID NOs: 80 and 81, respectively.

In one embodiment, the polynucleotide encoding a CD79b-binding arm, or fragment thereof, comprises a sequence encoding a VH comprising a sequence of SEQ ID NOs:65, 68, 70, 73, 75, or 77. In one embodiment, the polynucleotide encoding a CD79b-binding arm, or fragment thereof, comprises a sequence encoding a VL comprising a sequence of SEQ ID NOs:66, 67, 69, 71, 72, 74, 76, or 78. In one embodiment, the polynucleotide encoding a CD79b-binding arm comprises a sequence encoding a VH and a sequence encoding a VL comprising:
SEQ ID NOs: 65 and 66, respectively;
SEQ ID NOs: 65 and 67, respectively;
SEQ ID NOs: 68 and 69, respectively;
SEQ ID NOs: 70 and 71, respectively;
SEQ ID NOs: 70 and 72, respectively;
SEQ ID NOs: 73 and 74, respectively;
SEQ ID NOs: 75 and 76, respectively; or
SEQ ID NOs: 77 and 78, respectively.

Vectors and Host Cells

Vectors comprising the described polynucleotides are also provided, as are cells expressing the antibodies, multispecific antibodies or antigen-binding fragments provided herein. Also described are cells capable of expressing the disclosed vectors. These cells may be mammalian cells (such as 293F cells, CHO cells), insect cells (such as Sf7 cells), yeast cells, plant cells, or bacteria cells (such as *E. coli*). The described antibodies may also be produced by hybridoma cells. The described antibodies may also be recombinantly produced.

Polynucleotides encoding recombinant antigen-binding proteins also are within the scope of the disclosure. In some embodiments, the polynucleotides described (and the peptides they encode) include a leader sequence. Any leader sequence known in the art may be employed. The leader sequence may include, but is not limited to, a restriction site or a translation start site.

Also provided are vectors comprising the polynucleotides described herein. The vectors can be expression vectors. Recombinant expression vectors containing a sequence encoding a polypeptide of interest are thus contemplated as within the scope of this disclosure. The expression vector may contain one or more additional sequences such as but not limited to regulatory sequences (e.g., promoter, enhancer), a selection marker, and a polyadenylation signal. Vectors for transforming a wide variety of host cells are well known and include, but are not limited to, plasmids, phagemids, cosmids, baculoviruses, bacmids, bacterial artificial chromosomes (BACs), yeast artificial chromosomes (YACs), as well as other bacterial, yeast and viral vectors.

Recombinant expression vectors within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

The transcriptional and translational control sequences in expression vectors to be used in transforming vertebrate cells may be provided by viral sources. Exemplary vectors may be constructed as described by Okayama and Berg, 3 *Mol. Cell. Biol.* 280 (1983).

In some embodiments, the multispecific antibody- or antigen-binding fragment-coding sequence is placed under control of a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use with the described embodiments. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. In one embodiment, the multispecific antibody or multispecific binding fragment coding sequence is placed under control of an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like.

Vectors described herein may contain one or more Internal Ribosome Entry Site(s) (IRES). Inclusion of an IRES sequence into fusion vectors may be beneficial for enhancing expression of some proteins. In some embodiments the vector system will include one or more polyadenylation sites (e.g., SV40), which may be upstream or downstream of any of the aforementioned nucleic acid sequences. Vector components may be contiguously linked, or arranged in a manner that provides optimal spacing for expressing the gene products (i.e., by the introduction of "spacer" nucleotides between the ORFs), or positioned in another way. Regulatory elements, such as the IRES motif, may also be arranged to provide optimal spacing for expression.

The vectors may comprise selection markers, which are well known in the art. Selection markers include positive and negative selection markers, for example, antibiotic resistance genes (e.g., neomycin resistance gene, a hygromycin resistance gene, a kanamycin resistance gene, a tetracycline resistance gene, a penicillin resistance gene, a puromycin resistance gene, a blasticidin resistance gene), glutamate synthase genes, HSV-TK, HSV-TK derivatives for ganciclovir selection, or bacterial purine nucleoside phosphorylase gene for 6-methylpurine selection (Gadi et al., 7 *Gene Ther.* 1738-1743 (2000)). A nucleic acid sequence encoding a selection marker or the cloning site may be upstream or downstream of a nucleic acid sequence encoding a polypeptide of interest or cloning site.

The vectors described herein may be used to transform various cells with the genes encoding the described antibodies or antigen-binding fragments. For example, the vectors may be used to generate multispecific antibody or antigen-binding fragment-producing cells. Thus, another aspect features host cells transformed with vectors comprising a nucleic acid sequence encoding an antibody or antigen-binding fragment thereof that binds CD79b, CD20, and/or CD3, such as the antibodies or antigen-binding fragments described and exemplified herein.

Numerous techniques are known in the art for the introduction of foreign genes into cells and may be used to construct the recombinant cells for purposes of carrying out the described methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, 29 Pharmac. Ther. 69-92 (1985)). Calcium phosphate precipitation and polyethylene glycol (PEG)-induced fusion of bacterial protoplasts with mammalian cells may also be used to transform cells.

Cells suitable for use in the expression of the multispecific antibodies or antigen-binding fragments described herein are preferably eukaryotic cells, more preferably cells of plant, rodent, or human origin, for example but not limited to NSO, CHO, CHOK1, perC.6, Tk-ts13, BHK, HEK293 cells, COS-7, T98G, CV-1/EBNA, L cells, C127, 3T3, HeLa, NS1, Sp2/0 myeloma cells, and BHK cell lines, among others. In addition, expression of antibodies may be accomplished using hybridoma cells. Methods for producing hybridomas are well established in the art.

Cells transformed with expression vectors described herein may be selected or screened for recombinant expression of the antibodies or antigen-binding fragments described herein. Recombinant-positive cells are expanded and screened for subclones exhibiting a desired phenotype, such as high level expression, enhanced growth properties, or the ability to yield proteins with desired biochemical characteristics, for example, due to protein modification or altered post-translational modifications. These phenotypes may be due to inherent properties of a given subclone or to mutation. Mutations may be effected through the use of chemicals, UV-wavelength light, radiation, viruses, insertional mutagens, inhibition of DNA mismatch repair, or a combination of such methods.

Pharmaceutical Compositions/Administration

The disclosure also provides a pharmaceutical composition comprising the antibody, multispecific antibody, or binding fragment of the disclosure and a pharmaceutically acceptable carrier.

For therapeutic use, the antibody or multispecific antibody of the disclosure may be prepared as pharmaceutical compositions containing an effective amount of the antibody as an active ingredient in a pharmaceutically acceptable carrier. "Carrier" refers to a diluent, adjuvant, excipient, or vehicle with which the antibody of the invention is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the antibody or multispecific antibodies of the invention in such pharmaceutical formulation may vary, from less than about 0.5%, usually to at least about 1% to as much as 15 or 20% by weight and may be selected primarily based on required dose, fluid volumes, viscosities, etc., according to the mode of administration selected. Suitable vehicles and formulations, inclusive of other human proteins, e.g., human serum albumin, are described, for example, in e.g., Remington: The Science and Practice of Pharmacy, 21st Edition, Troy, D. B. ed., Lipincott Williams and Wilkins, Philadelphia, PA 2006, Part 5, Pharmaceutical Manufacturing pp 691-1092, See especially pp. 958-989.

The mode of administration of the antibody or multispecific antibody of the disclosure may be any suitable route such as parenteral administration, e.g., intradermal, intramuscular, intraperitoneal, intravenous or subcutaneous, transmucosal (oral, intranasal, intravaginal, rectal) or other means appreciated by the skilled artisan, as well known in the art.

The antibody or multispecific antibody of the disclosure of the invention may also be administered prophylactically in order to reduce the risk of developing a disease such as cancer.

Thus, a pharmaceutical composition of the invention for intramuscular injection may be prepared to contain 1 ml sterile buffered water, and between about 1 ng to about 100 mg/kg, e.g. about 50 ng to about 30 mg/kg or more preferably, about 5 mg to about 25 mg/kg, of the CD79b binding protein of the disclosure of the invention.

In embodiments of the present disclosure, the antibody or multispecific antibody-expressing cells may be provided in compositions, e.g., suitable pharmaceutical composition(s) comprising the antibody or multispecific antibody-expressing cells and a pharmaceutically acceptable carrier. In one aspect, the present disclosure provides pharmaceutical compositions comprising an effective amount of a lymphocyte expressing one or more of the antibodies or multispecific antibodies described and a pharmaceutically acceptable excipient. Pharmaceutical compositions of the present disclosure may comprise a antibody or multispecific antibody-expressing cell, e.g., a plurality of antibody or multispecific antibody-expressing cells, as described herein, in combination with one or more pharmaceutically or physiologically acceptable carriers, excipients or diluents. A pharmaceutically acceptable carrier can be an ingredient in a pharmaceutical composition, other than an active ingredient, which is nontoxic to the subject.

A pharmaceutically acceptable carrier can include a buffer, excipient, stabilizer, or preservative. Examples of pharmaceutically acceptable carriers are solvents, dispersion media, coatings, antibacterial and antifungal agents, isotonic and absorption delaying agents, and the like that are physiologically compatible, such as salts, buffers, antioxidants, saccharides, aqueous or non-aqueous carriers, preservatives, wetting agents, surfactants or emulsifying agents, or combinations thereof. The amounts of pharmaceutically acceptable carrier(s) in the pharmaceutical compositions may be determined experimentally based on the activities of the carrier(s) and the desired characteristics of the formulation, such as stability and/or minimal oxidation.

Pharmaceutical compositions may comprise buffers such as acetic acid, citric acid, formic acid, succinic acid, phosphoric acid, carbonic acid, malic acid, aspartic acid, histidine, boric acid, Tris buffers, HEPPSO, HEPES, neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); antibacterial and antifungal agents; and preservatives.

Pharmaceutical compositions of the present disclosure can be formulated for a variety of means of parenteral or non-parenteral administration. In one embodiment, the compositions can be formulated for infusion or intravenous administration. Pharmaceutical compositions disclosed herein can be provided, for example, as sterile liquid preparations, e.g., isotonic aqueous solutions, emulsions, suspensions, dispersions, or viscous compositions, which may be buffered to a desirable pH. Formulations suitable for oral administration can include liquid solutions, capsules, sachets, tablets, lozenges, and troches, powders liquid suspensions in an appropriate liquid and emulsions.

The term "pharmaceutically acceptable," as used herein with regard to pharmaceutical compositions, means approved by a regulatory agency of the Federal or a state government or listed in the U.S. Pharmacopeia or other generally recognized pharmacopeia for use in animals and/or in humans.

As used herein, the term "pharmaceutically acceptable carriers" includes any and all solvents, dispersion media, coatings, antibacterial and antifungal agents, and the like that are physiologically compatible. Examples of suitable carriers, diluents and/or excipients include one or more of water, saline, phosphate buffered saline, dextrose, glycerol, ethanol, and the like, as well as any combination thereof. In many cases, it will be preferable to include isotonic agents, such as sugars, polyalcohols, or sodium chloride in the composition. In particular, relevant examples of suitable carrier include: (1) Dulbecco's phosphate buffered saline, pH of about 7.4, containing or not containing about 1 mg/mL to 25 mg/mL human serum albumin, (2) 0.9% saline (0.9% w/v sodium chloride (NaCl)), and (3) 5% (w/v) dextrose; and may also contain an antioxidant such as tryptamine and a stabilizing agent such as Tween 20®.

The compositions herein may also contain a further therapeutic agent, as necessary for the particular disorder being treated. In one embodiment, the antibody or multispecific antibody or binding fragment and the supplementary active compound will have complementary activities that do not adversely affect each other.

The compositions of the invention may be in a variety of forms. These include for example liquid, semi-solid, and solid dosage forms, but the preferred form depends on the intended mode of administration and therapeutic application. Typical preferred compositions are in the form of injectable or infusible solutions. The preferred mode of administration is parenteral (e.g. intravenous, intramuscular, intraperitoneal, subcutaneous). In a preferred embodiment, the compositions of the invention are administered intravenously as a bolus or by continuous infusion over a period of time. In another preferred embodiment, they are injected by intramuscular, subcutaneous, intra-articular, intrasynovial, intratumoral, peritumoral, intralesional, or perilesional routes, to exert local as well as systemic therapeutic effects.

Sterile compositions for parenteral administration can be prepared by incorporating the antibody, antibody fragment or antibody conjugate of the present invention in the required amount in the appropriate solvent, followed by sterilization by microfiltration. As solvent or vehicle, there may be used water, saline, phosphate buffered saline, dextrose, glycerol, ethanol, and the like, as well as combination thereof. In many cases, it will be preferable to include isotonic agents, such as sugars, polyalcohol's, or sodium chloride in the composition. These compositions may also contain adjuvants, in particular wetting, isotonizing, emulsifying, dispersing and stabilizing agents. Sterile compositions for parenteral administration may also be prepared in the form of sterile solid compositions which may be dissolved at the time of use in sterile water or any other injectable sterile medium.

The antibody, multispecific antibody or antibody fragment may also be orally administered. As solid compositions for oral administration, tablets, pills, powders (gelatin capsules, sachets) or granules may be used. In these compositions, the active ingredient according to the invention is mixed with one or more inert diluents, such as starch, cellulose, sucrose, lactose or silica, under an argon stream. These compositions may also comprise substances other than diluents, for example one or more lubricants such as magnesium stearate or talc, a coloring, a coating (sugar-coated tablet) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavoring or stabilizing products.

The doses depend on the desired effect, the duration of the treatment and the route of administration used; they are generally between 5 mg and 1000 mg per day orally for an adult with unit doses ranging from 1 mg to 250 mg of active substance. In general, the doctor will determine the appropriate dosage depending on the age, weight and any other factors specific to the subject to be treated.

Methods of Detecting

The disclosure also provides a method of detecting CD79b, CD22, or both in a sample, comprising obtaining the sample, contacting the sample with the antibody, multispecific antibody or binding fragment of the disclosure and detecting the bound CD79b, CD22, or both in the sample.

In some embodiments, the sample may be derived from urine, blood, serum, plasma, saliva, ascites, circulating cells, synovial fluid, circulating cells, cells that are not tissue associated (i.e., free cells), tissues (e.g., surgically resected tissue, biopsies, including fine needle aspiration), histological preparations, and the like.

The antibody, multispecific antibody or binding fragment of the disclosure may be detected using known methods. Exemplary methods include direct labeling of the antibodies using fluorescent or chemiluminescent labels, or radiolabels, or attaching to the antibodies of the invention a moiety which is readily detectable, such as biotin, enzymes or epitope tags. Exemplary labels and moieties are ruthenium, $^{111}$In-DOTA, $^{111}$In-diethylenetriaminepentaacetic acid (DTPA), horseradish peroxidase, alkaline phosphatase and beta-galactosidase, poly-histidine (HIS tag), acridine dyes, cyanine dyes, fluorone dyes, oxazin dyes, phenanthridine dyes, rhodamine dyes and Alexafluor® dyes.

The antibody, multispecific antibody or binding fragment of the disclosure may be used in a variety of assays to detect CD79b, CD22, or both in the sample. Exemplary assays are western blot analysis, radioimmunoassay, surface plasmon resonance, immunoprecipitation, equilibrium dialysis, immunodiffusion, electrochemiluminescence (ECL) immunoassay, immunohistochemistry, fluorescence-activated cell sorting (FACS) or ELISA assay.

Methods of Treatment and Use

The antibody, multispecific antibody or binding fragment of the disclosure may be administered to a subject in need thereof to manage, treat, prevent, or ameliorate an autoimmune disease or disorder or one or more symptoms thereof.

The disclosure also provides methods comprising administering a therapeutically effective amount of an antibody, multispecific antibody or binding fragment of the disclosure to a subject having an autoimmune disease.

The disclosure also provides a method comprising administering a therapeutically effective amount of the immunoconjugate comprising an antibody, multispecific antibody or binding fragment of the disclosure to a subject having an autoimmune disease.

The disclosure also provides a method comprising administering a therapeutically effective amount of the pharmaceutical composition comprising an antibody, multispecific antibody or binding fragment of the disclosure to a subject having an autoimmune disease.

The disclosure also provides methods of treating an autoimmune disease in a subject comprising administering a therapeutically effective amount of an antibody, multispecific antibody or binding fragment of the disclosure to the subject in need thereof for a time sufficient to treat the autoimmune disease.

The disclosure also provides a method of treating an autoimmune disease in a subject, comprising administering a therapeutically effective amount of the immunoconjugate comprising an antibody, multispecific antibody or binding fragment of the disclosure to the subject for a time sufficient to treat the autoimmune disease.

The disclosure also provides a method of treating an autoimmune disease in a subject, comprising administering a therapeutically effective amount of the pharmaceutical composition comprising an antibody, multispecific antibody or binding fragment of the disclosure to the subject for a time sufficient to treat the autoimmune disease.

In one embodiment, the autoimmune disease is associated with or characterized by dysregulation of B cells, autoreactive B cells, or the presence of autoantibodies. Examples of autoimmune diseases include, but are not limited to, Systemic lupus erythematosus (SLE), Sjögren's syndrome (SjS), Rheumatoid arthritis, Autoimmune myopathies, Type I diabetes, Addison disease, Pernicious anemia, Autoimmune hepatitis, Primary biliary cholangitis (PBC), Autoimmune pancreatitis, Celiac disease, Focal segmental glomerulosclerosis, Primary membranous nephropathy, Ovarian insufficiency, Autoimmune orchitis, Dry eye disease, Idiopathic interstitial pneumonias, Thyroid disease (eg Grave's), Systemic sclerosis (Scleroderma), Myasthenic syndromes, Autoimmune encephalitis, Bullous skin diseases, TTP, ITP, AIHA, Anca vasculitis, Myocarditis/dilatory CM, NMOSD, Maternal-fetal alloimmunity, Maternal-fetal autoimmunity, Anti-cardiolipin/antiphospholipid syndrome, Hypergammaglobulinemia, Transplant-associated ID, Multifocal motor neuropathy.

The disclosure also provides methods of preventing an autoimmune disease in a subject comprising administering a therapeutically effective amount of an antibody, multispecific antibody or binding fragment of the disclosure to the subject in need thereof for a time sufficient to prevent the autoimmune disease. IN certain embodiments, preventing comprises treating an asymptomatic subject. In certain embodiments, preventing comprises preventing the onset of autoimmune disease symptoms in a subject.

The disclosure also provides methods of preventing an autoimmune disease in a subject comprising administering a therapeutically effective amount of an antibody, multispecific antibody or binding fragment of the disclosure to the subject for a time sufficient to treat the autoimmune disease.

The disclosure also provides a method of preventing an autoimmune disease in a subject, comprising administering a therapeutically effective amount of the immunoconjugate comprising an antibody, multispecific antibody or binding fragment of the disclosure to the subject for a time sufficient to prevent the autoimmune disease.

The disclosure also provides a method of preventing an autoimmune disease in a subject, comprising administering a therapeutically effective amount of the pharmaceutical composition comprising an antibody, multispecific antibody or binding fragment of the disclosure to the subject for a time sufficient to prevent the autoimmune disease.

In one embodiment, the method of preventing an autoimmune disease in a subject further comprises detecting autoantibodies in the subject.

The disclosure also provides methods of modulating B cell activation in a subject comprising administering a therapeutically effective amount of an antibody, multispecific antibody or binding fragment of the disclosure to the subject in need thereof for a time sufficient to modulate B cell activation.

The disclosure also provides methods of modulating B cell activation in a subject comprising administering a therapeutically effective amount of an antibody, multispecific antibody or binding fragment of the disclosure to the subject for a time sufficient to modulate B cell activation.

The disclosure also provides a method of modulating B cell activation in a subject, comprising administering a therapeutically effective amount of an antibody, multispecific antibody or binding fragment of the disclosure to the subject for a time sufficient to modulate B cell activation.

The disclosure also provides a method of modulating B cell activation in a subject, comprising administering a therapeutically effective amount of the immunoconjugate comprising an antibody, multispecific antibody or binding fragment of the disclosure to the subject for a time sufficient to modulate B cell activation.

The disclosure also provides a method of modulating B cell activation in a subject, comprising administering a therapeutically effective amount of the pharmaceutical composition comprising an antibody, multispecific antibody or binding fragment of the disclosure to the subject for a time sufficient to modulate B cell activation.

The disclosure also provides methods of inhibiting aberrant B cell activation in a subject comprising administering a therapeutically effective amount of an antibody, multispecific antibody or binding fragment of the disclosure of the disclosure to the subject in need thereof for a time sufficient to inhibit aberrant B cell activation.

The disclosure also provides methods of inhibiting aberrant B cell activation in a subject comprising administering a therapeutically effective amount of an antibody, multispecific antibody or binding fragment of the disclosure to the subject for a time sufficient to inhibit aberrant B cell activation.

The disclosure also provides a method of inhibiting aberrant B cell activation in a subject, comprising administering a therapeutically effective amount of the immunoconjugate comprising an antibody, multispecific antibody or binding fragment of the disclosure to the subject for a time sufficient to inhibit aberrant B cell activation.

The disclosure also provides a method of inhibiting aberrant B cell activation in a subject, comprising administering a therapeutically effective amount of the pharmaceutical composition comprising an antibody, multispecific antibody or binding fragment of the disclosure to the subject for a time sufficient to inhibit aberrant B cell activation.

The disclosure also provides methods of treating an autoimmune disease in a subject comprising administering a therapeutically effective amount of a composition comprising a multispecific antibody or multispecific binding fragment to the subject in need thereof for a time sufficient to treat the autoimmune disease, wherein the multispecific antibody comprises a CD79b-binding arm and CD22-binding arm.

The disclosure also provides methods of preventing an autoimmune disease in a subject comprising administering a therapeutically effective amount of a composition comprising multispecific antibody or multispecific binding fragment to the subject in need thereof for a time sufficient to prevent the autoimmune disease, wherein the multispecific antibody comprises a CD79b-binding arm and CD22-binding arm.

The disclosure also provides methods of modulating B cell activation in a subject comprising administering a therapeutically effective amount of a composition comprising a multispecific antibody or multispecific binding fragment to the subject in need thereof for a time sufficient to modulate B cell activation, wherein the multispecific antibody comprises a CD79b-binding arm and CD22-binding arm.

The disclosure also provides methods of inhibiting aberrant B cell activation in a subject comprising administering a therapeutically effective amount of a composition comprising a multispecific antibody or multispecific binding fragment to the subject in need thereof for a time sufficient to inhibit aberrant B cell activation, wherein the multispecific antibody comprises a CD79b-binding arm and CD22-binding arm.

The disclosure also provides a method comprising administering a composition comprising a multispecific antibody or multispecific binding fragment to a subject, wherein the multispecific antibody comprises a CD79b-binding arm and CD22-binding arm.

In some embodiments, the CD22-binding arm comprises an HCDR1, an HCDR, an HCDR3, a LCDR1, a LCDR, and a LCDR3 of SEQ ID NOs: 1, 2, 3, 4, 5, and 6, respectively. In some embodiments, the CD22-binding arm comprises a VH of SEQ ID NO:7 and a VL of SEQ ID NO:8.

In some embodiments, the CD79b-binding arm comprises an HCDR1 of SEQ ID NO: 9, 17, 25, 33, 41, 49 or 57; an HCDR2 of SEQ ID NO: 10, 18, 26, 34, 42, 50 or 58; HCDR3 of SEQ ID NO: 11, 19, 27, 35, 43, 51 or 59; an LCDR1 of SEQ ID NO: 12, 20, 28, 36, 44, 52 or 60; an LCDR2 of SEQ ID NO: 13, 21, 29, 37, 45, 53 or 61; and LCDR3 of SEQ ID NO: 14, 22, 30, 38, 46, 54 or 62. In some embodiments, the CD79b-binding arm comprises a VH of SEQ ID NOs: 15, 23, 31, 39, 47, 55, 63 or 80 and a VL of SEQ ID NOs: 16, 24, 32, 40, 48, 56, 64 or 81.

When a therapeutically effective amount is indicated, the precise amount of an antibody, multispecific antibody or binding fragment of the disclosure to be administered can be determined by a physician with consideration of individual differences in age, weight, and condition of the subject.

Delivery systems useful in the context of the antibody, multispecific antibody or binding fragment of the disclosure may include time-released, delayed release, and sustained release delivery systems such that the delivery of the antibody, multispecific antibody or binding fragment of the disclosure occurs prior to, and with sufficient time to cause, sensitization of the site to be treated. The composition can be used in conjunction with other therapeutic agents or therapies. Such systems can avoid repeated administrations of the composition, thereby increasing convenience to the subject and the physician, and may be particularly suitable for certain composition embodiments of the invention.

Many types of release delivery systems are available and known to those of ordinary skill in the art. They include polymer base systems such as poly(lactide-glycolide), copolyoxalates, polyesteramides, polyorthoesters, polycaprolactones, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; sylastic systems; peptide based systems; hydrogel release systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775; 4,667,014; 4,748,034; and 5,239,660 and (b) diffusional systems in which an active component permeates at a controlled rate from a polymer such as described in U.S. Pat. Nos. 3,854,480 and 3,832,253. In addition, pump-based hardware delivery systems can be used, some of which are adapted for implantation.

The administration of the antibody, multispecific antibody or binding fragment of the disclosure may be carried out in any manner, e.g., by parenteral or nonparenteral administration, including by aerosol inhalation, injection, infusions, ingestion, transfusion, implantation or transplantation. For example, the CD79b-binding proteins and compositions described herein may be administered to a patient transarterially, intradermally, subcutaneously, intratumorally, intramedullary, intranodally, intramuscularly, by intravenous (i.v.) injection, or intraperitoneally. In one aspect, the compositions of the present disclosure are administered by i.v. injection. In one aspect, the compositions of the present disclosure are administered to a subject by intradermal or subcutaneous injection. The compositions of antibody, multispecific antibody or binding fragment of the disclosure may be injected, for instance, directly into a tumor, lymph node, tissue, organ, or site of infection.

In one embodiment, administration may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose.

Combination Therapies

The antibody, multispecific antibody or binding fragment of the disclosure may be administered in combination with at least one additional therapeutics.

The antibody, multispecific antibody or binding fragment of the disclosure may also be administered in combination with one or more other therapies. In some embodiments, the antibody, multispecific antibody or binding fragment of the disclosure may be administered in combination with one or more other therapies useful for the prevention, management, treatment or amelioration of an autoimmune disease or disorder or one or more symptoms thereof to a subject in need thereof to prevent, manage, treat or ameliorate an autoimmune disease or disorder or one or more symptoms thereof.

In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In one embodiment, other therapeutic agents such as factors may be administered before, after, or at the same time (simultaneous with) as the antibody, multispecific antibody or binding fragment of the disclosure.

The antibody, multispecific antibody or binding fragment of the disclosure such as CAR-expressing cell described herein and the at least one additional therapeutic agent can be administered simultaneously, in the same or in separate compositions, or sequentially. For sequential administration, the antibody, multispecific antibody or binding fragment described herein can be administered first, and the additional agent can be administered second, or the order of administration can be reversed.

In one embodiment, the subject can be administered an agent which enhances the activity of a antibody, multispecific antibody or binding fragment of the disclosure. For example, in one embodiment, the agent can be an agent which inhibits an inhibitory molecule.

Sequences

Table 3 provides CDR, VH and VL amino acid sequences.

TABLE 3

| Description | | | Amino Acid Sequence | SEQ ID NO: |
|---|---|---|---|---|
| C22B21 | CD22 arm | HCDR1 | GLPLSTSGM | 1 |
| | | HCDR2 | DWDDD | 2 |
| | | HCDR3 | MGYSYGWDAFD | 3 |
| | | LCDR1 | SQSGSRN | 4 |
| | | LCDR2 | GAS | 5 |
| | | LCDR3 | YNNWPL | 6 |
| | | VH | QVTLRESGPALVKPTQTLTLTCTLSGLPLSTS GMAVTWIRQPPGKALEWLALIDWDDDKYY STSLKTRLTISKDTSKNQVVLTMTNMDPVDT ATYYCARMGYSYGWDAFDLWGQGTMVTV SS | 7 |
| | | VL | EVVMTQSPATLSVSPGEGATLSCRASQSGSR NIAWYQQKPGQAPRLLIFGASARATGIPARF TGSGSGTEFTLTISSLQSEDFAVYYCQQYNN WPLTFGGGTKVEIK | 8 |
| CD9B337 | CD79b arm | HCDR1 | GFTLRNY | 9 |
| | | HCDR2 | NQDGSE | 10 |
| | | HCDR3 | DPIESRFD | 11 |
| | | LCDR1 | SQSLVYSDGNTY | 12 |
| | | LCDR2 | KVS | 13 |
| | | LCDR3 | GTHWPP | 14 |
| | | VH | EVQLVESGGGLVQPGGSLRLSCAASGFTLRN YWMSWVRQAPGKGLEWVANINQDGSEKY YVDSVEGRFTISRDNAKKSLWLQMSSLRVE DTAVYYCARDPIESRFDYWGQGTLVTVSS | 15 |
| | | VL | DVVMTQSPLSLPVTLGQPASISCRSSQSLVYS DGNTYLSWFQQRPGQSPRRLIYKVSNRDSG VPDRFSGSGSGTDFTLKISRVEAEDVGVYYC MQGTHWPPTFGGGTKVEIK | 16 |
| CD9B374 | CD79b arm | HCDR1 | GASISSFYWS | 17 |
| | | HCDR2 | RISPSGKTN | 18 |
| | | HCDR3 | GEYSGTYSYSFDV | 19 |
| | | LCDR1 | RSSESLLDSEDGNTYLD | 20 |
| | | LCDR2 | TLSYRAS | 21 |
| | | LCDR3 | MQRMEFPLT | 22 |
| | | VH | QVQLQESGPGLVKPSETLSLTCSVSGASISSF YWSWIRQPADEGLEWIGRISPSGKTNYIPSLK SRIIMSLDASKNQFSLRLNSVTAADTAMYYC ARGEYSGTYSYSFDVWGQGTMVTVSS | 23 |
| | | VL | DIVMTQSPLSLSVTPGEPASISCRSSESLLDSE DGNTYLDWFLQKPGQSPQLLIYTLSYRASGV PDRFSGSGSDTDFTLHISSLEAEDVGLYYCM QRMEFPLTFGQGTKVEIK | 24 |

TABLE 3-continued

| Description | | | Amino Acid Sequence | SEQ ID NO: |
|---|---|---|---|---|
| CD9B330 | CD79b arm | HCDR1 | GDSVSNNSATWN | 25 |
| | | HCDR2 | RTYYRSKWYND | 26 |
| | | HCDR3 | VDIAFDY | 27 |
| | | LCDR1 | SGSSSNIGNHGVN | 28 |
| | | LCDR2 | NDDLLPS | 29 |
| | | LCDR3 | AAWDDSLNGVV | 30 |
| | | VH | QVQLQQSGPGLVKPSQTLSLTCAISGDSVSN NSATWNWIRQSPSRGLEWLGRTYYRSKWY NDYTVSVKSRITINPDTSKNQFSLQLNSVTPE DTAVYYCTRVDIAFDYWGQGTLVTVSS | 31 |
| | | VL | QTVVTQPPSVSEAPRQRVTISCSGSSSNIGNH GVNWYQQLPGKAPKLLIYNDDLLPSGVSDR FSGSTSGTSGSLAISGLQSEDEADYYCAAWD DSLNGVVFGGGTKLTVL | 32 |
| CD9B643 | CD79b arm | HCDR1 | GVSISNYYWS | 33 |
| | | HCDR2 | RISPSGRTN | 34 |
| | | HCDR3 | GEYSGTYSYSFDI | 35 |
| | | LCDR1 | RSSQSLFDSDDGNTYLD | 36 |
| | | LCDR2 | TLSYRAS | 37 |
| | | LCDR3 | MQRMEFPLT | 38 |
| | | VH | QVQLQESGPGLVKPSQTLSLTCTVSGVSISNY YWSWIRQPPGKGLEWIGRISPSGRTNYNPSL KSRVTMSLDASKNQFSLKLSSVTAADTAVY YCARGEYSGTYSYSFDIWGQGTMVTVSS | 39 |
| | | VL | DIQMTQSPSSLSASVGDRVTITCRSSQSLFDS DDGNTYLDWFQQKPGQSPKLLIQTLSYRAS GVPSRFSGSGSGTDFTLTISSLQPEDFATYYC MQRMEFPLTFGGGTKVEIK | 40 |
| CD9B324 | CD79b arm | HCDR1 | GDSVSNNSATWN | 41 |
| | | HCDR2 | RTYYRSKWYND | 42 |
| | | HCDR3 | VDIAFDY | 43 |
| | | LCDR1 | SGSSSNIGNHGVN | 44 |
| | | LCDR2 | NDDLLPS | 45 |
| | | LCDR3 | AAWDDSLNGVV | 46 |
| | | VH | QVQLQQSGPGLVKPSQTLSLTCAISGDSVSN NSATWNWIRQSPSRGLEWLGRTYYRSKWY NDYTVSVKSRITINPDTSKNQFSLQLNSVTPE DTAVYYCTRVDIAFDYWGQGTLVTVSS | 47 |
| | | VL | QLVLTQPPSVSEAPRQRVTISCSGSSSNIGNH GVNWYQQLPGKAPKLLIYNDDLLPSGVSDR FSGSTSGTSGSLAISGLQSEDEADYYCAAWD DSLNGVVFGGGTKLTVL | 48 |
| CD9B389 | CD79b arm | HCDR1 | GVSISNYYWS | 49 |
| | | HCDR2 | RISPSGRTN | 50 |
| | | HCDR3 | GEYSGTYSYSFDI | 51 |
| | | LCDR1 | RSSQSLFDSDDGNTYLD | 52 |
| | | LCDR2 | TLSYRAS | 53 |
| | | LCDR3 | MQRMEFPLT | 54 |
| | | VH | QVQLQQSGPGLVRPSETLALTCSVSGVSISN YYWSWIRQPAGRGLEWIGRISPSGRTNYNTS LKSRGTMSLDASKNQFSLKVNSVTAADTAV YYCARGEYSGTYSYSFDIWGQGTMVTVSS | 55 |
| | | VL | DIVMTQTPLSLPVTPGEPASISCRSSQSLFDSD DGNTYLDWFLQKPGQSPQLLIQTLSYRASGV PDRFSGSGSGTDFTLKISRVEADDVGVYYCM QRMEFPLTFGGGTKLEIK | 56 |
| CD9B390 | CD79b arm | HCDR1 | GGSISNYYWS | 57 |
| | | HCDR2 | RIFYSGKTN | 58 |
| | | HCDR3 | GEYSGEYSYSFDI | 59 |
| | | LCDR1 | RSSQSLLDSDDGNTYVD | 60 |
| | | LCDR2 | TLSYRAS | 61 |
| | | LCDR3 | MQRMEFPLT | 62 |
| | | VH | QVQLQESGPGLVKPSETLSLTCSVSGGSISNY YWSWIRQPAGKGLEWIGRIFYSGKTNYNSSL KSRVTMSADTSKNQFSLKLSSVTAADTAVY YCARGEYSGEYSYSFDIWGQGTTVTVSS | 63 |
| | | VL | EIVMTQSPLSLPVTPGEPASISCRSSQSLLDSD DGNTYVDWFLQKPGQSPQLLIYTLSYRASG VPDRFSGSGSDTDFTLKISRVEAEDVGIYYC MQRMEFPLTFGGGTKVEIK | 64 |

Table 4 provides VH and VL nucleotide sequences.

TABLE 4

| Description | | Nucleotide Sequence | SEQ ID NO |
|---|---|---|---|
| CD9B374 | VH | CAGGTTCAGCTGCAAGAGTCTGGTCCTGGCCTGGTCAAGCCT TCCGAGACACTGTCTCTGACCTGCTCTGTGTCCGGCGCCTCC ATCTCTTCCTTCTACTGGTCCTGGATCCGGCAGCCTGCTGAC GAAGGACTGGAATGGATCGGCCGGATCAGCCCTTCTGGCAA GACCAACTACATCCCCAGCCTGAAGTCCCGGATCATCATGTC CCTGGACGCCTCCAAGAACCAGTTCTCCCTGCGGCTGAACTC TGTGACCGCTGCCGATACCGCCATGTACTACTGTGCCAGAGG CGAGTACTCCGGCACCTACTCCTACAGCTTTGACGTGTGGGG ACAAGGCACCATGGTCACAGTTTCTTCT | 65 |
| | VL | GACATCGTGATGACCCAGTCTCCACTGAGCCTGTCTGTGACA CCTGGCGAGCCTGCCTCCATCTCCTGTAGATCTTCTGAGTCC CTGCTGGACAGCGAGGACGGCAATACCTACCTGGACTGGTT CCTGCAGAAGCCCGGACAGTCTCCTCAGCTGCTGATCTACAC CCTGTCCTACAGAGCCTCTGGCGTGCCCGATAGATTCTCCGG CTCTGGCTCTGACACCGACTTTACCCTGCACATCTCCAGCCT GGAAGCCGAGGATGTGGGCCTGTACTACTGTATGCAGCGGA TGGAATTTCCCCTGACCTTCGGCCAGGGCACCAAGGTGGAA ATCAAG | 66 |
| | VL | GATATTGTGATGACTCAGTCTCCACTCTCCCTGTCCGTCACC CCTGGAGAGCCGGCCTCCATCTCCTGCAGGTCTAGTGAGAG CCTCTTGGATAGTGAAGATGGAAACACCTATTTGGACTGGTT CCTGCAGAAGCCAGGGCAGTCTCCTCAGCTCCTGATCTATAC GCTTTCCTATCGGGCCTCTGGAGTCCCAGACAGGTTCAGTGG CAGTGGGTCGGACACTGATTTCACACTGCACATCAGCAGTC TGGAGGCTGAGGATGTTGGACTTTATTACTGCATGCAACGTAT GGAGTTTCCGCTCACTTTCGGCCAAGGGACCAAGGTGGAAA TCAAA | 67 |
| CD9B330 | VH | CAAGTGCAACTGCAGCAGTCTGGCCCTGGACTGGTCAAGCC TTCTCAGACCCTGTCTCTGACCTGCGCCATCTCCGGCGACTC CGTGTCCAACAACTCCGCTACCTGGAACTGGATCAGACAGT CCCCTTCCAGAGGCCTGGAATGGCTGGGCAGAACCTACTAC CGGTCCAAGTGGTACAACGACTACACCGTGTCCGTGAAGTC CCGGATCACCATCAACCCTGATACCTCTAAGAACCAGTTCTC CCTGCAACTGAACTCTGTGACCCCTGAGGACACCGCCGTGTA CTACTGCACCAGAGTGGACATCGCCTTCGACTACTGGGGCC AGGGCACCCTGGTGACCGTGTCTAGC | 68 |
| | VL | CAGACTGTGGTGACTCAGCCACCCTCGGTGTCTGAAGCCCC AGGCAGAGGGTCACCATCTCCTGTTCTGGAAGTAGCTCCAA CATCGGAAATCATGGTGTAAACTGGTACCAGCAGCTCCCAG GAAAGGCTCCCAAACTCCTCATCTATAATGATGATCTGCTGC CCTCAGGGGTCTCTGACCGATTCTCTGGCTCCACGTCTGGCA CCTCAGGTTCCCTGGCCATCAGTGGGCTCCAGTCTGAGGATG AGGCTGATTATTACTGTGCAGCATGGGATGACAGCCTGAAT GGTGTGGTATTCGGCGGAGGGACTAAACTGACCGTCCTA | 69 |
| CD9B643 | VH | CAGGTTCAGCTGCAAGAGTCTGGCCCTGGCCTGGTCAAGCC CTCTCAGACCCTGTCTCTGACCTGTACCGTGTCCGGCGTGTC CATCTCCAACTACTACTGGTCCTGGATCCGGCAGCCTCCTGG CAAAGGACTGGAATGGATCGGCCGCATCTCTCCTTCTGGTCG CACCAACTACAACCCCAGCCTGAAAAGCAGAGTGACCATGT CTCTGGACGCCTCCAAGAACCAGTTCTCCCTGAAGCTGTCCT CCGTGACCGCTGCTGATACCGCCGTGTACTACTGTGCCAGAG GCGAGTACTCCGGCACCTACTCCTACAGCTTCGACATCTGGG GCCAGGGCACCATGGTCACAGTCTCTTCT | 70 |
| | VL | GACATCCAGATGACCCAGTCTCCATCCTCTCTGTCCGCCTCT GTGGGCGACAGAGTGACCATCACCTGTCGGTCCTCTCAGTCC CTGTTCGACTCTGACGACGGCAACACCTACCTGGACTGGTTC CAGCAGAAGCCCGGCCAGTCTCCTAAGCTGCTGATCCAGAC ACTGTCCTACAGAGCCTCTGGCGTGCCCTCCAGATTTTCCGG CTCTGGCTCTGGCACCGACTTTACCCTGACAATCTCCAGCCT GCAGCCTGAGGACTTCGCCACCTACTACTGTATGCAGCGGAT GGAATTTCCCCTGACCTTCGGCGGAGGCACCAAGGTGGAAA TCAAG | 71 |
| | VL | GACATCCAGATGACCCAGAGCCCTAGCAGCCTGAGCGCCAG CGTGGGCGACAGAGTGACCATTACCTGCAGAAGCAGCCAGA GCCTGTTCGACAGCGACGACGGCAATACCTACCTGGACTGG TTCCAGCAGAAGCCTGGCCAGAGCCCTAAGCTGCTGATCCA GACCCTGAGCTACAGAGCCAGCGGCGTGCCTAGCAGATTCT CCGGCAGCGGCTCCGGCACCGACTTCACCCTGACCATCAGC AGCCTGCAGCCTGAGGACTTCGCCACCTACTACTGCATGCAG AGAATGGAGTTCCCTCTGACCTTCGGCGGCGGCACCAAGGT GGAGATCAAG | 72 |

TABLE 4-continued

| Description | | Nucleotide Sequence | SEQ ID NO |
|---|---|---|---|
| CD9B324 | VH | CAAGTGCAACTGCAGCAGTCTGGCCCTGGACTGGTCAAGCC TTCTCAGACCCTGTCTCTGACCTGCGCCATCTCCGGCGACTC CGTGTCCAACAACTCCGCTACCTGGAACTGGATCAGACAGT CCCCTTCCAGAGGCCTGGAATGGCTGGGCAGAACCTACTAC CGGTCCAAGTGGTACAACGACTACACCGTGTCCGTGAAGTC CCGGATCACCATCAACCCTGATACCTCTAAGAACCAGTTCTC CCTGCAACTGAACTCTGTGACCCCTGAGGACACCGCCGTGTA CTACTGCACCAGAGTGGACATCGCCTTCGACTACGGGGCC AGGGCACCCTGGTGACCGTGTCTAGC | 73 |
| | VL | CAGCTTGTGCTGACTCAGCCACCCTCGGTGTCTGAAGCCCCC AGGCAGAGGGTCACCATCTCCTGTTCTGGAAGTAGCTCCAA CATCGGAAATCATGGTGTAAACTGGTACCAGCAGCTCCCAG GAAAGGCTCCCAAACTCCTCATCTATAATGATGATCTGCTGC CCTCAGGGGTCTCTGACCGATTCTCTGGCTCCACGTCTGGCA CCTCAGGTTCCCTGGCCATCAGTGGGCTCCAGTCTGAGGATG AGGCTGATTATTACTGTGCAGCATGGGATGACAGCCTGAAT GGTGTGGTATTCGGCGGAGGGACTAAACTGACCGTCCTA | 74 |
| CD9B389 | VH | CAAGTTCAGCTTCAACAATCTGGTCCAGGTCTCGTAAGACCA TCAGAAACATTGGCTCTTACATGCTCTGTTAGTGGTGTGTCA ATCAGTAACTATTACTGGTCCTGGATCCGCCAACCTGCTGGC CGTGGGCTCGAATGGATCGGACGAATCTCACCTAGCGGTAG GACAAATTACAACACTTCCCTTAAATCACGAGGGACAATGA GCCTCGACGCATCAAAGAACCAGTTCAGCCTTAAAGTAAAC TCCGTTACCGCAGCAGATACTGCAGTCTACTATTGTGCCAGG GGTGAATATTCAGGAACATATTCCTATTCTTTTGACATTTGG GGCCAGGGAACCATGGTAACAGTGAGTTCA | 75 |
| | VL | GATATTGTGATGACTCAGACTCCACTCTCTCTGCCCGTCACC CCTGGAGAACCGGCCTCCATCTCCTGCAGGTCTAGTCAGAGC CTCTTTGATAGTGATGATGGAAACACCTATTTGGACTGGTTC CTGCAGAAGCCAGGGCAGTCTCCACAGCTCCTAATCCAAAC GCTTTCCTATCGGGCCTCTGGAGTCCCAGACAGGTTCAGTGG CAGTGGGTCAGGCACCGATTTCACACTGAAAATCAGCAGGG TGGAGGCTGATGATGTTGGAGTTTATTACTGCATGCAACGTA TGGAGTTTCCGCTCACTTTCGGCGGAGGGACCAAGCTGGAG ATCAAA | 76 |
| CD9B390 | VH | CAGGTACAACTTCAGGAGAGCGGCCCAGGTTTGGTTAAACC AAGTGAAACCTTGTCACTTACCTGTTCCGTGTCAGGTGGGTC AATAAGCAATTACTACTGGTCCTGGATTAGACAACCTGCTGG AAAGGGGCTTGAATGGATCGGAGGATATTCTACTCAGGGA AGACAAACTACAATAGTAGCCTCAAGTCCAGGGTGACCATG TCCGCTGATACTTCCAAGAATCAATTTAGCCTTAAATTGTCC TCCGTTACAGCCGCTGATACCGCAGTGTACTACTGTCAAGA GGTGAGTACAGTGGCGAATACTCATATTCCTTTGACATCTGG GGTCAGGGCACTACTGTGACTGTTTCATCT | 77 |
| | VL | GAAATAGTGATGACGCAGTCTCCACTCTCCCTGCCCGTCACC CCTGGAGAGCCGGCCTCCATTTCCTGCCGGTCTAGTCAGAGC CTCTTGGATAGTGATGATGGAAACACCTATGTGGACTGGTTC CTGCAGAAGCCAGGGCAGTCTCCACAACTCCTGATCTATAC GCTTTCCTATCGGGCCTCTGGAGTCCCAGACAGGTTCAGTGG CAGTGGGTCAGACACTGATTTCACACTGAAAATCAGCAGGG TGGAGGCTGAAGATGTTGGAATTTATTACTGCATGCAACGTA TGGAGTTTCCGCTCACTTTCGGCGGAGGGACCAAGGTGGAG ATCAAA | 78 |

Table 5 provides sequences of a stapled scFV that binds to CD79b

TABLE 5

| Description | | Amino Acid Sequence | SEQ ID NO |
|---|---|---|---|
| CD79b | Full-length | EVQLVESGGGLVQPGGSLRLSCAASGFTLRNYWMSWVRQAPGCGLEWVA NINQDGSEKYYVDSVEGRFTISRDNAKKSLWLQMSSLRVEDTAVYYCARDPI ESRFDYWGQGTLVTVSSGGGSGGSGGCPPCGGSGGDVVMTQSPLSLPVTL GQPASISCRSSQSLVYSDGNTYLSWFQQRPGQSPRRLIYKVSNRDSGVPDRF SGSGSGTDFTLKISRVEAEDVGVYYCMQGTHWPPTFGCGTKVEIKEPKSSDK THTCPPCPAPEAAGGPSVFLFPPKPKDTLYITREPEVTCVVVSVSHEDPEVKF NWYVDGVEVHNAKTKPREEQYNSTYRVVSVLTVLHQDWLNGKEYKCKVSN KALPAPIEKTISKAKGQPREPQVYTLPPSREEMTKNQVSLWCLVKGFYPSDIA VEWESNGQPENNYKTTPPVLDSDGSFFLYSKLTVDKSRWQQGNVFSCSVM HEALHNHYTQKSLSLSPGK | 79 |

TABLE 5-continued

| Description | | Amino Acid Sequence | SEQ ID NO |
|---|---|---|---|
| VH | | EVQLVESGGGLVQPGGSLRLSCAASGFTLRNYWMSWVRQAPGCGLEWVA NINQDGSEKYYVDSVEGRFTISRDNAKKSLWLQMSSLRVEDTAVYYCARDPI ESRFDYWGQGTLVTVSS | 80 |
| VL | | DVVMTQSPLSLPVTLGQPASISCRSSQSLVYSDGNTYLSWFQQRPGQSPRRL IYKVSNRDSGVPDRFSGSGSGTDFTLKISRVEAEDVGVYYCMQGTHWPPTF GCGTKVEIK | 81 |
| scFv | | EVQLVESGGGLVQPGGSLRLSCAASGFTLRNYWMSWVRQAPGCGLEWVA NINQDGSEKYYVDSVEGRFTISRDNAKKSLWLQMSSLRVEDTAVYYCARDPI ESRFDYWGQGTLVTVSS*GGGSGGSGGCPPCGGSGG*DVVMTQSPLSLPVTL GQPASISCRSSQSLVYSDGNTYLSWFQQRPGQSPRRLIYKVSNRDSGVPDRF SGSGSGTDFTLKISRVEAEDVGVYYCMQGTHWPPTFGCGTKVEIK | 82 |

Table 6 provides sequences of the heavy chain of a Fab that binds to CD22.

TABLE 6

| Description | | Amino Acid Sequence | SEQ ID NO |
|---|---|---|---|
| CD22 | Full-length | QVTLRESGPALVKPTQTLTLTCTLSGLPLSTSGMAVTWIRQPPGKALEWLALI DWDDDKYYSTSLKTRLTISKDTSKNQVVLTMTNMDPVDTATYYCARMGYSY GWDAFDLWGQGTMVTVSSASTKGPSVFPLAPSSKSTSGGTAALGCLVKDYF PEPVTVSWNSGALTSGVHTFPAVLQSSGLYSLSSVVTVPSSSLGTQTYICNVN HKPSNTKVDKKVEPKSCDKTHTCPPCPAPEAAGGPSVFLFPPKPKDTLYITRE PEVTCVVVSVSHEDPEVKFNWYVDGVEVHNAKTKPREEQYNSTYRVVSVLT VLHQDWLNGKEYKCKVSNKALPAPIEKTISKAKGQPREPQVYTLPPSREEMT KNQVSLSCAVKGFYPSDIAVEWESNGQPENNYKTTPPVLDSDGSFFLVSKLT VDKSRWQQGNVFSCSVMHEALHNRFTQKSLSLSPGK | 83 |
| | VH | QVTLRESGPALVKPTQTLTLTCTLSGLPLSTSGMAVTWIRQPPGKALEWLALI DWDDDKYYSTSLKTRLTISKDTSKNQVVLTMTNMDPVDTATYYCARMGYSY GWDAFDLWGQGTMVTVSS | 7 |

Table 7 provides sequences of the light chain of a Fab that binds to CD22

TABLE 7

| Description | | Amino Acid Sequence | SEQ ID NO |
|---|---|---|---|
| CD22 | Full-length | EVVMTQSPATLSVSPGEGATLSCRASQSGSRNIAWYQQKPGQAPRLLIFGAS ARATGIPARFTGSGSGTEFTLTISSLQSEDFAVYYCQQYNNWPLTFGGGTKVEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRGE C | 84 |
| | VL | EVVMTQSPATLSVSPGEGATLSCRASQSGSRNIAWYQQKPGQAPRLLIFGAS ARATGIPARFTGSGSGTEFTLTISSLQSEDFAVYYCQQYNNWPLTFGGGTKVEI K | 8 |

The following examples are provided to further describe some of the embodiments disclosed herein. The examples are intended to illustrate, not to limit, the disclosed embodiments.

EXAMPLES

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

Example 1

PBMC B-Cell Depletion Assay

Peripheral Blood Mononuclear Cells (PBMCs) were purchased through HemaCare (Northridge, CA) as per institutional protocols for human sample acquisition. Cells were thawed in accordance with the manufacture's protocol. PBMCs were cultured with RPMI containing: 10% FBS, 2% Penicillin and Streptomycin, 1% L-glutamine, MEM Non-Essential Amino Acids (NEAA), and sodium pyruvate [ThermoFisher], in a 96 well U-bottom plate at 1×10$^6$ cells per/well. The PBMCs were then incubated with 90 nM of C192B30, control antibodies or anti-human CD20 mAb as a positive control. The cells were then incubated for 48-hrs at 37° C. Following incubation with antibodies, the plate was spun down (300 RCF, 5 min), and cells were resuspended in DPBS. Cells were then stained for viability using LIVE/

DEAD™ Fixable Aqua Dead Cell Stain Kit [Invitrogen cat #L34957] for 5 min at room temperature. The plate was spun down (300 RCF, 5 min), and cells were resuspended in FACs buffer containing Human TruStain FcX™ (Fc Receptor Blocking Solution) [Biolegend cat #422302] and incubated at room temperature for 15 minutes. Following the 15 minutes, cells were stained with anti-CD3 PerCp-Cy5.5 [clone HIT3a Biolegend cat #300328], anti-CD19-PE [clone 4G7 Biolegend cat #392506] anti-CD22-PE [clone HIB22 Biolegend cat #302506] and anti-CD20-PE [clone 2H7 Biolegend cat #302306] at 4° C. for 30 minutes at the manufactures recommended concentration. Plates were spun down (300 RCF, 5 min), washed twice with FACs buffer, fixed with Cytofix buffer [BD Biosciences cat #554655] per manufactures recommendation and resuspend in FACs buffer prior to being acquired for analysis. Flow cytometry data was obtained on a CantoII flow cytometer (BD Biosciences) with up to ten fluorochromes and analyzed using FlowJo software (TreeStar). Analysis looked at the B-cells (CD22, CD19, CD20) vs CD3 population to determine total % B-cell depletion.

Downstream BCR Signaling Cascade Assessment

Purified human B-cells were purchased through HemaCare (Northridge, CA) as per institutional protocols for human sample acquisition. Cells were thawed in accordance with the manufacture's protocol. B-cells were counted and plated in a 96-well U-bottom plate at a concentration of $1.5 \times 10^5$ cells/well. After plating, the B-cells were incubated with C192B30 or control molecules at 4° C. for 30 minutes. Following the 30-minute incubation time, Anti-IgM F(ab'2) (20 µg/mL) [Jackson Immunoresearch laboratories cat #109-006-129] was diluted in warm media and added to the wells containing C192B30, control molecules or media alone (stimulation control). At the same time warm media containing no Anti-IgM was added to wells as a no stimulation control. At the indicated time points (0-30 minutes), B-cells were transferred into a separate U-bottom plate already containing fixation buffer I [BD Bioscience cat #557870]. After the final time-point plates were spun down (300 RCF, 5 min) and washed/resuspended with staining buffer [DPBS+2% HIFCS+1 mM EDTA]. After the cells were washed the plates were again spun down (300 RCF, 5 min) and permeabilized on ice with chilled perm buffer II [BD Bioscience cat #558052] per manufacturers protocol. Following permeabilization plates were spun down (300 RCF, 5 min) and washed twice with staining buffer, blocked with Human TruStain FcX™ (Fc Receptor Blocking Solution) [Biolegend cat #422302] for 15 min then labeled with anti-pSyk (Y352)-PE antibody [BD Bioscience cat #557881] and anti-pPLCg2(Y759)-Alexa 647 [ThermoFisher cat #17-9866-42] for 1 hr on ice. Plates were spun down (300 RCF, 5 min), washed twice with FACs buffer, fixed with Cytofix buffer [BD Biosciences cat #554655] per manufactures recommendation and resuspend in FACs buffer prior to being acquired for analysis. Flow cytometry data was obtained on a CantoII flow cytometer (BD Biosciences) with up to ten fluorochromes and analyzed using FlowJo software (TreeStar). MFI was determined and graphed along with % inhibition as defined by the equation=100*(1−(Stimulated Average−Compound well (Raw data of the compound treated well of interest))/(Stimulated Average−Unstimulated Average)))

B-Cell Proliferation and Cytokine Production

Purified human B-cells were purchased through HemaCare (Northridge, CA) as per institutional protocols for human sample acquisition. Cells were thawed in accordance with the manufacture's protocol. Purified B-cells were cultured with DMEM containing: 10% FBS, 2% Penicillin and Streptomycin, 1% L-glutamine, MEM Non-Essential Amino Acids (NEAA), and sodium pyruvate [ThermoFisher], in a 384-well opaque-walled plate at $3 \times 10^4$ cells per/well. After plating, the B-cells were incubated with C192B30 or control molecules at 4° C. for 30 minutes. Following the 30-minute incubation time, Anti-IgM F(ab'$_2$) (10 µg/mL) [Jackson Immunoresearch laboratories cat #109-006-129] and CPG (0.3125 µM) [Invivogen cat #tlrl-2006-5] were added to the wells containing C192B30, control molecules or media alone (stimulation control). At the same time warm media containing no Anti-IgM or CPG was added to wells as a no stimulation control. After the 72 hrs, 50L of supernatant were transferred into a separate 384-well plate for further analysis and stored at −80° C. The original plate containing the B-cells was analyzed immediately for proliferation by adding in 50L of CellTiterGlo2.0 [Promega cat #G9241] per manufactures protocol to the wells. The samples were then analyzed for luminesce. Briefly, plates were placed on an orbital shaker for 2 minutes, incubated at room temperature for 10 minutes and then recorded for luminescence on a PheraStar [BMGLabTech]. The supernatant that was saved in the previous steps were then also analyzed for IL-6 production via MSD [MesoScale Diagonsitics cat #K151TXK] per manufactures protocol. Percent inhibition was calculated for both proliferation and cytokine production as defined by the equation=100*(1−(Stimulated Average−Compound well (Raw data of the compound treated well of interest))/(Stimulated Average−Unstimulated Average)))

In Vivo Efficacy Model

Janssen Pharmaceutical, LLC Institutional Animal Care and Use Committee approved all experimental procedures involving mice. Female NSG (NOD-scid IL2Rgamma$^{null}$) mice were obtained from Jackson laboratory at 6-12 weeks of age. Mice received full body irradiation 1 day prior to human PBMC transfer. Peripheral Blood Mononuclear Cells (PBMCs) were purchased through HemaCare (Northridge, CA) as per institutional protocols for human sample acquisition. Cells were thawed in accordance with the manufacture's protocol. PBMC concentration was adjusted to $15 \times 10^7$/mL in RPMI-1640 and store on ice briefly prior to injection. Using a 1-cc tuberculin syringe with a 25-G×⅝-in. needle, inject 0.1 ml ($15 \times 10^6$ PBMCs) into the peritoneum via intra-peritoneal (IP) injection. Following injection of human PBMCs, antibodies were given via IP route: isotype (5 mg/kg), C192B30 (at indicated dose) or PBS. Animals were monitored for clinical symptoms and body weight recorded in accordance with IACUC protocol. After 7-days post engraftment, animals were euthanized, and cardiac heart puncture was preformed to collect whole blood. Serum was obtained following centrifugation (17,000 RCF, 1 min). Serum was aliquoted and stored at −80° C. for analysis of human antibody production. Human antibody production was measured via MilliPlex human isotyping magnetic bead panel [Millipore Sigma cat #HGAMMAG-301k] per manufactures protocol. The dilution of mouse serum was used at a 1:100 dilution.

Experimental Results

Experiments were conducted to examine the non-depleting capacity of the CD22×CD79b bispecific antibodies (FIG. 1). PBMCs were cultured for 48-hours with: media alone, a CD22×CD79b bispecific antibody (C192B30, comprising the CDRs of SEQ ID NOs: 1-6 and 9-14), a CD22× Isotype bispecific antibody (C192B36), an Isotype× CD79b bispecific antibody (C192B2) or an anti-CD20 depleting mAb. After 48-hours, the cells were stained for live cells (Zombie Dye Aqua), T-cell (CD3), and B-cells (CD22, CD20, CD19). The percent of b-cells were then calculated in comparison to the media alone wells. As shown in FIG. 1, the bispecific antibodies had little to no depletion of B-cells in any bispecific format while the positive control of anti-CD20 depleting mAb showed a significant decrease of B-cells in PBMCs.

Figure 2:
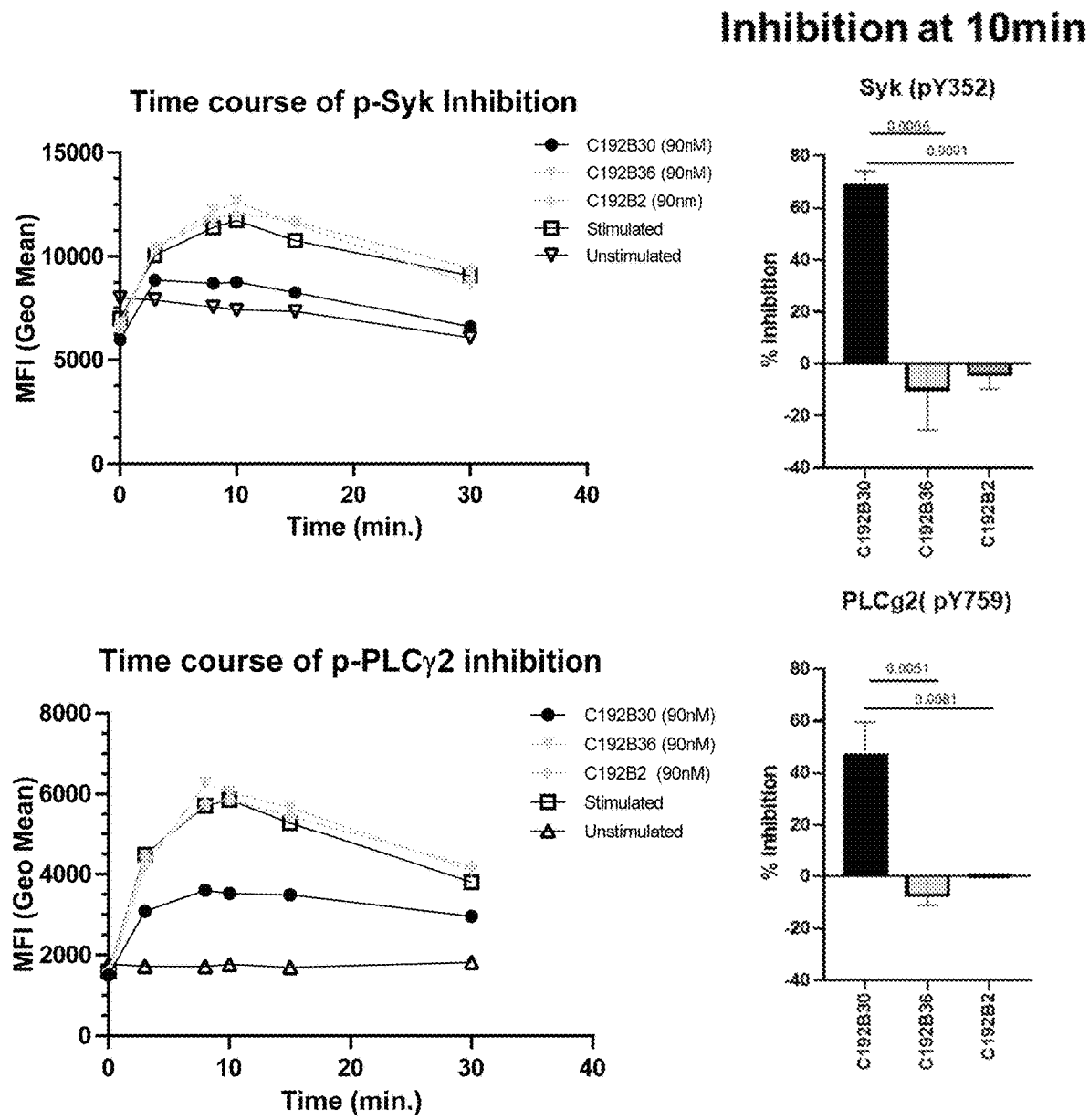
FIG. 2 depicts experimental results demonstrating B-cell proximal signals (p-Syk, p-PLCγ2) were inhibited by a CD22×CD79b bispecific antibody. Purified B-cells were cultured for 30 minutes with the following prior to stimulation: media alone, a CD22×CD79b bispecific antibody (C192B30), a CD22×Isotype bispecific antibody (C192B36), and an Isotype×CD79b bispecific antibody (C192B2). After 30 minutes had passed the B-cells were stimulated with anti-IgM F(ab)'2 (20 μg/mL) to avoid any confounding factors that may have been involved with FcγR binding. The B-cells were then fixed at the given time points (0, 5, 8, 10, 15 and 30) in minutes. Following fixation, the cells were stained for the downstream phospho-protein signaling molecules of the B-cell receptor (BCR) complex (p-Syk, p-PLCγ2). The CD22×CD79b bispecific antibody significantly impacted the ability of B-cells to signal through the BCR complex by inhibiting the p-Syk and p-PLCγ2, compared to the stimulated controls or isotype control arm controls.

Experiments were also conducted to examine B-cell proximal signals (FIG. 2). B-cell proximal signals (p-Syk, p-PLCγ2) were inhibited by a CD22×CD79b bispecific antibody. Purified B-cells were cultured for 30 minutes with the following prior to stimulation: media alone, a CD22× CD79b bispecific antibody (C192B30, comprising the CDRs of SEQ ID NOs: 1-6 and 9-14), a CD22× Isotype bispecific antibody (C192B36), and an Isotype× CD79b bispecific antibody (C192B2). After 30 minutes had passed the B-cells were stimulated with anti-IgM F(ab)'2 (20 µg/mL) to avoid any confounding factors that may have been involved with FcγR binding. The B-cells were then fixed at the given time points (0, 5, 8, 10, 15 and 30) in minutes. Following fixation, the cells were stained for the downstream phospho-protein signaling molecules of the B-cell receptor (BCR) complex (p-Syk, p-PLCγ2). The data in FIG. 2 shows that CD22× CD79b bispecific antibody significantly impacted the ability of B-cells to signal through the BCR complex by inhibiting the p-Syk and p-PLCγ2, compared to the stimulated controls or isotype control arm controls.

Experiments were also conducted to examine B-cell distal read outs of proliferation and cytokine secretion (FIG. 3). The B-cell distal read-outs (proliferation, cytokine secretion) were significantly inhibited by a CD22×CD79b bispecific antibody. Purified B-cells were cultured for 30 minutes with the following prior to stimulation: CD22×CD79b bispecific antibody (C192B30, comprising the CDRs of SEQ ID NOs: 1-6 and 9-14), a CD22×Isotype bispecific antibody (C192B36), and an Isotype× CD79b bispecific antibody (C192B2). After the 30 minutes B-cells were stimulated with a synergistic dose of anti-IgM F(ab)'2 (2.5 µg/mL) and CPG (0.3125 µM). As shown in FIG. 3, the CD22×CD79b antibody was able to significantly reduce B-cell proliferation in response to BCR+TLR stimulation in comparison to the isotype control arms. Further, B-cell IL-6 production was significantly impacted while again the isotype control arms show little to no effect.

Experiments were also conducted to examine IgM antibody production (FIG. 4). The CD22× CD79b bispecific antibody inhibited in vivo IgM antibody production from an NSG-human PBMC transfer model. Human PBMCs were transferred into irradiated immunodeficient mice—NSG (NOD-scid IL2Rgamma$^{null}$). The mice were then treated with varying doses of a CD22×CD79b bispecific antibody (comprising the CDRs of SEQ ID NOs: 1-6 and 9-14; 0.2 mg/kg, 1 mg/kg, and 5 mg/kg) or an isotype control antibody (5 mg/kg). The cells were then allowed to engraft for 7 days. During this time the B-cells began to produce human antibody in vivo. After 7 days the animal were sacrificed and splenocytes for flow cytometry and serum was taken for analysis. The serum showed a significant reduction of human IgM in the 5 mg/kg group treated with the CD22× CD79b bispecific antibody in comparison to controls (PBS and Isotype).

Example 2

A stapled CD22×CD79b scFv binding molecule was developed. As shown in the sequences provided in Tables 5-7, the bispecific antibody features mutations of L234A, L235A, and D265S (AAS) in both Fc domains to reduce interaction with Fc receptors, as well as mutations of M252Y, S254T, T256E (YTE) in both Fc domain to extend the half-life of the molecule. Heterodimerization of the bispecific antibody was enhanced by using the knobs-into-holes platform mutations. Specifically, the CD79b-binding arm comprises an scFv fused onto the N-terminus of the "knob" (T366W) Fc domain and the CD22-binding arm comprise a Fab fused onto the N-terminus of the "holes" (T366S, L368A, and Y407V) Fc domain. Furthermore, the CD22-binding arm comprise "RF" mutations (H435R and Y436F) to disrupt Protein A binding.

Compared with the bispecific molecule used in Example 1, stapling of the CD79b-binding arm (FIG. 5) was achieved by inducing amino acid changes in the VH, VL, and linker regions, as shown in the stapled scFv having the amino acid sequence of SEQ ID NO:82. The stapled bispecific molecule (spFv) comprises the amino acid sequences of SEQ ID NO:79, SEQ ID NO: 83, and SEQ ID NO: 84.

The experimental methods and results are described below.

Aggregation Experiment

High concentration of the molecules was accomplished using Amicon centrifugal ultrafiltration devices with 30 kDa MWCO membranes. An aliquot of each protein was initially diluted to the same starting concentration and centrifuged at 4000×g in 10-minute intervals. At the end of each 10-minute centrifugation step, the concentrators were removed from the centrifuge and a visual estimate of the remaining sample volume was recorded. The concentration step was repeated for all samples until one of the following outcomes was achieved: (1) a sample reached the target volume based on target concentration (e.g., 200 µL for 30 mg initial protein), and (2) a sample precipitated out of solution.

At the end of the centrifugation process, the concentrated samples were recovered, and the protein content was determined using slope spectroscopy. Aliquots of the maximally concentrated protein were then diluted to predefined intermediate concentrations (e.g., 50 and 100 mg/mL). Samples were then stored at their various concentrations state for 2 weeks at 4° C., 25° C. and 40° C. Aggregation was determined by analytical SEC, with each of the samples defined by concentration and storage temperature were diluted to 1 mg/mL immediately prior to analysis.

As illustrated in FIG. 5, introduction of the staple almost completely abrogated the formation of high molecular weight aggregates at all temperatures and concentrations.

B-Cell Proliferation and Cytokine Production

Purified human B-cells were purchased through HemaCare (Northridge, CA) as per institutional protocols for human sample acquisition. Cells were thawed in accordance with the manufacture's protocol. Purified B-cells were cultured with DMEM containing: 10% FBS, 2% Penicillin and Streptomycin, 1% L-glutamine, MEM Non-Essential Amino Acids (NEAA), sodium pyruvate [ThermoFisher] and 0.05 mM Beta-mercaptoethanol, in a 384-well opaque-walled plate at 3×10$^4$ cells per/well. After plating, the B-cells were incubated with WT (unstapled control molecule having (1) L234A, L235A, and D265S (AAS) in both Fc domains; (2) knob (T366W) in CD79b Fc domain and holes (T366S, L368A, and Y407V) in CD22 Fc domain; and (3) H435R and Y436F (RF) in CD22 Fc domain), YTE (same as WT but additionally with M252Y, S254T, and T256E (YTE) in both Fc domains), and stapled YTE (same CDRs and Fc mutations as YTE, but with stapled scFv) molecules at 4° C. for 30 minutes. Following the 30-minute incubation time, anti-IgM F(ab'2) (10 µg/mL) [Jackson Immunoresearch laboratories cat #109-006-129] or anti-IgM F(ab'2) (2.5 µg/mL) and CPG (0.3125 µM) [Invivogen cat #tlrl-2006-5] were added to the wells, or media alone (stimulation control). At the same time warm media containing no anti-IgM or CPG was added to wells as a no stimulation control. After the 72 hrs, 50 µL of supernatant were transferred into a separate 384-well plate for further analysis and stored at −80° C. The original plate containing the B-cells was analyzed immediately for proliferation by adding in 50 µL of CellTiterGlo2.0 [Promega cat #G9241] per manufactures protocol to the wells. The samples were then analyzed for luminesce. Briefly, plates were placed on an orbital shaker for 2 minutes, incubated at room temperature for 10 minutes and then recorded for luminescence on a PheraStar [BMGLabTech]. The supernatant that was saved in the previous steps were then also analyzed for IL-6 production via MSD [MesoScale Diagonsitics cat #K15067L] per manufactures protocol. Percent inhibition was calculated for both proliferation and cytokine production as defined by the equation=100*(1−(Stimulated Average−Compound well (Raw data of the compound treated well of interest))/(Stimulated Average−Unstimulated Average)))

B Cell Activation Marker Expression

PBMC were purchased through HemaCare (Northridge, CA) as per institutional protocols for human sample acquisition. Cells were thawed in accordance with the manufacturer's protocol. PBMC were cultured with RPMI containing: 10% FBS, 2% Penicillin and Streptomycin, [ThermoFisher], in a 96 well plate at 3×105 cells per/well. After plating, the PBMC were incubated with the molecules at 4° C. for 30 minutes. Following the 30-minute incubation time, anti-IgM F(ab'2) (10 µg/mL) [Jackson Immunoresearch laboratories cat #109-006-129] was added to the wells. In control wells, media containing no anti-IgM was added to wells as a no stimulation control. After the 24 hrs, cells were washed with PBS and incubated with Fixable Viability Dye eFluo 506 (Ebioscience) for 30 minutes on ice. Cells were then washed with FACs Buffer (PBS with 1% FBS and 1 mM EDTA) followed by surface staining with anti-CD20-PE [clone 2H7 Biolegend, cat #302348], anti-CD69 AF700 [clone FN50 Biolegend, cat #310922], and anti-CD83 APC/Cy7 [clone HB15 Biolegend, cat #305330] at 4° C. for 30 minutes per the manufacturer's recommended concentration. Plates were spun down (300 RCF, 5 min), washed twice with FACs buffer, then fixed with Cytofix buffer [BD Biosciences cat #554655] per manufacturer's recommendation. The cells were then resuspended in FACs buffer prior to being acquired for analysis. Flow cytometry data was obtained on a Cantoll flow cytometer (BD Biosciences) and analyzed using FlowJo software (TreeStar). The cells were gated on live cells, lymphocytes and on CD20 positive B cells. The percentages of B cells expressing activation markers CD69 or CD83 were determined. Percent inhibition as defined by the equation=100*(1-((Stimulated Average-Drug treated well (Raw data of the drug treated well of interest))/(Stimulated Average−Unstimulated Average).

Experimental Results

Figure 6:
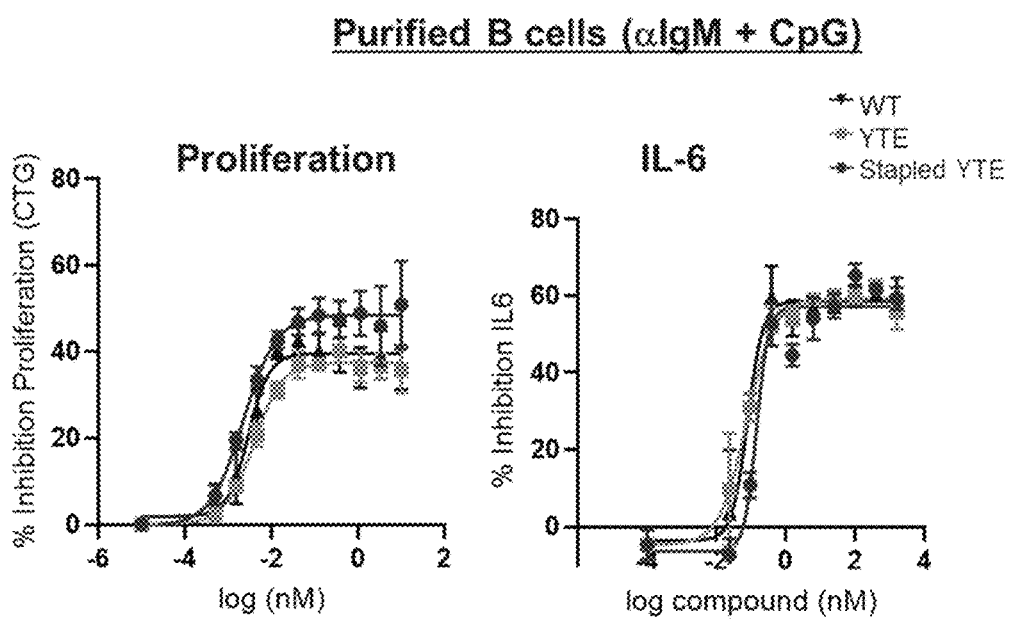
FIG. 6 depicts experimental results demonstrating that the stapled bispecific molecule inhibited B cell function.

CD22×CD79b bispecific antibodies impacted B-cell distal readouts of proliferation and cytokine production (FIG. 6). The B-cell distal read-outs (proliferation, cytokine secretion) were strongly inhibited by a stapled CD22×CD79b bispecific antibody. Purified B-cells were cultured for 30 minutes with the following prior to stimulation: CD22× CD79b bispecific antibodies, a CD22× Isotype bispecific antibody (C192B36), and an Isotype× CD79b bispecific antibody (C192B2). After the 30 minute incubations, B-cells were then stimulated with a synergistic dose of anti-IgM F(ab)'2 (2.5 µg/mL) and CPG (0.3125 µM). As shown in FIG. 6, the CD22×CD79b antibodies (WT, YTE, and stapled YTE) were able to significantly reduce B-cell proliferation in response to BCR and +TLR stimulation in comparison to the isotype control arms. Furthermore, B-cell IL-6 production of IL-6 in the presence of WT, YTE, and stapled YTE molecules was reduced (FIG. 6) while again the isotype control arms showed little to no effect.

Figure 7:
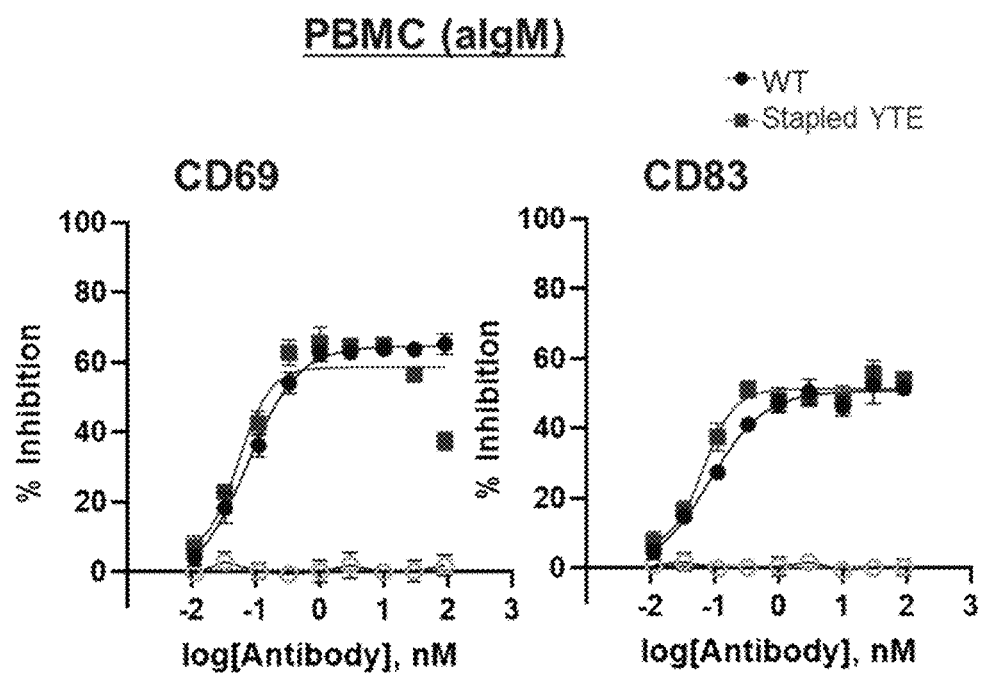
FIG. 7 depicts experimental results demonstrating that the CD22×CD79b bispecific antibodies reduced B cell activation as demonstrated by decreased expression of activation markers CD69 and CD83.

To explore the impact of the CD22×CD79b bispecific on B cell activation, experiments were performed in peripheral blood mononuclear cell (PBMC) assay. The CD22×CD79b bispecific antibodies reduced B cell activation as demonstrated by decreased expression of activation markers CD69 and CD83. The PBMCs were preincubated with the WT and stapled YTE, or an Isotype×CD79b bispecific antibody (C192B2) for 30 minutes prior to addition of anti-IgM F(ab)'2 (10 µg/mL). As shown in FIG. 7, the CD22×CD79b antibodies (WT and stapled YTE) reduced B-cell activation in response to IgM BCR stimulation in comparison to Isotype×CD79b bispecific antibody.

We claim:

1. A bispecific antibody or bispecific binding fragment comprising:
   a) a first antigen-binding arm that binds cluster of differentiation 79B protein (CD79B), comprising a first variable heavy domain (VH1) and further comprising a first variable light domain (VL1); and
   b) a second antigen-binding arm that binds cluster of differentiation 22 (CD22), comprising a second variable heavy domain (VH2) and further comprising a second variable light domain (VL2), wherein the second antigen-binding arm that binds CD22 comprises at least one selected from the group consisting of:
   (i) a VH2 comprising the HCDR1 of SEQ ID NO: 1, the HCDR2 of SEQ ID NO: 2, and the HCDR3 of SEQ ID NO:3, and a VL2 comprising the LCDR1 of SEQ ID NO: 4, the LCDR2 of SEQ ID NO:5, and the LCDR3 of SEQ ID NO:6; and
   (ii) the VH2 comprises SEQ ID NO:7 and the VL2 comprises SEQ ID NO: 8.

2. The bispecific antibody or bispecific binding fragment of claim 1, wherein the first antigen-binding arm that binds CD79b comprises a VH and VL selected from the group consisting of:
   a) the VH1 comprises the HCDR1 of SEQ ID NO:9, the HCDR2 of SEQ ID NO: 10, and the HCDR3 of SEQ ID NO: 11; and the VL1 comprises the LCDR1 of SEQ ID NO: 12, the LCDR2 of SEQ ID NO: 13, and the LCDR3 of SEQ ID NO: 14;
   b) the VH1 comprises the HCDR1 of SEQ ID NO: 17, the HCDR2 of SEQ ID NO: 18, and the HCDR3 of SEQ ID NO: 19; and the VL1 comprises the LCDR1 of SEQ ID NO:20, the LCDR2 of SEQ ID NO:21, and the LCDR3 of SEQ ID NO:22;
   c) the VH1 comprises the HCDR1 of SEQ ID NO:25, the HCDR2 of SEQ ID NO:26, and the HCDR3 of SEQ ID NO:27; and the VL1 comprises the LCDR1 of SEQ ID NO:28, the LCDR2 of SEQ ID NO:29, and the LCDR3 of SEQ ID NO:30;
   d) the VH1 comprises the HCDR1 of SEQ ID NO:33, the HCDR2 of SEQ ID NO:34, and the HCDR3 of SEQ ID NO:35; and the VL1 comprises the LCDR1 of SEQ ID NO:36, the LCDR2 of SEQ ID NO:37, and the LCDR3 of SEQ ID NO:38;
   e) the VH1 comprises the HCDR1 of SEQ ID NO:41, the HCDR2 of SEQ ID NO:42, and the HCDR3 of SEQ ID NO:43; and the VL1 comprises the LCDR1 of SEQ ID NO:44, the LCDR2 of SEQ ID NO:45, and the LCDR3 of SEQ ID NO:46;
   f) the VH1 comprises the HCDR1 of SEQ ID NO:49, the HCDR2 of SEQ ID NO:50, and the HCDR3 of SEQ ID NO:51; and the VL1 comprises the LCDR1 of SEQ ID NO:52, the LCDR2 of SEQ ID NO:53, and the LCDR3 of SEQ ID NO:54; and
   g) the VH1 comprises the HCDR1 of SEQ ID NO:57, the HCDR2 of SEQ ID NO:58, and the HCDR3 of SEQ ID NO:59; and the VL1 comprises the LCDR1 of SEQ ID NO:60, the LCDR2 of SEQ ID NO:61, and the LCDR3 of SEQ ID NO:62.

3. The bispecific antibody or bispecific binding fragment of claim 1, wherein the first antigen-binding arm that binds CD79b comprises a VH and VL selected from the group consisting of:
   a) the VH of SEQ ID NO: 15 and the VL of SEQ ID NO: 16;
   b) the VH of SEQ ID NO: 23 and the VL of SEQ ID NO: 24;
   c) the VH of SEQ ID NO: 31 and the VL of SEQ ID NO: 32;
   d) the VH of SEQ ID NO: 39 and the VL of SEQ ID NO: 40;
   e) the VH of SEQ ID NO: 47 and the VL of SEQ ID NO: 48;
   f) the VH of SEQ ID NO: 55 and the VL of SEQ ID NO: 56;
   g) the VH of SEQ ID NO: 63 and the VL of SEQ ID NO: 64; and
   h) the VH of SEQ ID NO: 80 and the VL of SEQ ID NO: 81.

4. The bispecific antibody or bispecific binding fragment of claim 1, wherein the first antigen-binding arm that binds CD79b comprises at least one selected from the group consisting of:
   a) a VH1 comprising the HCDR1 of SEQ ID NO:9, the HCDR2 of SEQ ID NO: 10, and the HCDR3 of SEQ ID NO: 11; and a VL1 comprising the LCDR1 of SEQ ID NO: 12, the LCDR2 of SEQ ID NO: 13, and the LCDR3 of SEQ ID NO: 14; and
   b) the VH1 comprises SEQ ID NO: 80 and the VL1 comprises SEQ ID NO: 81.

5. The bispecific antibody or bispecific binding fragment of claim 1, wherein each of the first antigen-binding arm and the second binding arm comprises at least one selected from the group consisting of a single-chain variable fragment (scFv), an (scFv)$_2$, an antigen-binding fragment (Fab), a F(ab')$_2$, a Fd, a Fv, a VHH, and a dAB.

6. The bispecific antibody or bispecific binding fragment of claim 5, wherein the first antigen-binding arm comprises an scFv, and the second antigen-binding arm comprises a Fab.

7. The bispecific antibody or bispecific binding fragment of claim 6, wherein the first antigen-binding arm comprises an scFv having the amino acid sequence of SEQ ID NO:82.

8. The bispecific antibody or bispecific binding fragment of claim 1, wherein the first antigen-binding arm that binds CD79b comprises a first Fragment crystallizable (Fc) domain, and wherein the second antigen-binding arm that binds CD22 comprises a second Fc domain, wherein at least one of the first and second Fc domain comprises one or more mutations that promote heterodimerization of the Fc domains, reduce Fc binding to a Fcγ receptor, reduce Fc binding to protein A, extend the half-life of the multispecific antibody or multispecific binding fragment, or any combination thereof.

9. The bispecific antibody or bispecific binding fragment of claim 8, wherein at least one of the first and second Fc domain comprises one or more mutations selected from the group consisting of:
   a) one or more mutations that promote heterodimerization of the Fc domains selected from the group consisting of T366S, L368A, T366W, and Y407V (EU numbering);
   b) one or more mutations that reduce Fc binding to a Fcγ receptor selected from the group consisting of L234A, L235A, and D265S according to EU numbering;
   c) one or more mutations that reduce Fc binding to protein A selected from the group consisting of H435R and Y436F according to EU numbering;
   d) one or more mutations that extend the half-life of the bispecific antibody or bispecific binding fragment selected from the group consisting of M252Y, S254T, and T256E according to EU numbering.

10. The bispecific antibody or bispecific binding fragment of claim 9, wherein at least one of the first and second Fc domain comprises one or more mutations selected from the group consisting of:
   a) one or more mutations that promote heterodimerization of the Fc domains wherein the first Fc domain comprise mutation T366W, and wherein the second Fc domain comprises mutations T366S, L368A, and Y407V;
   b) one or more mutations that reduce Fc binding to a Fcγ receptor, wherein both the first Fc domain and the second Fc domain comprise mutations L234A, L235A, and D265S;
   c) one or more mutations that reduce Fc binding to protein A, wherein the second Fc domain comprises mutations H435R and Y436F;
   d) one or more mutations that extend the half-life of the bispecific antibody or bispecific binding fragment wherein both the first Fc domain and the second Fc domain comprise mutations M252Y, S254T, and T256E.

11. The bispecific antibody or bispecific binding fragment of claim 10, wherein the first Fc domain comprises SEQ ID NO:89, and wherein the second Fc domain comprises SEQ ID NO:90.

12. The bispecific antibody or bispecific binding fragment of claim 1, comprising SEQ ID NO:79 as the amino acid sequence comprising (i) a scFv that binds CD79B and (ii) a first Fc domain, SEQ ID NO: 83 as the amino acid sequence comprising (i) the VH of a Fab that binds CD22 and (ii) a second Fc domain, and SEQ ID NO: 84 as the amino acid sequence comprising the VL of a Fab that binds CD22.

13. An immunoconjugate comprising the bispecific antibody or bispecific binding fragment of claim 1 conjugated to a therapeutic agent or an imaging agent.

14. A pharmaceutical composition comprising the bispecific antibody or bispecific binding fragment of claim 1 and a pharmaceutically acceptable carrier.

15. A polynucleotide encoding the bispecific antibody or bispecific binding fragment of claim 1.

16. A method of modulating B cell activation, inhibiting aberrant B cell activation, decreasing B cell proliferation, decreasing cytokine production or reducing B cell activation in a subject, comprising administering an effective amount of a bispecific antibody or bispecific binding fragment to the subject for a time sufficient to modulate B cell activation, inhibit aberrant B cell activation, decrease B cell proliferation, decrease cytokine production or reduce B cell activation, wherein the bispecific antibody or bispecific binding fragment comprises a) a first antigen-binding arm that binds cluster of differentiation 79B protein (CD79B), comprising a first variable heavy domain (VH1) and further comprising a first variable light domain (VL1); and b) a second antigen-binding arm that binds cluster of differentiation 22 (CD22), comprising a second variable heavy domain (VH2) and further comprising a second variable light domain (VL2), wherein:
   the VH1 comprises the HCDR1 of SEQ ID NO:9, the HCDR2 of SEQ ID NO: 10, and the HCDR3 of SEQ ID NO: 11, and the VL1 comprises the LCDR1 of SEQ ID NO:12, the LCDR2 of SEQ ID NO: 13, and the LCDR3 of SEQ ID NO: 14; and wherein
   the VH2 comprises the HCDR1 of SEQ ID NO: 1, the HCDR2 of SEQ ID NO:2, and the HCDR3 of SEQ ID NO:3, and the VL2 comprising the LCDR1 of SEQ ID NO:4, the LCDR2 of SEQ ID NO:5, and the LCDR3 of SEQ ID NO:6.

17. A bispecific antibody or bispecific binding fragment comprising:
   a) a first antigen-binding arm that binds cluster of differentiation 79B protein (CD79B), comprising a first variable heavy domain (VH1) and further comprising a first variable light domain (VL1), wherein the first antigen-arm that binds CD79B comprises at least one selected from the group consisting of:
   (i) the VH1 comprises the HCDR1 of SEQ ID NO:9, the HCDR2 of SEQ ID NO: 10, and the HCDR3 of SEQ ID NO:11; and the VL1 comprises the LCDR1 of SEQ ID NO: 12, the LCDR2 of SEQ ID NO: 13, and the LCDR3 of SEQ ID NO: 14;
   (ii) the VH1 comprises the HCDR1 of SEQ ID NO:17, the HCDR2 of SEQ ID NO: 18, and the HCDR3 of SEQ ID NO: 19; and the VL1 comprises the LCDR1 of SEQ ID NO:20, the LCDR2 of SEQ ID NO:21, and the LCDR3 of SEQ ID NO:22;
   (iii) the VH1 comprises the HCDR1 of SEQ ID NO:25, the HCDR2 of SEQ ID NO:26, and the HCDR3 of SEQ ID NO:27; and the VL1 comprises the LCDR1 of SEQ ID NO:28, the LCDR2 of SEQ ID NO:29, and the LCDR3 of SEQ ID NO:30;
   (iv) the VH1 comprises the HCDR1 of SEQ ID NO:33, the HCDR2 of SEQ ID NO:34, and the HCDR3 of SEQ ID NO:35; and the VL1 comprises the LCDR1 of SEQ ID NO:36, the LCDR2 of SEQ ID NO:37, and the LCDR3 of SEQ ID NO:38;
   (v) the VH1 comprises the HCDR1 of SEQ ID NO:41, the HCDR2 of SEQ ID NO:42, and the HCDR3 of SEQ ID NO:43; and the VL1 comprises the LCDR1 of SEQ ID NO:44, the LCDR2 of SEQ ID NO:45, and the LCDR3 of SEQ ID NO:46;
   (vi) the VH1 comprises the HCDR1 of SEQ ID NO:49, the HCDR2 of SEQ ID NO:50, and the HCDR3 of SEQ ID NO:51; and the VL1 comprises the LCDR1 of SEQ ID NO:52, the LCDR2 of SEQ ID NO:53, and the LCDR3 of SEQ ID NO:54; and
(vii) the VH1 comprises the HCDR1 of SEQ ID NO:57, the HCDR2 of SEQ ID NO:58, and the HCDR3 of SEQ ID NO:59; and the VL1 comprises the LCDR1 of SEQ ID NO:60, the LCDR2 of SEQ ID NO:61, and the LCDR3 of SEQ ID NO:62; and
b) a second antigen-binding arm that binds cluster of differentiation 22 (CD22), comprising a second variable heavy domain (VH2) and further comprising a second variable light domain (VL2).

18. The bispecific antibody or bispecific binding fragment of claim 17, wherein the first antigen-binding arm that binds CD79b comprises a VH and VL selected from the group consisting of:
a) the VH of SEQ ID NO: 15 and the VL of SEQ ID NO: 16;
b) the VH of SEQ ID NO: 23 and the VL of SEQ ID NO: 24;
c) the VH of SEQ ID NO: 31 and the VL of SEQ ID NO: 32;
d) the VH of SEQ ID NO: 39 and the VL of SEQ ID NO: 40;
e) the VH of SEQ ID NO: 47 and the VL of SEQ ID NO: 48;
f) the VH of SEQ ID NO: 55 and the VL of SEQ ID NO: 56;
g) the VH of SEQ ID NO: 63 and the VL of SEQ ID NO: 64; and
h) the VH of SEQ ID NO: 80 and the VL of SEQ ID NO: 81.

19. The bispecific antibody or bispecific binding fragment of claim 17, wherein the first antigen-binding arm that binds CD79b comprises at least one selected from the group consisting of:
a) a VH1 comprising the HCDR1 of SEQ ID NO:9, the HCDR2 of SEQ ID NO: 10, and the HCDR3 of SEQ ID NO:11; and a VL1 comprising the LCDR1 of SEQ ID NO: 12, the LCDR2 of SEQ ID NO: 13, and the LCDR3 of SEQ ID NO: 14; and
b) the VH1 comprises SEQ ID NO: 80 and the VL1 comprises SEQ ID NO: 81.

20. The bispecific antibody or bispecific binding fragment of claim 17, wherein each of the first antigen-binding arm and the second binding arm comprises at least one selected from the group consisting of a single-chain variable fragment (scFv), an (scFv) 2, an antigen-binding fragment (Fab), a F (ab') 2, a Fd, a Fv, a VHH, and a dAB.

21. The bispecific antibody or bispecific binding fragment of claim 20, wherein the first antigen-binding arm comprises an scFv, and the second antigen-binding arm comprises a Fab.

22. The bispecific antibody or bispecific binding fragment of claim 21, wherein the first antigen-binding arm comprises an scFv having the amino acid sequence of SEQ ID NO:82.

23. The bispecific antibody or bispecific binding fragment of claim 17, wherein the first antigen-binding arm that binds CD79b comprises a first Fragment crystallizable (Fc) domain, and wherein the second antigen-binding arm that binds CD22 comprises a second Fc domain, wherein at least one of the first and second Fc domain comprises one or more mutations that promote heterodimerization of the Fc domains, reduce Fc binding to a Fcγ receptor, reduce Fc binding to protein A, extend the half-life of the multispecific antibody or multispecific binding fragment, or any combination thereof.

24. The bispecific antibody or bispecific binding fragment of claim 23, wherein at least one of the first and second Fc domain comprises one or more mutations selected from the group consisting of:
a) one or more mutations that promote heterodimerization of the Fc domains selected from the group consisting of T366S, L368A, T366W, and Y407V according to EU numbering;
b) one or more mutations that reduce Fc binding to a Fcγ receptor selected from the group consisting of L234A, L235A, and D265S according to EU numbering;
c) one or more mutations that reduce Fc binding to protein A selected from the group consisting of H435R and Y436F (EU numbering);
d) one or more mutations that extend the half-life of the bispecific antibody or bispecific binding fragment selected from the group consisting of M252Y, S254T, and T256E according to EU numbering.

25. The bispecific antibody or bispecific binding fragment of claim 24, wherein at least one of the first and second Fc domain comprises one or more mutations selected from the group consisting of:
a) one or more mutations that promote heterodimerization of the Fc domains wherein the first Fc domain comprise mutation T366W, and wherein the second Fc domain comprises mutations T366S, L368A, and Y407V;
b) one or more mutations that reduce Fc binding to a Fcγ receptor, wherein both the first Fc domain and the second Fc domain comprise mutations L234A, L235A, and D265S;
c) one or more mutations that reduce Fc binding to protein A, wherein the second Fc domain comprises mutations H435R and Y436F;
d) one or more mutations that extend the half-life of the bispecific antibody or bispecific binding fragment wherein both the first Fc domain and the second Fc domain comprise mutations M252Y, S254T, and T256E.

26. The bispecific antibody or bispecific binding fragment of claim 25, wherein the first Fc domain comprises SEQ ID NO:89, and wherein the second Fc domain comprises SEQ ID NO:90.

27. An immunoconjugate comprising the bispecific antibody or bispecific binding fragment of claim 17 conjugated to a therapeutic agent or an imaging agent.

28. A pharmaceutical composition comprising the bispecific antibody or bispecific binding fragment of claim 17 and a pharmaceutically acceptable carrier.

29. A polynucleotide encoding the bispecific antibody or bispecific binding fragment of claim 17.

* * * * *